(12) United States Patent
Keshavarz-Shokri et al.

(10) Patent No.: US 8,802,868 B2
(45) Date of Patent: Aug. 12, 2014

(54) SOLID FORMS OF (R)-1(2,2-DIFLUOROBENZO[D][1,3]DIOXO1-5-YL)-N-(1-(2,3-DIHYDROXYPROPYL-6-FLUORO-2-(1-HYDROXY-2-METHYLPRO-PAN2-YL)-1H-INDOL-5-YL)-CYCLOPRO-PANECARBOXAMIDE

(71) Applicant: Vertex Pharmaceuticals Incorporated, Cambridge, MA (US)

(72) Inventors: Ali Keshavarz-Shokri, San Diego, CA (US); Beili Zhang, San Diego, CA (US); Tim Edward Alcacio, San Diego, CA (US); Elaine Chungmin Lee, Cambridge, MA (US); Yuegang Zhang, Wayland, MA (US); Mariusz Krawiec, Marlborough, MA (US)

(73) Assignee: Vertex Pharmaceuticals Incorporated, Boston, MA (US)

( * ) Notice: Subject to any disclaimer, the term of this patent is extended or adjusted under 35 U.S.C. 154(b) by 0 days.

(21) Appl. No.: 13/624,241

(22) Filed: Sep. 21, 2012

(65) Prior Publication Data
US 2013/0143918 A1 Jun. 6, 2013

Related U.S. Application Data

(63) Continuation of application No. PCT/US2011/030032, filed on Mar. 25, 2011.

(60) Provisional application No. 61/321,561, filed on Apr. 7, 2010, provisional application No. 61/321,636, filed on Apr. 7, 2010, provisional application No. 61/319,953, filed on Apr. 1, 2010, provisional application No. 61/317,376, filed on Mar. 25, 2010.

(51) Int. Cl.
 C07D 405/12 (2006.01)
 A61K 31/36 (2006.01)

(52) U.S. Cl.
 USPC .......................................... 548/454; 514/414

(58) Field of Classification Search
 None
 See application file for complete search history.

(56) References Cited

U.S. PATENT DOCUMENTS

| | | | |
|---|---|---|---|
| 7,407,976 B2 | 8/2008 | Miller et al. |
| 7,495,103 B2 | 2/2009 | Hadida Ruah et al. |
| 7,553,855 B2 | 6/2009 | Young et al. |
| 7,598,412 B2 | 10/2009 | Hadida Ruah et al. |
| 7,645,789 B2 | 1/2010 | Hadida-Ruah et al. |
| 7,659,268 B2 | 2/2010 | Hadida Ruah et al. |
| 7,671,221 B2 | 3/2010 | Hadida Ruah et al. |
| 7,691,902 B2 | 4/2010 | Hadida-Ruah et al. |
| 7,741,321 B2 | 6/2010 | Hadida-Ruah et al. |
| 7,754,739 B2 | 7/2010 | Hadida-Ruah et al. |
| 7,776,905 B2 | 8/2010 | Hadida Ruah et al. |
| 7,846,951 B2 | 12/2010 | Miller et al. |
| 7,956,052 B2 | 6/2011 | Hadida Ruah et al. |
| 7,973,038 B2 | 7/2011 | Hadida Ruah et al. |
| 7,973,169 B2 | 7/2011 | Hadida Ruah et al. |
| 7,977,322 B2 | 7/2011 | Ruah et al. |
| 7,999,113 B2 | 8/2011 | Hadida-Ruah et al. |
| 8,012,999 B2 | 9/2011 | Hadida Ruah et al. |
| 8,039,491 B2 | 10/2011 | Hadida Ruah et al. |
| 8,076,357 B2 | 12/2011 | Young et al. |
| 8,101,767 B2 | 1/2012 | Ruah et al. |
| 8,124,781 B2 | 2/2012 | Siesel |
| 8,163,772 B2 | 4/2012 | Demattei et al. |
| 8,188,283 B2 | 5/2012 | Binch et al. |
| 8,227,615 B2 | 7/2012 | Hadida Ruah et al. |
| 8,232,302 B2 | 7/2012 | Miller et al. |
| 8,242,149 B2 | 8/2012 | Ruah et al. |
| 8,299,099 B2 | 10/2012 | Ruah et al. |
| 8,314,239 B2 | 11/2012 | Binch et al. |
| 8,314,256 B2 | 11/2012 | Ruah et al. |
| 8,318,733 B2 | 11/2012 | Hadida-Ruah et al. |
| 8,324,207 B2 | 12/2012 | Hadida-Ruah et al. |
| 8,324,242 B2 | 12/2012 | Ruah et al. |
| 8,344,147 B2 | 1/2013 | Ambhaikar et al. |
| 8,354,427 B2 | 1/2013 | VanGoor |
| 8,362,253 B2 | 1/2013 | Demattei et al. |
| 8,367,660 B2 | 2/2013 | Binch et al. |
| 8,389,727 B2 | 3/2013 | Zhang et al. |
| 8,399,479 B2 | 3/2013 | Binch et al. |
| 8,404,849 B2 | 3/2013 | Sun et al. |
| 8,404,865 B2 | 3/2013 | Ambhaikar et al. |
| 8,410,132 B2 | 4/2013 | Binch et al. |
| 8,410,274 B2 | 4/2013 | Hurter et al. |
| 8,415,387 B2 | 4/2013 | Ruah et al. |
| 8,431,605 B2 | 4/2013 | Hadida-Ruah et al. |
| 8,436,014 B2 | 5/2013 | Zhang et al. |
| 8,598,205 B2 | 12/2013 | Binch et al. |
| 2005/0059687 A1 | 3/2005 | Makings et al. |
| 2005/0113423 A1 | 5/2005 | Van Goor et al. |
| 2006/0052358 A1 | 3/2006 | Ruah et al. |
| 2007/0105833 A1 | 5/2007 | Ruah et al. |

(Continued)

FOREIGN PATENT DOCUMENTS

| | | |
|---|---|---|
| WO | 2010053471 | 5/2010 |
| WO | 2010054138 | 5/2010 |

OTHER PUBLICATIONS

Caira, M.R., "Crystalline Polymorphism of Organic Compounds", Topics in Current Chemistry (1998), vol. 198, pp. 165-166.

(Continued)

Primary Examiner — Nyeemah A Grazier
(74) Attorney, Agent, or Firm — Honigman Miller Schwartz and Cohn LLP; Heidi M. Berven; Jonathan P. O'Brien

(57) ABSTRACT

The present invention relates to solid forms of (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide (Compound 1) in substantially crystalline form (Form A) or amorphous form, pharmaceutical compositions thereof, and methods of treatment therewith.

40 Claims, 19 Drawing Sheets

(56) References Cited

U.S. PATENT DOCUMENTS

| | | |
|---|---|---|
| 2008/0071095 A1 | 3/2008 | Hadida-Ruah et al. |
| 2008/0132560 A1 | 6/2008 | Chow et al. |
| 2008/0306062 A1 | 12/2008 | Hadida-Ruah et al. |
| 2009/0105272 A1 | 4/2009 | Grootenhuis et al. |
| 2009/0131492 A1 | 5/2009 | Ruah et al. |
| 2009/0143381 A1 | 6/2009 | Hadida-Ruah et al. |
| 2009/0170905 A1 | 7/2009 | Keshavarz-Shokri et al. |
| 2009/0176839 A1 | 7/2009 | Keshavarz-Shokri et al. |
| 2009/0246820 A1 | 10/2009 | Singh et al. |
| 2009/0253736 A1 | 10/2009 | Hadida-Ruah et al. |
| 2010/0036130 A1 | 2/2010 | Siesel |
| 2010/0074949 A1 | 3/2010 | Rowe et al. |
| 2010/0087490 A1 | 4/2010 | Young |
| 2010/0113508 A1 | 5/2010 | Binch et al. |
| 2010/0125090 A1 | 5/2010 | Hadida-Ruah et al. |
| 2010/0144798 A1 | 6/2010 | Van Goor et al. |
| 2010/0249113 A1 | 9/2010 | Hadida-Ruah et al. |
| 2010/0249180 A1 | 9/2010 | Gallardo-Godoy |
| 2010/0256184 A1 | 10/2010 | Rowe et al. |
| 2010/0267768 A1 | 10/2010 | Demattei et al. |
| 2010/0331344 A1 | 12/2010 | Hadida-Ruah et al. |
| 2011/0008259 A1 | 1/2011 | Binch et al. |
| 2011/0060024 A1 | 3/2011 | Hadida-Ruah et al. |
| 2011/0064811 A1 | 3/2011 | Hurter et al. |
| 2011/0071206 A1 | 3/2011 | Ruah et al. |
| 2011/0098311 A1 | 4/2011 | Van Goor et al. |
| 2011/0177999 A1 | 7/2011 | Singh et al. |
| 2011/0230519 A1 | 9/2011 | Arekar et al. |
| 2011/0251253 A1 | 10/2011 | Keshavarz-Shokri et al. |
| 2011/0256220 A1 | 10/2011 | Verwijs et al. |
| 2011/0257223 A1 | 10/2011 | Van Goor et al. |
| 2011/0263654 A1 | 10/2011 | Keshavarz-Shokri et al. |
| 2011/0288122 A1 | 11/2011 | Van Goor et al. |
| 2011/0306637 A1 | 12/2011 | Hadida-Ruah et al. |
| 2012/0010257 A1 | 1/2012 | Hadida-Ruah et al. |
| 2012/0015999 A1 | 1/2012 | Alargova et al. |
| 2012/0035179 A1 | 2/2012 | Hadida-Ruah et al. |
| 2012/0046330 A1 | 2/2012 | Alargova et al. |
| 2012/0064157 A1 | 3/2012 | Dokou et al. |
| 2012/0071504 A1 | 3/2012 | Yang et al. |
| 2012/0122921 A1 | 5/2012 | Demattei et al. |
| 2012/0122922 A1 | 5/2012 | Young et al. |
| 2012/0184583 A1 | 7/2012 | Van Goor et al. |
| 2012/0190856 A1 | 7/2012 | Siesel |
| 2012/0203006 A1 | 8/2012 | Siesel |
| 2012/0208841 A1 | 8/2012 | Binch et al. |
| 2012/0220625 A1 | 8/2012 | Rowe et al. |
| 2012/0232059 A1 | 9/2012 | Hadida-Ruah et al. |
| 2012/0258983 A1 | 10/2012 | Rowe et al. |
| 2012/0259129 A1 | 10/2012 | Ambhaikar et al. |
| 2012/0270869 A1 | 10/2012 | Hadida-Ruah et al. |
| 2012/0277268 A1 | 11/2012 | Keshavarz-Shokri et al. |
| 2012/0309758 A1 | 12/2012 | Sheth et al. |
| 2012/0322798 A1 | 12/2012 | Hadida-Ruah et al. |
| 2013/0011923 A1 | 1/2013 | Ruah et al. |
| 2013/0012536 A1 | 1/2013 | Hadida-Ruah et al. |
| 2013/0018071 A1 | 1/2013 | Arekar et al. |
| 2013/0023538 A1 | 1/2013 | Hadida-Ruah et al. |
| 2013/0035327 A1 | 2/2013 | Hadida-Ruah et al. |
| 2013/0040986 A1 | 2/2013 | Binch et al. |
| 2013/0072522 A1 | 3/2013 | Demattei et al. |
| 2013/0072687 A1 | 3/2013 | Ambhaikar et al. |
| 2013/0079367 A1 | 3/2013 | Arekar et al. |
| 2013/0085158 A1 | 4/2013 | Keshavarz-Shokri et al. |
| 2013/0090354 A1 | 4/2013 | Van Goor et al. |
| 2013/0095181 A1 | 4/2013 | Verwijs et al. |
| 2013/0109717 A1 | 5/2013 | Demattei et al. |
| 2013/0116238 A1 | 5/2013 | Looker et al. |
| 2013/0131107 A1 | 5/2013 | Van Goor et al. |
| 2013/0137722 A1 | 5/2013 | Zhang et al. |
| 2013/0143918 A1 | 6/2013 | Keshavarz-Shokri et al. |
| 2013/0143919 A1 | 6/2013 | Van Goor et al. |
| 2013/0158071 A1 | 6/2013 | Van Goor et al. |
| 2013/0165442 A1 | 6/2013 | Sheth et al. |
| 2013/0178471 A1 | 7/2013 | Ruah et al. |
| 2013/0178496 A1 | 7/2013 | Binch et al. |
| 2013/0184276 A1 | 7/2013 | Hadida-Ruah et al. |
| 2013/0186801 A1 | 7/2013 | Verwijs et al. |
| 2013/0196983 A1 | 8/2013 | Binch et al. |
| 2013/0224293 A1 | 8/2013 | Dokou et al. |
| 2013/0231364 A1 | 9/2013 | Binch et al. |
| 2013/0231368 A1 | 9/2013 | Zhang et al. |
| 2013/0237568 A1 | 9/2013 | Hadida-Ruah et al. |
| 2013/0237569 A1 | 9/2013 | Hadida-Ruah et al. |
| 2013/0245010 A1 | 9/2013 | Hadida-Ruah et al. |
| 2013/0245011 A1 | 9/2013 | Hadida-Ruah et al. |
| 2013/0252333 A1 | 9/2013 | Hadida-Ruah et al. |
| 2013/0274477 A1 | 10/2013 | Siesel et al. |
| 2013/0296306 A1 | 11/2013 | Hadida-Ruah et al. |
| 2013/0296364 A1 | 11/2013 | Hadida-Ruah et al. |
| 2013/0296379 A1 | 11/2013 | Keshavarz-Shokri et al. |
| 2013/0303484 A1 | 11/2013 | Grootenhuis et al. |
| 2013/0303570 A1 | 11/2013 | Binch et al. |
| 2013/0317020 A1 | 11/2013 | Ruah et al. |
| 2013/0317060 A1 | 11/2013 | Hurter et al. |
| 2013/0324743 A1 | 12/2013 | Belmont et al. |
| 2013/0331567 A1 | 12/2013 | Hadida-Ruah et al. |

OTHER PUBLICATIONS

International Search Report for PCT/US2011/030032, mailed Feb. 8, 2011.

Konno, et al., European Journal of Pharmaceutics and Biopharmaceutics (2008), vol. 70, pp, 493-499.

Definition of amorphous in www.thefreedictionary.com/amorphous, May 1, 2012.

SOLID FORMS OF (R)-1(2,2-DIFLUOROBENZO[D][1,3]DIOXO1-5-YL)-N-(1-(2,3-DIHYDROXYPROPYL-6-FLUORO-2-(1-HYDROXY-2-METHYLPROPAN2-YL)-1H-INDOL-5-YL)-CYCLOPROPANE-CARBOXAMIDE

TECHNICAL FIELD OF THE INVENTION

The present invention relates to solid state forms, for example, crystalline and amorphous forms, of (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide, pharmaceutical compositions thereof, and methods therewith.

BACKGROUND OF THE INVENTION

CFTR is a cAMP/ATP-mediated anion channel that is expressed in a variety of cells types, including absorptive and secretory epithelia cells, where it regulates anion flux across the membrane, as well as the activity of other ion channels and proteins. In epithelia cells, normal functioning of CFTR is critical for the maintenance of electrolyte transport throughout the body, including respiratory and digestive tissue. CFTR is composed of approximately 1480 amino acids that encode a protein made up of a tandem repeat of transmembrane domains, each containing six transmembrane helices and a nucleotide binding domain. The two transmembrane domains are linked by a large, polar, regulatory (R)-domain with multiple phosphorylation sites that regulate channel activity and cellular trafficking.

The gene encoding CFTR has been identified and sequenced (See Gregory, R. J. et al. (1990) Nature 347:382-386; Rich, D. P. et al. (1990) Nature 347:358-362), (Riordan, J. R. et al. (1989) Science 245:1066-1073). A defect in this gene causes mutations in CFTR resulting in cystic fibrosis ("CF"), the most common fatal genetic disease in humans. Cystic fibrosis affects approximately one in every 2,500 infants in the United States. Within the general United States population, up to 10 million people carry a single copy of the defective gene without apparent ill effects. In contrast, individuals with two copies of the CF associated gene suffer from the debilitating and fatal effects of CF, including chronic lung disease.

In patients with cystic fibrosis, mutations in CFTR endogenously expressed in respiratory epithelia lead to reduced apical anion secretion causing an imbalance in ion and fluid transport. The resulting decrease in anion transport contributes to enhance mucus accumulation in the lung and the accompanying microbial infections that ultimately cause death in CF patients. In addition to respiratory disease, CF patients typically suffer from gastrointestinal problems and pancreatic insufficiency that, if left untreated, results in death. In addition, the majority of males with cystic fibrosis are infertile and fertility is decreased among females with cystic fibrosis. In contrast to the severe effects of two copies of the CF associated gene, individuals with a single copy of the CF associated gene exhibit increased resistance to cholera and to dehydration resulting from diarrhea—perhaps explaining the relatively high frequency of the CF gene within the population.

Sequence analysis of the CFTR gene of CF chromosomes has revealed a variety of disease-causing mutations (Cutting, G. R. et al. (1990) Nature 346:366-369; Dean, M. et al. (1990) Cell 61:863:870; and Kerem, B-S. et al. (1989) Science 245: 1073-1080; Kerem, B-S et al. (1990) Proc. Natl. Acad. Sci. USA 87:8447-8451). To date, greater than 1000 disease-causing mutations in the CF gene have been identified as reported by the scientific and medical literature. The most prevalent mutation is a deletion of phenylalanine at position 508 of the CFTR amino acid sequence, and is commonly referred to as ΔF508-CFTR. This mutation occurs in approximately 70 percent of the cases of cystic fibrosis and is associated with a severe disease. Other mutations include the R117H and G551D.

The deletion of residue 508 in ΔF508-CFTR prevents the nascent protein from folding correctly. This results in the inability of the mutant protein to exit the ER, and traffic to the plasma membrane. As a result, the number of channels present in the membrane is far less than observed in cells expressing wild-type CFTR. In addition to impaired trafficking, the mutation results in defective channel gating. Together, the reduced number of channels in the membrane and the defective gating lead to reduced anion transport across epithelia leading to defective ion and fluid transport. (Quinton, P. M. (1990), FASEB J. 4: 2709-2727). Studies have shown, however, that the reduced numbers of ΔF508-CFTR in the membrane are functional, albeit less than wild-type CFTR. (Dalemans et al. (1991), Nature Lond. 354: 526-528; Denning et al., supra; Pasyk and Foskett (1995), J. Cell. Biochem. 270: 12347-50). In addition to ΔF508-CFTR, other disease causing mutations in CFTR that result in defective trafficking, synthesis, and/or channel gating could be up- or down-regulated to alter anion secretion and modify disease progression and/or severity.

Although CFTR transports a variety of molecules in addition to anions, it is clear that this role (the transport of anions) represents one element in an important mechanism of transporting ions and water across the epithelium. The other elements include the epithelial $Na^+$ channel, ENaC, $Na^+/2Cl^-/K^+$ co-transporter, $Na^+$—$K^+$-ATPase pump and the basolateral membrane $K^+$ channels, that are responsible for the uptake of chloride into the cell.

These elements work together to achieve directional transport across the epithelium via their selective expression and localization within the cell. Chloride absorption takes place by the coordinated activity of ENaC and CFTR present on the apical membrane and the $Na^+$—$K^+$-ATPase pump and $Cl^-$ channels expressed on the basolateral surface of the cell. Secondary active transport of chloride from the luminal side leads to the accumulation of intracellular chloride, which can then passively leave the cell via $Cl^-$ channels, resulting in a vectorial transport. Arrangement of $Na^+/2Cl^-/K^+$ co-transporter, $Na^+$—$K^+$-ATPase pump and the basolateral membrane $K^+$ channels on the basolateral surface and CFTR on the luminal side coordinate the secretion of chloride via CFTR on the luminal side. Because water is probably never actively transported itself, its flow across epithelia depends on tiny transepithelial osmotic gradients generated by the bulk flow of sodium and chloride.

As discussed above, it is believed that the deletion of residue 508 in ΔF508-CFTR prevents the nascent protein from folding correctly, resulting in the inability of this mutant protein to exit the ER, and traffic to the plasma membrane. As a result, insufficient amounts of the mature protein are present at the plasma membrane and chloride transport within epithelial tissues is significantly reduced. In fact, this cellular phenomenon of defective endoplasmic reticulum (ER) processing of ATP-binding cassette (ABC) transporters by the ER machinery, has been shown to be the underlying basis not only for CF disease, but for a wide range of other isolated and inherited diseases. The two ways that the ER machinery can malfunction is either by loss of coupling to ER export of the proteins leading to degradation, or by the ER accumulation of these defective/misfolded proteins [Aridor M, et al., Nature Med., 5(7), pp 745-751 (1999); Shastry, B. S., et al., Neurochem. International, 43, pp 1-7 (2003); Rutishauser, J., et al., Swiss Med Wkly, 132, pp 211-222 (2002); Morello, J P et al., TIPS, 21 pp. 466-169 (2000); Bross P., et al., Human Mut., pp. 186-198 (1999)].

(R)-1-(2,2-d fluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide is disclosed in US published patent application US20090131492 (said publication being incorporated herein by reference in its entirety) as a modulator of CFTR activity and thus useful in treating CFTR-mediated diseases such as cystic fibrosis. However, there is a need for stable solid forms of said compound that can be used readily in pharmaceutical compositions suitable for use as therapeutics.

SUMMARY OF THE INVENTION

The present invention relates to solid forms of (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide (hereinafter "Compound 1") which has the structure below:

Compound 1

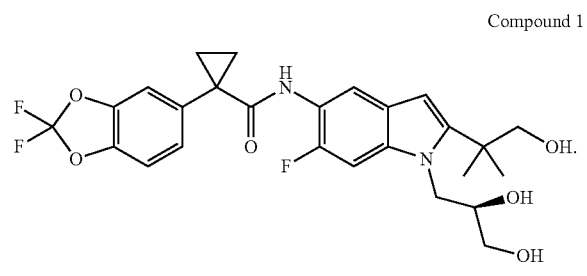 [SMILES: CC(C)(CO)c1cc2cc(NC(=O)C3(c4ccc5c(c4)OC(F)(F)O5)CC3)c(F)cc2n1C[C@@H](O)CO]

Compound 1 and pharmaceutically acceptable compositions thereof are useful for, treating or lessening the severity of CFTR mediated diseases such as, for example, cystic fibrosis. In one aspect, Compound 1 is in a substantially crystalline and salt free form referred to as Form A as described and characterized herein. In another aspect, Compound 1 is in an amorphous form as described and characterized herein. The properties of a solid relevant to its efficacy as a drug can be dependent on the form of the solid. For example, in a drug substance, variation in the solid form can lead to differences in properties such as melting point, dissolution rate, oral absorption, bioavailability, toxicology results and even clinical trial results.

Processes described herein can be used to prepare the compositions of this invention comprising Form A or amorphous form of Compound 1, or both. The amounts and the features of the components used in the processes would be as described herein.

DETAILED DESCRIPTION OF THE INVENTION

Definitions

Figure 1:
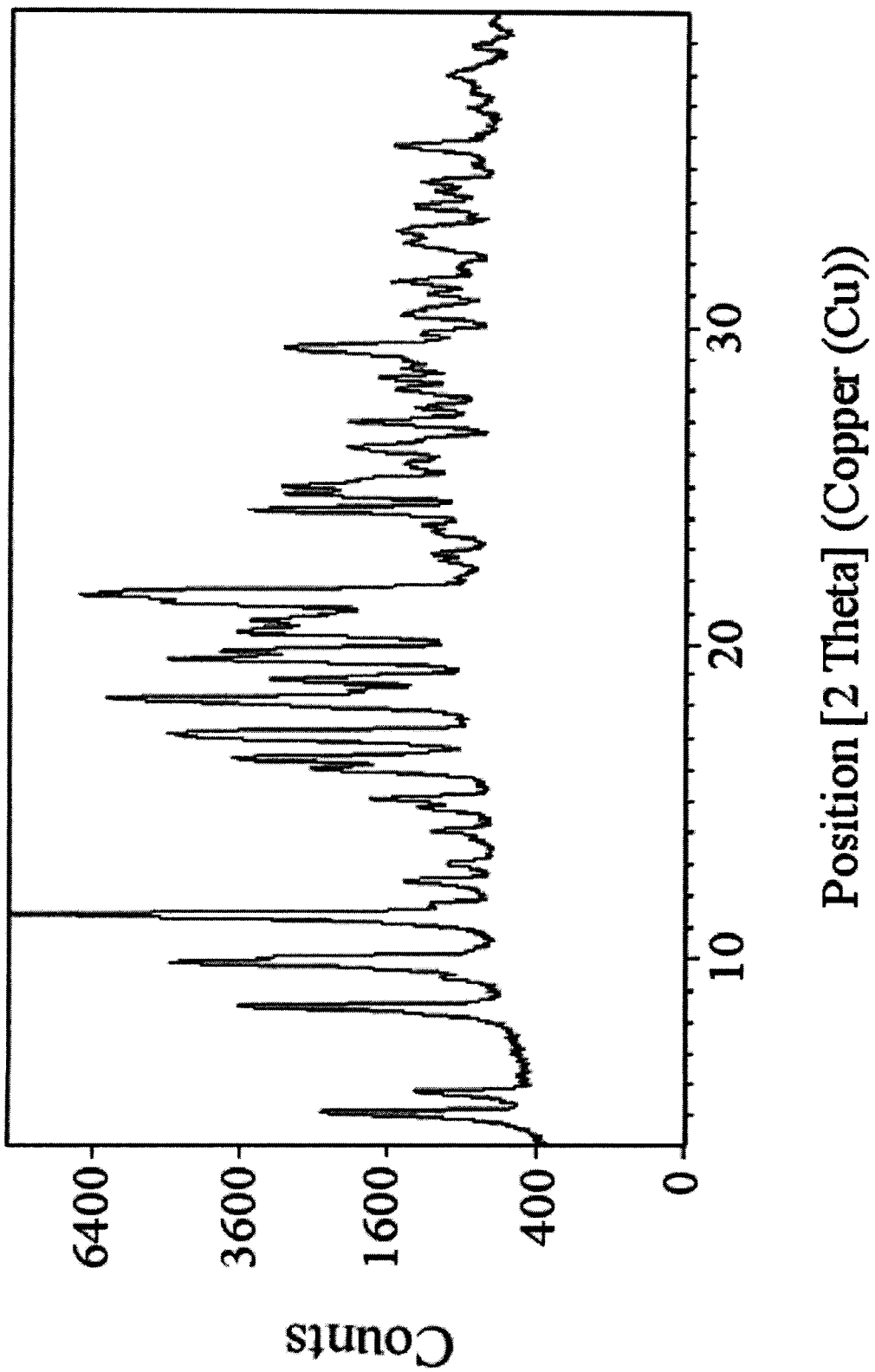
FIG. 1 is an X-ray powder diffraction pattern of Compound 1.

As used herein, the following definitions shall apply unless otherwise indicated.

The term "CFTR" as used herein means cystic fibrosis transmembrane conductance regulator or a mutation thereof capable of regulator activity, including, but not limited to, ΔF508 CFTR and G551D CFTR (see, e.g., http://www.genet.sickkids.on.ca/cftr/, for CFTR mutations).

As used herein the term "amorphous" refers to solid forms that consist of disordered arrangements of molecules and do not possess a distinguishable crystal lattice.

As used herein "crystalline" refers to compounds or compositions where the structural units are arranged in fixed geometric patterns or lattices, so that crystalline solids have rigid long range order. The structural units that constitute the crystal structure can be atoms, molecules, or ions. Crystalline solids show definite melting points.

The term "modulating" as used herein means increasing or decreasing, e.g. activity, by a measurable amount.

The term "chemically stable", as used herein, means that the solid form of Compound 1 does not decompose into one or more different chemical compounds when subjected to specified conditions, e.g., 40° C./75% relative humidity, for a specific period of time. e.g. 1 day, 2 days, 3 days, 1 week, 2 weeks, or longer. In some embodiments, less than 25% of the solid form of Compound 1 decomposes, in some embodiments, less than about 20%, less than about 15%, less than about 10%, less than about 5%, less than about 3%, less than about 1%, less than about 0.5% of the form of Compound 1 decomposes under the conditions specified. In some embodiments, no detectable amount of the solid form of Compound 1 decomposes.

The term "physically stable", as used herein, means that the solid form of Compound 1 does not change into one or more different physical forms of Compound 1 (e.g. different solid forms as measured by XRPD, DSC, etc.) when subjected to specific conditions, e.g., 40° C./75% relative humidity, for a specific period of time. e.g. 1 day, 2 days, 3 days, 1 week, 2 weeks, or longer. In some embodiments, less than 25% of the solid form of Compound 1 changes into one or more different physical forms when subjected to specified conditions. In some embodiments, less than about 20%, less than about 15%, less than about 10%, less than about 5%, less than about 3%, less than about 1%, less than about 0.5% of the solid form of Compound 1 changes into one or more different physical forms of Compound 1 when subjected to specified conditions. In some embodiments, no detectable amount of the solid form of Compound 1 changes into one or more physically different solid forms of Compound 1.

As used herein, the phrase "substantially amorphous Compound 1" is used interchangeably with the phrases "amorphous Compound 1," "amorphous Compound 1 substantially free of crystalline Compound 1," and "substantially amorphous (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide." In some embodiments, substantially amorphous Compound 1 has less than about 30% crystalline Compound 1, for example, less than about 30% of crystalline Compound 1, e.g., less than about 25% crystalline Compound 1, less than about 20% crystalline Compound 1, less than about 15% crystalline Compound 1, less than about 10% crystalline Compound 1, less than about 5% crystalline Compound 1, less than about 2% crystalline Compound 1.

As used herein, the phrase "substantially crystalline Compound 1 Form A" is used interchangeably with the phrases "Compound 1 Form A," and "crystalline Compound 1 Form A substantially free of amorphous Compound 1." In some embodiments, substantially crystalline Compound 1 Form A has less than about 30% amorphous Compound 1 or other solid forms, for example, less than about 30% of amorphous Compound 1 or other solid forms, e.g., less than about 25% amorphous Compound 1 or other solid forms, less than about 20% amorphous Compound 1 or other solid forms, less than about 15% amorphous Compound 1 or other solid forms, less than about 10% amorphous Compound 1 or other solid forms, less than about 5% amorphous Compound 1 or other solid forms, less than about 2% amorphous Compound 1 or other solid forms. In some embodiments, substantially crystalline Compound 1 Form A has less than about 1% amorphous Compound 1 or other solid forms.

The term "substantially free" (as in the phrase "substantially free of form X") when referring to a designated solid form of Compound 1 (e.g., an amorphous or crystalline form described herein) means that there is less than 20% (by weight) of the designated form(s) or co-form(s) (e.g., a crystalline or amorphous form of Compound 1) present, more preferably, there is less than 10% (by weight) of the designated form(s) present, more preferably, there is less than 5% (by weight) of the designated form(s) present, and most preferably, there is less than 1% (by weight) of the designated form(s) present.

The term "substantially pure" when referring to a designated solid form of Compound 1 (e.g., an amorphous or crystalline solid form described herein) means that the designated solid form contains less than 20% (by weight) of residual components such as alternate polymorphic or isomorphic crystalline form(s) or co-form(s) of Compound 1. It is preferred that a substantially pure solid form of Compound 1 contains less than 10% (by weight) of alternate polymorphic or isomorphic crystalline forms of Compound 1, more preferably less than 5% (by weight) of alternate polymorphic or isomorphic crystalline forms of Compound 1, and most preferably less than 1% (by weight) of alternate polymorphic or isomorphic crystalline forms of Compound 1.

As used herein, a "dispersion" refers to a disperse system in which one substance, the dispersed phase, is distributed, in discrete units, throughout a second substance (the continuous phase or vehicle). The size of the dispersed phase can vary considerably (e.g. colloidal particles of nanometer dimension, to multiple microns in size). In general, the dispersed phases can be solids, liquids, or gases. In the case of a solid dispersion, the dispersed and continuous phases are both solids. In pharmaceutical applications, a solid dispersion can include a crystalline drug (dispersed phase) in an amorphous polymer (continuous phase), or alternatively, an amorphous drug (dispersed phase) in an amorphous polymer (continuous phase). In some embodiments an amorphous solid dispersion includes the polymer constituting the dispersed phase, and the drug constitutes the continuos phase. In some embodiments, the dispersion includes amorphous Compound 1 or substantially amorphous Compound 1.

The term "solid amorphous dispersion" generally refers to a solid dispersion of two or more components, usually a drug and polymer, but possibly containing other components such as surfactants or other pharmaceutical excipients, where Compound 1 is amorphous or substantially amorphous (e.g., substantially free of crystalline Compound 1), and the physical stability and/or dissolution and/or solubility of the amorphous drug is enhanced by the other components.

As used herein, the terms "about" and "approximately", when used in connection with doses, amounts, or weight percent of ingredients of a composition or a dosage form, mean a dose, amount, or weight percent that is recognized by one of ordinary skill in the art to provide a pharmacological effect equivalent to that obtained from the specified dose, amount, or weight percent. Specifically the term "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 30%, 25%, 20%, 15%, 10%, 9%, 8%, 7%, 6%, 5%, 4%, 3%, 2%, 1%, 0.5%, 0.1%, or 0.05% of a given value or range.

The abbreviations "MTBE" and "DCM" stand for methyl t-butyl ether and dichloromethane, respectively.

The abbreviation "XRPD" stands for X-ray powder diffraction.

The abbreviation "DSC" stands for differential scanning calorimetry.

The abbreviation "TGA" stands for thermogravimetric analysis.

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention. All tautomeric forms of the Compound 1 are included herein. For example, Compound 1 may exist as tautomers, both of which are included herein:

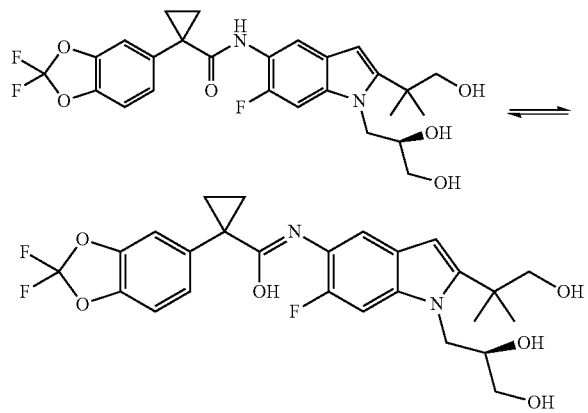

Additionally, unless otherwise stated, structures depicted herein are also meant to include compounds that differ only in the presence of one or more isotopically enriched atoms. For example, Compound 1, wherein one or more hydrogen atoms are replaced deuterium or tritium, or one or more carbon atoms are replaced by a $^{13}$C- or $^{14}$C-enriched carbon are within the scope of this invention. Such compounds are useful, for example, as analytical tools, probes in biological assays, or compounds with improved therapeutic profile.

In one aspect, the invention features (R)-1-(2,2-Difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide characterized as crystalline Form A.

In another embodiment, Form A is characterized by one or more peaks at 19.3 to 19.7 degrees, 21.5 to 21.9 degrees, and 16.9 to 17.3 degrees in an X-ray powder diffraction obtained using Cu K alpha radiation. In another embodiment, Form A is characterized by one or more peaks at about 19.5, 21.7, and 17.1 degrees. In another embodiment, Form A is further characterized by a peak at 20.2 to 20.6 degrees. In another embodiment, Form A is further characterized by a peak at about 20.4 degrees. In another embodiment, Form A is further characterized by a peak at 18.6 to 19.0 degrees. In another embodiment, Form A is further characterized by a peak at about 18.8 degrees. In another embodiment, Form A is further characterized by a peak at 24.5 to 24.9 degrees. In another embodiment, Form A is further characterized by a peak at about 24.7 degrees. In another embodiment, Form A is further characterized by a peak at 9.8 to 10.2 degrees. In another embodiment, Form A is further characterized by a peak at about 10.0 degrees. In another embodiment, Form A is further characterized by a peak at 4.8 to 5.2 degrees. In another embodiment, Form A is further characterized by a peak at about 5.0 degrees. In another embodiment, Form A is further characterized by a peak at 24.0 to 24.4 degrees. In another embodiment, Form A is further characterized by a peak at about 24.2 degrees. In another embodiment, Form A is further characterized by a peak at 18.3 to 18.7 degrees. In another embodiment, Form A is further characterized by a peak at about 18.5 degrees.

Figure 4:
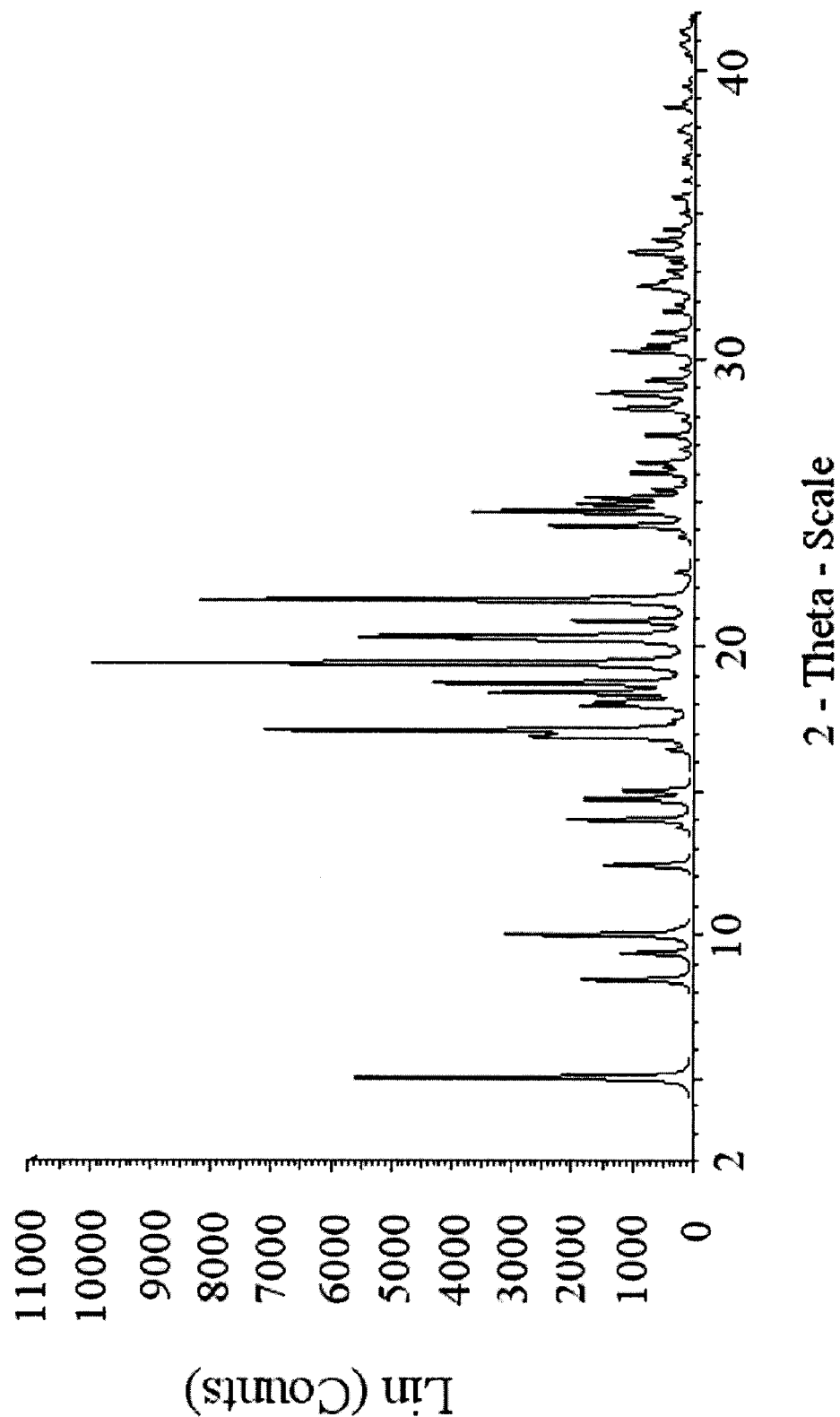
FIG. 4 is an X-ray powder diffraction pattern calculated from a single crystal of Compound 1 Form A.

In another embodiment, Form A is characterized by a diffraction pattern substantially similar to that of FIG. 4. In another embodiment, Form A is characterized by a diffraction pattern substantially similar to that of FIG. 5.

In another aspect, the invention features a crystal form of (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide having a monoclinic crystal system, a C2 space group, and the following unit cell dimensions: a=21.0952(16) Å, α=90°, b=6.6287 (5) Å, β=95.867(6)°, c=17.7917(15) Å, and γ=90°.

In another aspect, the invention features a pharmaceutical composition comprising Form A and a pharmaceutically acceptable carrier. In another embodiment, the pharmaceutical composition further comprises an additional therapeutic agent. In another embodiment, the additional therapeutic agent is selected from a mucolytic agent, bronchodialator, an anti-biotic, an anti-infective agent, an anti-inflammatory agent, a CFTR potentiator, or a nutritional agent.

In another aspect, the invention features a process of preparing Form A comprising slurrying (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl) cyclopropanecarboxamide in a solvent for an effective amount of time. In another embodiment, the solvent is ethyl acetate, dichloromethane, MTBE, isopropyl acetate, water/ethanol, water/acetonitrile, water/methanol, or water/isopropyl alcohol. In another embodiment, the effective amount of time is 24 hours to 2 weeks. In another embodiment, the effective amount of time is 24 hours to 1 week. In another embodiment, the effective amount of time is 24 hours to 72 hours.

In another aspect, the invention features a process of preparing Form A comprising dissolving (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl) cyclopropanecarboxamide in a solvent and evaporating the solvent. In another embodiment, the solvent is acetone, acetonitrile, methanol, or isopropyl alcohol.

In another aspect, the invention features a process of preparing Form A comprising dissolving (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl) cyclopropanecarboxamide in a first solvent and adding a second solvent that (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide is not soluble in. In another embodiment, the first solvent is ethyl acetate, ethanol, isopropyl alcohol, or acetone. In another embodiment, the second solvent is heptane or water. In another embodiment, the addition of the second solvent is done while stirring the solution of the first solvent and (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide.

In another aspect, the invention features a solid substantially amorphous (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl) cyclopropanecarboxamide. In another embodiment, the amorphous (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide comprises less than about 5% crystalline (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl) cyclopropanecarboxamide.

In another aspect, the invention features a pharmaceutical composition comprising the amorphous (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide and a pharmaceutically acceptable carrier. In another embodiment, the pharmaceutical composition further comprises an additional therapeutic agent. In another embodiment, the additional therapeutic agent is selected from a mucolytic agent, bronchodialator, an anti-biotic, an anti-infective agent, an anti-inflammatory agent, a CFTR potentiator, or a nutritional agent.

In another aspect, the invention features a process of preparing the amorphous (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide comprising dissolving (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide in a suitable solvent and removing the solvent by rotary evaporation. In another embodiment, the solvent is methanol.

In another aspect, the invention features a solid dispersion comprising the amorphous (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide and a polymer. In another embodiment, the polymer is hydroxypropylmethylcellulose (HPMC). In another embodiment, the polymer is hydroxypropylmethylcellulose acetate succinate (HPMCAS).

In another embodiment, the polymer is present in an amount from 10% by weight to 80% by weight. In another embodiment, the polymer is present in an amount from 30% by weight to 60% by weight. In another embodiment, the polymer is present in an amount of about 49.5% by weight.

In another embodiment, the (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide is present in an amount from 10% by weight to 80% by weight. In another embodiment, the (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide is present in an amount from 30% by weight to 60% by weight. In another embodiment, the (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide is present in an amount of about 50% by weight.

In another embodiment, the solid dispersion further comprises a surfactant. In another embodiment, the surfactant is sodium lauryl sulfate. In another embodiment, the surfactant is present in an amount from 0.1% by weight to 5% by weight. In another embodiment, the surfactant is present in an amount of about 0.5% by weight.

In another embodiment, the polymer is hydroxypropylmethylcellulose acetate succinate (HPMCAS) in the amount of 49.5% by weight, the surfactant is sodium lauryl sulfate in the amount of 0.5% by weight, and the (R)-1-(2,2-difluorobenzo[d][1,3]dioxol-5-yl)-N-(1-(2,3-dihydroxypropyl)-6-fluoro-2-(1-hydroxy-2-methyl propan-2-yl)-1H-indol-5-yl)cyclopropanecarboxamide is present in the amount of 50% by weight.

In another aspect, the invention features a pharmaceutical composition comprising the solid dispersion and a pharmaceutically acceptable carrier. In another embodiment, the pharmaceutical composition further comprises an additional therapeutic agent. In another embodiment, the additional therapeutic agent is selected from a mucolytic agent, bronchodialator, an anti-biotic, an anti-infective agent, an anti-inflammatory agent, a CFTR potentiator, or a nutritional agent.

In another aspect, the invention features a process of preparing amorphous (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide comprising spray drying (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide.

In another embodiment, the process comprises combining (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide and a suitable solvent and then spray drying the mixture to obtain amorphous (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide. In another embodiment, the solvent is an alcohol. In another embodiment, the solvent is methanol.

In another embodiment, the process comprises: a) forming a mixture comprising (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide, a polymer, and a solvent; and b) spray drying the mixture to form a solid dispersion.

In another embodiment, the polymer is hydroxypropylmethylcellulose acetate succinate (HPMCAS). In another embodiment, the polymer is in an amount of from 10% by weight to 80% by weight of the solid dispersion. In another embodiment, the polymer is in an amount of about 49.5% by weight of the solid dispersion. In another embodiment, the solvent is methanol. In another embodiment, the mixture further comprises a surfactant. In another embodiment, the surfactant is sodium lauryl sulfate (SLS). In another embodiment, the surfactant is in an amount of from 0.1% by weight to 5% by weight of the solid dispersion. In another embodiment, the surfactant is in an amount of about 0.5% by weight of the solid dispersion.

In another embodiment, the polymer is hydroxypropylmethylcellulose acetate succinate (HPMCAS) in the amount of about 49.5% by weight of the solid dispersion, the solvent is methanol, and the mixture further comprises sodium lauryl sulfate in an amount of about 0.5% by weight of the solid dispersion.

In another aspect, the invention features a method of treating a CFTR mediated disease in a subject comprising administering to the subject an effective amount of Form A, the amorphous (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide, or the solid dispersion of amorphous (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide.

In another embodiment, the CFTR mediated disease is selected from cystic fibrosis, asthma, smoke induced COPD, chronic bronchitis, rhinosinusitis, constipation, pancreatitis, pancreatic insufficiency, male infertility caused by congenital bilateral absence of the vas deferens (CBAVD), mild pulmonary disease, idiopathic pancreatitis, allergic bronchopulmonary aspergillosis (ABPA), liver disease, hereditary emphysema, hereditary hemochromatosis, coagulation-fibrinolysis deficiencies, protein C deficiency, Type 1 hereditary angioedema, lipid processing deficiencies, familial hypercholesterolemia, Type 1 chylomicronemia, abetalipoproteinemia, lysosomal storage diseases, I-cell disease/pseudo-Hurler, mucopolysaccharidoses, Sandhof/Tay-Sachs, Crigler-Najjar type II, polyendocrinopathy/hyperinsulemia, Diabetes mellitus, Laron dwarfism, myleoperoxidase deficiency, primary hypoparathyroidism, melanoma, glycanosis CDG type 1, congenital hyperthyroidism, osteogenesis imperfecta, hereditary hypofibrinogenemia, ACT deficiency, Diabetes insipidus (DI), neurophyseal DI, neprogenic DI, Charcot-Marie Tooth syndrome, Perlizaeus-Merzbacher disease, neurodegenerative diseases, Alzheimer's disease, Parkinson's disease, amyotrophic lateral sclerosis, progressive supranuclear plasy, Pick's disease, several polyglutamine neurological disorders, Huntington's, spinocerebullar ataxia type 1, spinal and bulbar muscular atrophy, dentatorubal pallidoluysian, myotonic dystrophy, spongiform encephalopathies, hereditary Creutzfeldt-Jakob disease (due to prion protein processing defect), Fabry disease, Straussler-Scheinker syndrome, COPD, dry-eye disease, Sjogren's disease, Osteoporosis, Osteopenia, Gorham's Syndrome, chloride channelopathies, myotonia congenita (Thomson and Becker forms), Bartter's syndrome type III, Dent's disease, hyperekplexia, epilepsy, hyperekplexia, lysosomal storage disease, Angelman syndrome, Primary Ciliary Dyskinesia (PCD), inherited disorders of the structure and/or function of cilia, PCD with situs inversus (also known as Kartagener syndrome), PCD without situs inversus, or ciliary aplasia. In another embodiment, the CFTR mediated disease is cystic fibrosis. In another embodiment, the subject has cystic fibrosis transmembrane receptor (CFTR) with a ΔF508 mutation. In another embodiment, the subject has cystic fibrosis transmembrane receptor (CFTR) with a R117H mutation. In another embodiment, the subject has cystic fibrosis transmembrane receptor (CFTR) with a G551D mutation.

In another embodiment, the method comprises administering an additional therapeutic agent. In another embodiment, the therapeutic agent is selected from a mucolytic agent, bronchodialator, an anti-biotic, an anti-infective agent, an anti-inflammatory agent, a CFTR potentiator, or a nutritional agent.

In another aspect, the invention features a kit comprising Form A, the amorphous (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide, or the solid dispersion comprising amorphous (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide, and instructions for use thereof.

Methods of Preparing Compound 1 Form A and Amorphous Form

Compound 1 is the starting point and in one embodiment can be prepared by coupling an acid chloride moiety with an amine moiety according to Schemes 1-4.

Scheme 1. Synthesis of the acid chloride moiety.

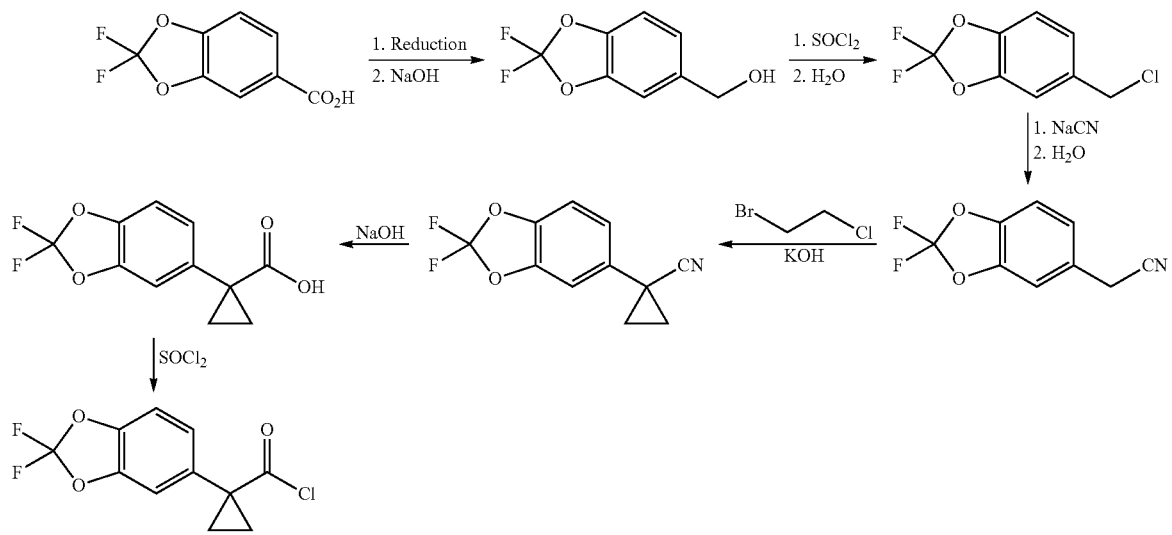

Scheme 2. Alternative synthesis of the acid chloride moiety.

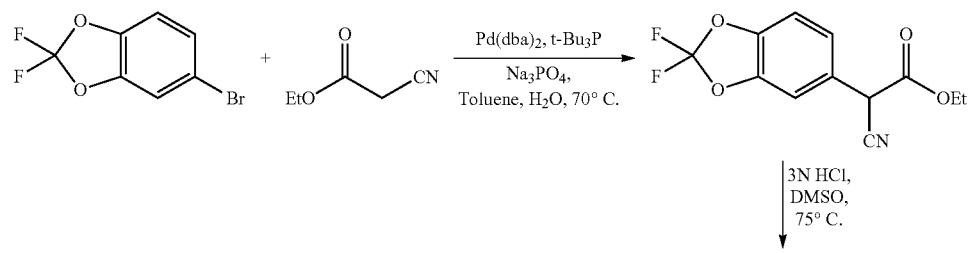

-continued
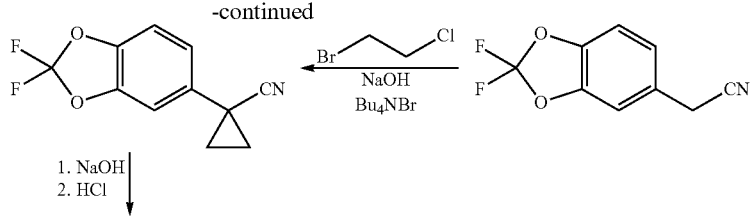
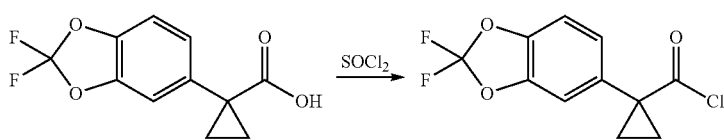
-continued
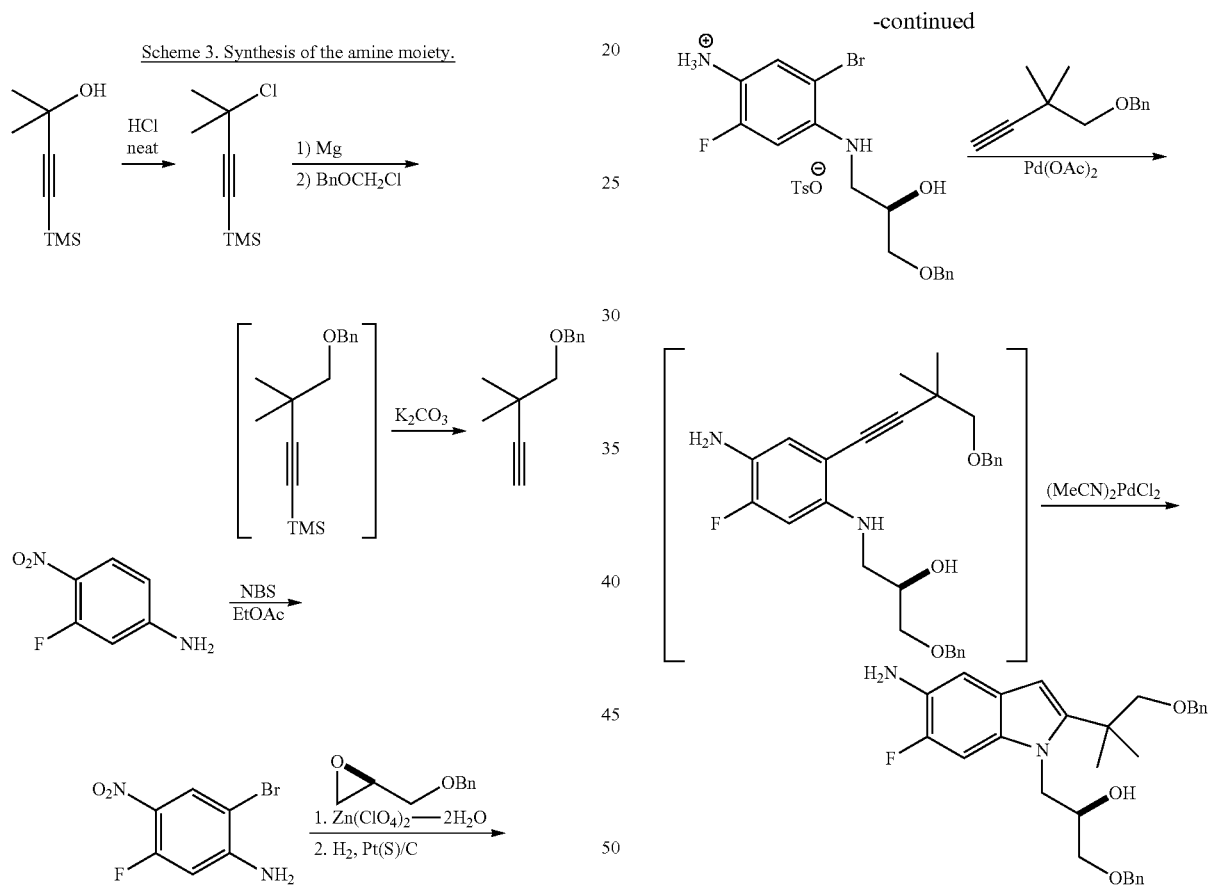
Scheme 3. Synthesis of the amine moiety.
Scheme 4. Formation of Compound 1.
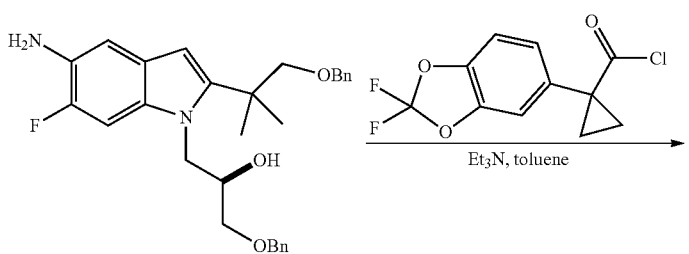

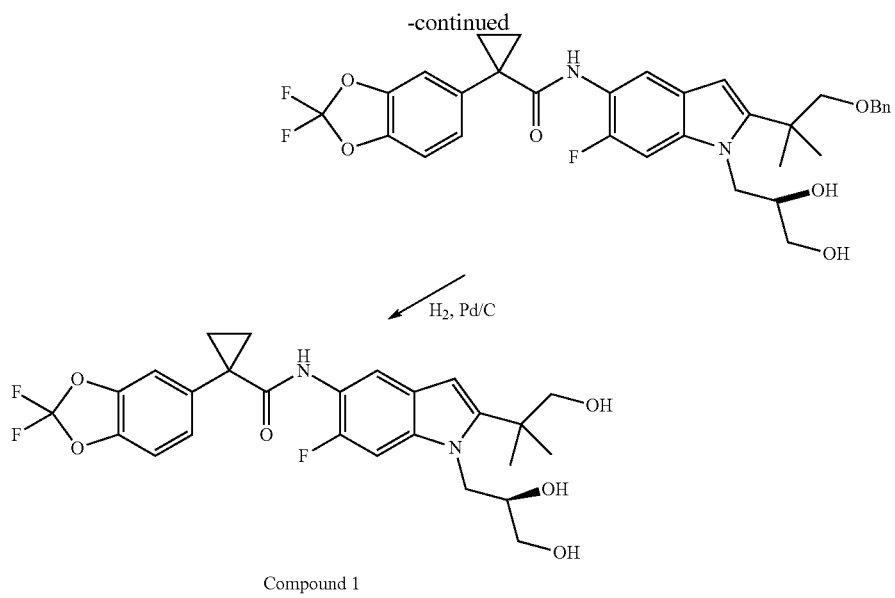

Compound 1

Methods for Forming Compound 1 Form A

In one embodiment, Form A is prepared by slurrying Compound 1 in an appropriate solvent for an effective amount of time. In another embodiment, the appropriate solvent is ethyl acetate, dichloromethane, MTBE, isopropyl acetate, various ratios of water/ethanol solutions, various ratios of water/acetonitrile solutions, various ratios of water/methanol solutions, or various ratios of water/isopropyl alcohol solutions. For example, various ratios of water/ethanol solutions include water/ethanol 1:9 (vol/vol), water/ethanol 1:1 (vol/vol), and water/ethanol 9:1 (vol/vol). Various ratios of water/acetonitrile solutions include water/acetonitrile 1:9 (vol/vol), water/acetonitrile 1:1 (vol/vol), and water/acetonitrile 9:1 (vol/vol). Various ratios of water/methanol solutions include water/methanol 1:9 (vol/vol), water/methanol 1:1 (vol/vol), and water/methanol 9:1 (vol/vol). Various ratios of water/isopropyl alcohol solutions include water/isopropyl alcohol 1:9 (vol/vol), water/isopropyl alcohol 1:1 (vol/vol), and water/isopropyl alcohol 9:1 (vol/vol).

Generally, about 40 mg of Compound 1 is slurred in about 1.5 ml of an appropriate solvent (target concentration at 26.7 mg/ml) at room temperature for an effective amount of time. In some embodiments, the effective amount of time is about 24 hours to about 2 weeks. In some embodiments, the effective amount of time is about 24 hours to about 1 week. In some embodiments, the effective amount of time is about 24 hours to about 72 hours. The solids are then collected.

In another embodiment, Form A is prepared by dissolving Compound 1 in an appropriate solvent and then evaporating the solvent. In one embodiment, the appropriate solvent is one in which Compound 1 has a solubility of greater than 20 mg/ml. For example, these solvents include acetonitrile, methanol, ethanol, isopropyl alcohol, acetone, and the like.

Generally, Compound 1 is dissolved in an appropriate solvent, filtered, and then left for either slow evaporation or fast evaporation. An example of slow evaporation is covering a container, such as a vial, comprising the Compound 1 solution with parafilm having one hole poked in it. An example of fast evaporation is leaving a container, such as a vial, comprising the Compound 1 solution uncovered. The solids are then collected.

In another aspect, the invention features a process of preparing Form A comprising dissolving Compound 1 in a first solvent and adding a second solvent that Compound 1 has poor solubility in (solubility<1 mg/ml). For example, the first solvent may be a solvent that Compound 1 has greater than 20 mg/ml solubility in, e.g. ethyl acetate, ethanol, isopropyl alcohol, or acetone. The second solvent may be, for example, heptane or water.

Generally, Compound 1 is dissolved in the first solvent and filtered to remove any seed crystals. The second solvent is added slowly while stirring. The solids are precipitated and collected by filtering.

Methods of Preparing Amorphous Compound 1

Starting from Compound 1 or Compound 1 Form A, the amorphous form of Compound 1 may be prepared by rotary evaporation or by spray dry methods.

Dissolving Compound 1 in an appropriate solvent like methanol and rotary evaporating the methanol to leave a foam produces Compound 1 amorphous form. In some embodiments, a warm water bath is used to expedite the evaporation.

Compound 1 amorphous form may also be prepared from Compound 1 Form A using spray dry methods. Spray drying is a process that converts a liquid feed to a dried particulate form. Optionally, a secondary drying process such as fluidized bed drying or vacuum drying, may be used to reduce residual solvents to pharmaceutically acceptable levels. Typically, spray drying involves contacting a highly dispersed liquid suspension or solution, and a sufficient volume of hot air to produce evaporation and drying of the liquid droplets. The preparation to be spray dried can be any solution, coarse suspension, slurry, colloidal dispersion, or paste that may be atomized using the selected spray drying apparatus. In a standard procedure, the preparation is sprayed into a current of warm filtered air that evaporates the solvent and conveys the dried product to a collector (e.g. a cyclone). The spent air is then exhausted with the solvent, or alternatively the spent air is sent to a condenser to capture and potentially recycle the solvent. Commercially available types of apparatus may be used to conduct the spray drying. For example, commercial spray dryers are manufactured by Buchi Ltd. And Niro (e.g., the PSD line of spray driers manufactured by Niro) (see, US 2004/0105820; US 2003/0144257).

Spray drying typically employs solid loads of material from about 3% to about 30% by weight, (i.e., drug and excipients), for example about 4% to about 20% by weight, preferably at least about 10%. In general, the upper limit of solid loads is governed by the viscosity of (e.g., the ability to pump) the resulting solution and the solubility of the components in the solution. Generally, the viscosity of the solution can determine the size of the particle in the resulting powder product.

Techniques and methods for spray drying may be found in Perry's Chemical Engineering Handbook, 6$^{th}$ Ed., R. H. Perry, D. W. Green & J. O. Maloney, eds.), McGraw-Hill book co. (1984); and Marshall "Atomization and Spray-Drying" 50, Chem. Eng. Prog. Monogr. Series 2 (1954). In general, the spray drying is conducted with an inlet temperature of from about 60° C. to about 200° C., for example, from about 95° C. to about 185° C., from about 110° C. to about 182° C., from about 96° C. to about 180° C., e.g., about 145° C. The spray drying is generally conducted with an outlet temperature of from about 30° C. to about 90° C., for example from about 40° C. to about 80° C., about 45° C. to about 80° C. e.g., about 75° C. The atomization flow rate is generally from about 4 kg/h to about 12 kg/h, for example, from about 4.3 kg/h to about 10.5 kg/h, e.g., about 6 kg/h or about 10.5 kg/h. The feed flow rate is generally from about 3 kg/h to about 10 kg/h, for example, from about 3.5 kg/h to about 9.0 kg/h, e.g., about 8 kg/h or about 7.1 kg/h. The atomization ratio is generally from about 0.3 to 1.7, e.g., from about 0.5 to 1.5, e.g., about 0.8 or about 1.5.

Removal of the solvent may require a subsequent drying step, such as tray drying, fluid bed drying (e.g., from about room temperature to about 100° C.), vacuum drying, microwave drying, rotary drum drying or biconical vacuum drying (e.g., from about room temperature to about 200° C.).

In one embodiment, the solid dispersion is fluid bed dried.

In one process, the solvent includes a volatile solvent, for example a solvent having a boiling point of less than about 100° C. In some embodiments, the solvent includes a mixture of solvents, for example a mixture of volatile solvents or a mixture of volatile and non-volatile solvents. Where mixtures of solvents are used, the mixture can include one or more non-volatile solvents, for example, where the non-volatile solvent is present in the mixture at less than about 15%, e.g., less than about 12%, less than about 10%, less than about 8%, less than about 5%, less than about 3%, or less than about 2%.

Preferred solvents are those solvents where Compound 1 has a solubility of at least about 10 mg/ml, (e.g., at least about 15 mg/ml, 20 mg/ml, 25 mg/ml, 30 mg/ml, 35 mg/ml, 40 mg/ml, 45 mg/ml, 50 mg/ml, or greater). More preferred solvents include those where Compound 1 has a solubility of at least about 20 mg/ml.

Exemplary solvents that could be tested include acetone, cyclohexane, dichloromethane, N,N-dimethylacetamide (DMA), N,N-dimethylformamide (DMF), 1,3-dimethyl-2-imidazolidinone (DMI), dimethyl sulfoxide (DMSO), dioxane, ethyl acetate, ethyl ether, glacial acetic acid (HAc), methyl ethyl ketone (MEK), N-methyl-2-pyrrolidinone (NMP), methyl tert-butyl ether (MTBE), tetrahydrofuran (THF), pentane, acetonitrile, methanol, ethanol, isopropyl alcohol, isopropyl acetate, and toluene. Exemplary co-solvents include acetone/DMSO, acetone/DMF, acetone/water, MEK/water, THF/water, dioxane/water. In a two solvent system, the solvents can be present in of from about 0.1% to about 99.9%. In some preferred embodiments, water is a co-solvent with acetone where water is present from about 0.1% to about 15%, for example about 9% to about 11%, e.g., about 10%. In some preferred embodiments, water is a co-solvent with MEK where water is present from about 0.1% to about 15%, for example about 9% to about 11%, e.g., about 10%. In some embodiments the solvent solution include three solvents. For example, acetone and water can be mixed with a third solvent such as DMA, DMF, DMI, DMSO, or HAc. In instances where amorphous Compound 1 is a component of a solid amorphous dispersion, preferred solvents dissolve both Compound 1 and the polymer. Suitable solvents include those described above, for example, MEK, acetone, water, methanol, and mixtures thereof.

The particle size and the temperature drying range may be modified to prepare an optimal solid dispersion. As would be appreciated by skilled practitioners, a small particle size would lead to improved solvent removal. Applicants have found however, that smaller particles can lead to fluffy particles that, under some circumstances do not provide optimal solid dispersions for downstream processing such as tabletting. At higher temperatures, crystallization or chemical degradation of Compound 1 may occur. At lower temperatures, a sufficient amount of the solvent may not be removed. The methods herein provide an optimal particle size and an optimal drying temperature.

In general, particle size is such that D10 (μm) is less than about 5, e.g., less than about 4.5, less than about 4.0, or less than about 3.5, D50 (μm) is generally less than about 17, e.g., less than about 16, less than about 15, less than about 14, less than about 13, and D90 (μm) is generally less than about 175, e.g., less than about 170, less than about 170, less than about 150, less than about 125, less than about 100, less than about 90, less than about 80, less than about 70, less than about 60, or less than about less than about 50. In general bulk density of the spray dried particles is from about 0.08 g/cc to about 0.20 g/cc, e.g., from about 0.10 to about 0.15 g/cc, e.g., about 0.11 g/cc or about 0.14 g/cc. Tap density of the spray dried particles generally ranges from about 0.08 g/cc to about 0.20 g/cc, e.g., from about 0.10 to about 0.15 g/cc, e.g., about 0.11 g/cc or about 0.14 g/cc, for 10 taps; 0.10 g/cc to about 0.25 g/cc, e.g., from about 0.11 to about 0.21 g/cc, e.g., about 0.15 g/cc, about 0.19 g/cc, or about 0.21 g/cc for 500 taps; 0.15 g/cc to about 0.27 g/cc, e.g., from about 0.18 to about 0.24 g/cc, e.g., about 0.18 g/cc, about 0.19 g/cc, about 0.20 g/cc, or about 0.24 g/cc for 1250 taps; and 0.15 g/cc to about 0.27 g/cc, e.g., from about 0.18 to about 0.24 g/cc, e.g., about 0.18 g/cc, about 0.21 g/cc, about 0.23 g/cc, or about 0.24 g/cc for 2500 taps.

Polymers

Solid dispersions including amorphous Compound 1 and a polymer (or solid state carrier) also are included herein. For example, Compound 1 is present as an amorphous compound as a component of a solid amorphous dispersion. The solid amorphous dispersion, generally includes Compound 1 and a polymer. Exemplary polymers include cellulosic polymers such as HPMC or HPMCAS and pyrrolidone containing polymers such as PVP/VA. In some embodiments, the solid amorphous dispersion includes one or more additional excipients, such as a surfactant.

In one embodiment, a polymer is able to dissolve in aqueous media. The solubility of the polymers may be pH-independent or pH-dependent. The latter include one or more enteric polymers. The term "enteric polymer" refers to a polymer that is preferentially soluble in the less acidic environment of the intestine relative to the more acid environment of the stomach, for example, a polymer that is insoluble in acidic aqueous media but soluble when the pH is above 5-6. An appropriate polymer should be chemically and biologically inert. In order to improve the physical stability of the solid dispersions, the glass transition temperature ($T_g$) of the polymer should be as high as possible. For example, preferred polymers have a glass transition temperature at least equal to or greater than the glass transition temperature of the drug (i.e., Compound 1). Other preferred polymers have a glass transition temperature that is within about 10 to about 15° C. of the drug (i.e., Compound 1). Examples of suitable glass transition temperatures of the polymers include at least about 90° C., at least about 95° C., at least about 100° C., at least about 105° C., at least about 110° C., at least about 115° C., at least about 120° C., at least about 125° C., at least about 130° C., at least about 135° C., at least about 140° C., at least about 145° C., at least about 150° C., at least about 155° C., at least about 160° C., at least about 165° C., at least about 170° C., or at least about 175° C. (as measured under dry conditions). Without wishing to be bound by theory, it is believed that the underlying mechanism is that a polymer with a higher $T_g$ generally has lower molecular mobility at room temperature, which can be a crucial factor in stabilizing the physical stability of the amorphous solid dispersion.

Additionally, the hygroscopicity of the polymers should be as low, e.g., less than about 10%. For the purpose of comparison in this application, the hygroscopicity of a polymer or composition is characterized at about 60% relative humidity. In some preferred embodiments, the polymer has less than about 10% water absorption, for example less than about 9%, less than about 8%, less than about 7%, less than about 6%, less than about 5%, less than about 4%, less than about 3%, or less than about 2% water absorption. The hygroscopicity can also affect the physical stability of the solid dispersions. Generally, moisture adsorbed in the polymers can greatly reduce the $T_g$ of the polymers as well as the resulting solid dispersions, which will further reduce the physical stability of the solid dispersions as described above.

In one embodiment, the polymer is one or more water-soluble polymer(s) or partially water-soluble polymer(s). Water-soluble or partially water-soluble polymers include but are not limited to, cellulose derivatives (e.g., hydroxypropylmethylcellulose (HPMC), hydroxypropylcellulose (HPC)) or ethylcellulose; polyvinylpyrrolidones (PVP); polyethylene glycols (PEG); polyvinyl alcohols (PVA); acrylates, such as polymethacrylate (e.g., Eudragit® E); cyclodextrins (e.g., β-cyclodextrin) and copolymers and derivatives thereof, including for example PVP-VA (polyvinylpyrollidone-vinyl acetate).

In some embodiments, the polymer is hydroxypropylmethylcellulose (HPMC), such as HPMC E50, HPMCE15, or HPMC60SH50).

As discussed herein, the polymer can be a pH-dependent enteric polymer. Such pH-dependent enteric polymers include, but are not limited to, cellulose derivatives (e.g., cellulose acetate phthalate (CAP)), hydroxypropyl methyl cellulose phthalates (HPMCP), hydroxypropyl methyl cellulose acetate succinate (HPMCAS), carboxymethylcellulose (CMC) or a salt thereof (e.g., a sodium salt such as (CMC-Na)); cellulose acetate trimellitate (CAT), hydroxypropylcellulose acetate phthalate (HPCAP), hydroxypropylmethylcellulose acetate phthalate (HPMCAP), and methylcellulose acetate phthalate (MCAP), or polymethacrylates (e.g., Eudragit® S). In some embodiments, the polymer is hydroxypropyl methyl cellulose acetate succinate (HPMCAS). In some embodiments, the polymer is hydroxypropyl methyl cellulose acetate succinate HG grade (HPMCAS-HG).

In yet another embodiment, the polymer is a polyvinylpyrrolidone co-polymer, for example, a vinylpyrrolidone/vinyl acetate co-polymer (PVP/VA).

In embodiments where Compound 1 forms a solid dispersion with a polymer, for example with an HPMC, HPMCAS, or PVP/VA polymer, the amount of polymer relative to the total weight of the solid dispersion ranges from about 0.1% to 99% by weight. Unless otherwise specified, percentages of drug, polymer and other excipients as described within a dispersion are given in weight percentages. The amount of polymer is typically at least about 20%, and preferably at least about 30%, for example, at least about 35%, at least about 40%, at least about 45%, or about 50% (e.g., 49.5%). The amount is typically about 99% or less, and preferably about 80% or less, for example about 75% or less, about 70% or less, about 65% or less, about 60% or less, or about 55% or less. In one embodiment, the polymer is in an amount of up to about 50% of the total weight of the dispersion (and even more specifically, between about 40% and 50%, such as about 49%, about 49.5%, or about 50%). HPMC and HPMCAS are available in a variety of grades from ShinEtsu, for example, HPMCAS is available in a number of varieties, including AS-LF, AS-MF, AS-HF, AS-LG, AS-MG, AS-HG. Each of these grades vary with the percent substitution of acetate and succinate.

In some embodiments, Compound 1 and polymer are present in roughly equal amounts, for example each of the polymer and the drug make up about half of the percentage weight of the dispersion. For example, the polymer is present in about 49.5% and the drug is present in about 50%.

In some embodiments, Compound 1 and the polymer combined represent 1% to 20% w/w total solid content of the non-solid dispersion prior to spray drying. In some embodiments, Compound 1 and the polymer combined represent 5% to 15% w/w total solid content of the non-solid dispersion prior to spray drying. In some embodiments, Compound 1 and the polymer combined represent about 11% w/w total solid content of the non-solid dispersion prior to spray drying.

In some embodiments, the dispersion further includes other minor ingredients, such as a surfactant (e.g., SLS). In some embodiments, the surfactant is present in less than about 10% of the dispersion, for example less than about 9%, less than about 8%, less than about 7%, less than about 6%, less than about 5%, less than about 4%, less than about 3%, less than about 2%, about 1%, or about 0.5%.

In embodiments including a polymer, the polymer should be present in an amount effective for stabilizing the solid dispersion. Stabilizing includes inhibiting or preventing, the crystallization of Compound 1. Such stabilizing would inhibit the conversion Compound 1 from amorphous to crystalline form. For example, the polymer would prevent at least a portion (e.g., about 5%, about 10%, about 15%, about 20%, about 25%, about 30%, about 35%, about 40%, about 45%, about 50%, about 55%, about 60%, about 65%, about 70%, about 75%, or greater) of Compound 1 from converting from an amorphous to a crystalline form. Stabilization can be measured, for example, by measuring the glass transition temperature of the solid dispersion, measuring the rate of relaxation of the amorphous material, or by measuring the solubility or bioavailability of Compound 1.

Suitable polymers for use in combination with Compound 1, for example to form a solid dispersion such as an amorphous solid dispersion, should have one or more of the following properties:

The glass transition temperature of the polymer should have a temperature of no less than about 10-15° C. lower than the glass transition temperature of Compound 1. Preferably, the glass transition temperature of the polymer is greater than the glass transition temperature of Compound 1, and in general at least 50° C. higher than the desired storage temperature of the drug product. For example, at least about 100° C., at least about 105° C., at least about 105° C., at least about 110°

C., at least about 120° C., at least about 130° C., at least about 140° C., at least about 150° C., at least about 160° C., at least about 160° C., or greater.

The polymer should be relatively non-hygroscopic. For example, the polymer should, when stored under standard conditions, absorb less than about 10% water, for example, less than about 9%, less than about 8%, less than about 7%, less than about 6%, or less than about 5%, less than about 4%, or less than about 3% water. Preferably the polymer will, when stored under standard conditions, be substantially free of absorbed water.

The polymer should have similar or better solubility in solvents suitable for spray drying processes relative to that of Compound 1. In preferred embodiments, the polymer will dissolve in one or more of the same solvents or solvent systems as Compound 1. It is preferred that the polymer is soluble in at least one non-hydroxy containing solvent such as methylene chloride, acetone, or a combination thereof.

The polymer, when combined with Compound 1, for example in a solid dispersion or in a liquid suspension, should increase the solubility of Compound 1 in aqueous and physiologically relative media either relative to the solubility of Compound 1 in the absence of polymer or relative to the solubility of Compound 1 when combined with a reference polymer. For example, the polymer could increase the solubility of amorphous Compound 1 by reducing the amount of amorphous Compound 1 that converts to crystalline Compound 1, either from a solid amorphous dispersion or from a liquid suspension.

The polymer should decrease the relaxation rate of the amorphous substance.

The polymer should increase the physical and/or chemical stability of Compound 1.

The polymer should improve the manufacturability of Compound 1.

The polymer should improve one or more of the handling, administration or storage properties of Compound 1.

The polymer should not interact unfavorably with other pharmaceutical components, for example excipients.

The suitability of a candidate polymer (or other component) can be tested using the spray drying methods (or other methods) described herein to form an amorphous composition. The candidate composition can be compared in terms of stability, resistance to the formation of crystals, or other properties, and compared to a reference preparation, e.g., a preparation of neat amorphous Compound 1 or crystalline Compound 1. For example, a candidate composition could be tested to determine whether it inhibits the time to onset of solvent mediated crystallization, or the percent conversion at a given time under controlled conditions, by at least 50%, 75%, 100%, or 110% as well as the reference preparation, or a candidate composition could be tested to determine if it has improved bioavailability or solubility relative to crystalline Compound 1.

Surfactants

A solid dispersion or other composition may include a surfactant. A surfactant or surfactant mixture would generally decrease the interfacial tension between the solid dispersion and an aqueous medium. An appropriate surfactant or surfactant mixture may also enhance aqueous solubility and bioavailability of Compound 1 from a solid dispersion. The surfactants for use in connection with the present invention include, but are not limited to, sorbitan fatty acid esters (e.g., Spans®), polyoxyethylene sorbitan fatty acid esters (e.g., Tweens®), sodium lauryl sulfate (SLS), sodium dodecylbenzene sulfonate (SDBS) dioctyl sodium sulfosuccinate (Docusate), dioxycholic acid sodium salt (DOSS), Sorbitan Monostearate, Sorbitan Tristearate, hexadecyltrimethyl ammonium bromide (HTAB), Sodium N-lauroylsarcosine, Sodium Oleate, Sodium Myristate, Sodium Stearate, Sodium Palmitate, Gelucire 44/14, ethylenediamine tetraacetic acid (EDTA), Vitamin E d-alpha tocopheryl polyethylene glycol 1000 succinate (TPGS), Lecithin, MW 677-692, Glutanic acid monosodium monohydrate, Labrasol, PEG 8 caprylic/capric glycerides, Transcutol, diethylene glycol monoethyl ether, Solutol HS-15, polyethylene glycol/hydroxystearate, Taurocholic Acid, Pluronic F68, Pluronic F 108, and Pluronic F127 (or any other polyoxyethylene-polyoxypropylene co-polymers (Pluronics®) or saturated polyglycolized glycerides (Gelucirs®)). Specific example of such surfactants that may be used in connection with this invention include, but are not limited to, Span 65, Span 25, Tween 20, Capryol 90, Pluronic F108, sodium lauryl sulfate (SLS), Vitamin E TPGS, pluronics and copolymers. SLS is generally preferred.

The amount of the surfactant (e.g., SLS) relative to the total weight of the solid dispersion may be between 0.1-15%. Preferably, it is from about 0.5% to about 10%, more preferably from about 0.5 to about 5%, e.g., about 0.5 to 4%, about 0.5 to 3%, about 0.5 to 2%, about 0.5 to 1%, or about 0.5%.

In certain embodiments, the amount of the surfactant relative to the total weight of the solid dispersion is at least about 0.1%, preferably about 0.5%. In these embodiments, the surfactant would be present in an amount of no more than about 15%, and preferably no more than about 12%, about 11%, about 10%, about 9%, about 8%, about 7%, about 6%, about 5%, about 4%, about 3%, about 2% or about 1%. An embodiment wherein the surfactant is in an amount of about 0.5% by weight is preferred.

Candidate surfactants (or other components) can be tested for suitability for use in the invention in a manner similar to that described for testing polymers.

Uses, Formulation and Administration

Pharmaceutically Acceptable Compositions

In another aspect of the present invention, pharmaceutically acceptable compositions are provided, wherein these compositions comprise Compound 1 Form A or amorphous Compound 1 as described herein, and optionally comprise a pharmaceutically acceptable carrier, adjuvant or vehicle. In certain embodiments, these compositions optionally further comprise one or more additional therapeutic agents.

As described above, the pharmaceutically acceptable compositions of the present invention additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention. Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Uses of Compounds and Pharmaceutically Acceptable Compositions

In yet another aspect, the present invention provides a method of treating a condition, disease, or disorder implicated by CFTR. In certain embodiments, the present invention provides a method of treating a condition, disease, or disorder implicated by a deficiency of CFTR activity, the method comprising administering a composition comprising a solid state form of Compound 1 Form A or amorphous Compound 1 described herein to a subject, preferably a mammal, in need thereof.

A "CFTR-mediated disease" as used herein is a disease selected from cystic fibrosis, asthma, smoke induced COPD, chronic bronchitis, rhinosinusitis, constipation, pancreatitis, pancreatic insufficiency, male infertility caused by congenital bilateral absence of the vas deferens (CBAVD), mild pulmonary disease; idiopathic pancreatitis, allergic bronchopulmonary aspergillosis (ABPA), liver disease, hereditary emphysema, hereditary hemochromatosis, coagulation-fibrinolysis deficiencies, protein C deficiency, Type 1 hereditary angioedema, lipid processing deficiencies, familial hypercholesterolemia, Type 1 chylomicronemia, abetalipoproteinemia, lysosomal storage diseases, I-cell disease/pseudo-Hurler, mucopolysaccharidoses, Sandhof/Tay-Sachs, Crigler-Najjar type II, polyendocrinopathy/hyperinsulemia, Diabetes mellitus, Laron dwarfism, myleoperoxidase deficiency, primary hypoparathyroidism, melanoma, glycanosis CDG type 1, congenital hyperthyroidism, osteogenesis imperfecta, hereditary hypofibrinogenemia, ACT deficiency, Diabetes insipidus (DI), neurophyseal DI, neprogenic DI, Charcot-Marie Tooth syndrome, Perlizaeus-Merzbacher disease, neurodegenerative diseases, Alzheimer's disease, Parkinson's disease, amyotrophic lateral sclerosis, progressive supranuclear plasy, Pick's disease, several polyglutamine neurological disorders, Huntington's, spinocerebullar ataxia type I, spinal and bulbar muscular atrophy, dentatorubal pallidoluysian, myotonic dystrophy, spongiform encephalopathies, hereditary Creutzfeldt-Jakob disease (due to prion protein processing defect), Fabry disease, Straussler-Scheinker syndrome, COPD, dry-eye disease, Sjogren's disease, Osteoporosis, Osteopenia, Gorham's Syndrome, chloride channelopathies, myotonia congenita (Thomson and Becker forms), Bartter's syndrome type III, Dent's disease, hyperekplexia, epilepsy, hyperekplexia, lysosomal storage disease, Angelman syndrome, Primary Ciliary Dyskinesia (PCD), inherited disorders of the structure and/or function of cilia, PCD with situs inversus (also known as Kartagener syndrome), PCD without situs inversus, or ciliary aplasia.

In certain embodiments, the present invention provides a method of treating a CFTR-mediated disease in a human comprising the step of administering to said human an effective amount of a composition comprising Compound 1 Form A or amorphous Compound 1 described herein.

According to an alternative preferred embodiment, the present invention provides a method of treating cystic fibrosis in a human comprising the step of administering to said human a composition comprising Compound 1 Form A or amorphous Compound 1 described herein.

According to the invention an "effective amount" of Compound 1 Form A or amorphous Compound 1 or a pharmaceutically acceptable composition thereof is that amount effective for treating or lessening the severity of any of the diseases recited above.

Compound 1 Form A or amorphous Compound 1 or a pharmaceutically acceptable composition thereof may be administered using any amount and any route of administration effective for treating or lessening the severity of one or more of the diseases recited above.

In certain embodiments, Compound 1 Form A or amorphous Compound 1 described herein or a pharmaceutically acceptable composition thereof is useful for treating or lessening the severity of cystic fibrosis in patients who exhibit residual CFTR activity in the apical membrane of respiratory and non-respiratory epithelia. The presence of residual CFTR activity at the epithelial surface can be readily detected using methods known in the art, e.g., standard electrophysiological, biochemical, or histochemical techniques. Such methods identify CFTR activity using in vivo or ex vivo electrophysiological techniques, measurement of sweat or salivary CF concentrations, or ex vivo biochemical or histochemical techniques to monitor cell surface density. Using such methods, residual CFTR activity can be readily detected in patients heterozygous or homozygous for a variety of different mutations, including patients homozygous or heterozygous for the most common mutation, ΔF508, as well as other mutations such as the G551D mutation, or the R117H mutation.

In one embodiment, Compound 1 Form A or amorphous Compound 1 described herein or a pharmaceutically acceptable composition thereof is useful for treating or lessening the severity of cystic fibrosis in patients within certain genotypes exhibiting residual CFTR activity, e.g., class III mutations (impaired regulation or gating), class IV mutations (altered conductance), or class V mutations (reduced synthesis) (Lee R. Choo-Kang, Pamela L., Zeitlin, *Type I, II, III, IV, and V cystic fibrosis Transmembrane Conductance Regulator Defects and Opportunities of Therapy*; Current Opinion in Pulmonary Medicine 6:521-529, 2000). Other patient genotypes that exhibit residual CFTR activity include patients homozygous for one of these classes or heterozygous with any other class of mutations, including class I mutations, class H mutations, or a mutation that lacks classification.

In one embodiment, Compound 1 Form A or amorphous Compound 1 described herein or a pharmaceutically acceptable composition thereof is useful for treating or lessening the severity of cystic fibrosis in patients within certain clinical phenotypes, e.g., a moderate to mild clinical phenotype that typically correlates with the amount of residual CFTR activity in the apical membrane of epithelia. Such phenotypes include patients exhibiting pancreatic insufficiency or patients diagnosed with idiopathic pancreatitis and congenital bilateral absence of the vas deferens, or mild lung disease.

The exact amount required will vary from subject to subject, depending on the species, age, and general condition of the subject, the severity of the infection, the particular agent, its mode of administration, and the like. The compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient" or "subject", as used herein, means an animal, preferably a mammal, and most preferably a human.

The pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

In certain embodiments, the dosage amount of Compound 1 Form A or amorphous Compound 1 in the dosage unit form is from 100 mg to 1,000 mg. In another embodiment, the dosage amount of Compound 1 Form A or amorphous Compound 1 is from 200 mg to 900 mg. In another embodiment, the dosage amount of Compound 1 Form A or amorphous Compound 1 is from 300 mg to 800 mg. In another embodiment, the dosage amount of Compound 1 Form A or amorphous Compound 1 is from 400 mg to 700 mg. In another embodiment, the dosage amount of Compound 1 Form A or amorphous Compound 1 is from 500 mg to 600 mg.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

The active compounds can also be in microencapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

It will also be appreciated that Compound 1 Form A or amorphous Compound 1 described herein or a pharmaceutically acceptable composition thereof can be employed in combination therapies, that is, Compound 1 Form A or amorphous Compound 1 can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another agent used to treat the same disorder), or they may achieve different effects (e.g., control of any adverse effects). As used herein, additional therapeutic agents that are normally administered to treat or prevent a particular disease, or condition, are known as "appropriate for the disease, or condition, being treated".

In one embodiment, the additional agent is selected from a mucolytic agent, bronchodialator, an anti-biotic, an anti-infective agent, an anti-inflammatory agent, a CFTR modulator other than a compound of the present invention, or a nutritional agent.

In one embodiment, the additional agent is 3-(6-(1-(2,2-difluorobenzo[d][1,3]dioxol-5-yl)cyclopropanecarboxamido)-3-methylpyridin-2-yl)benzoic acid. In another embodiment, the additional agent is N-(5-hydroxy-2,4-ditert-butyl-phenyl)-4-oxo-1H-quinoline-3-carboxamide. In another embodiment, the additional agent is selected from Table 1:

TABLE 1

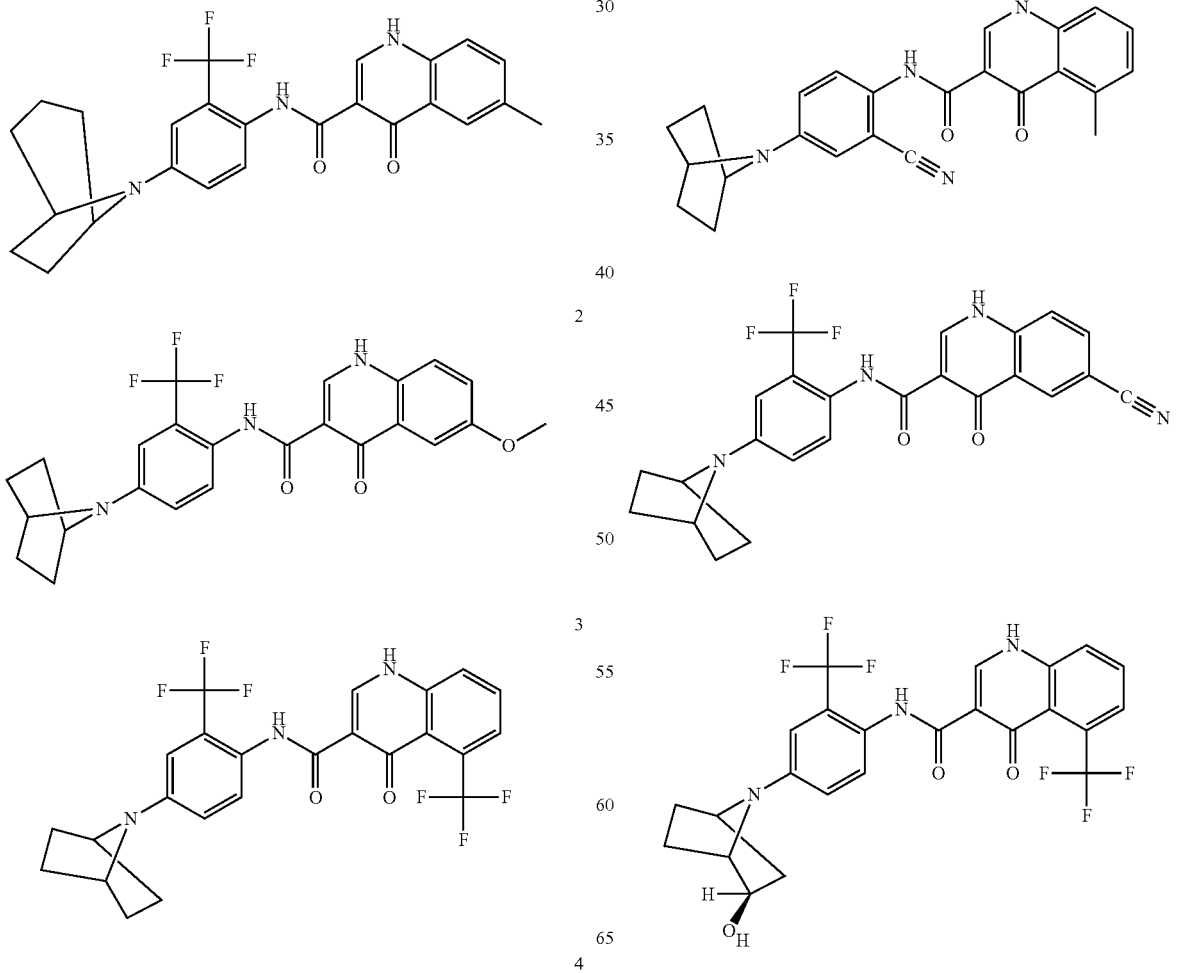

TABLE 1-continued

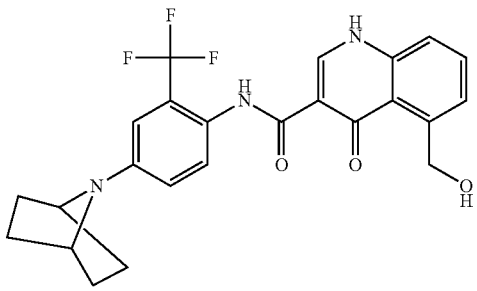 [SMILES: O=C(Nc1ccc(N2C3CCC2CC3)cc1C(F)(F)F)c1c[nH]c2cccc(CO)c2c1=O]

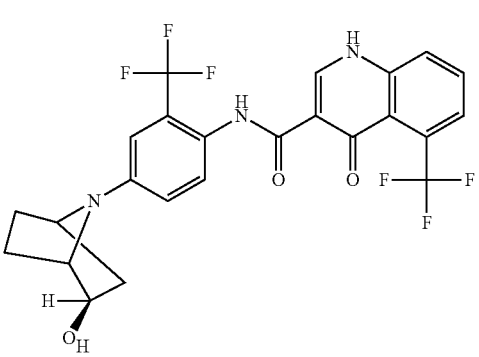

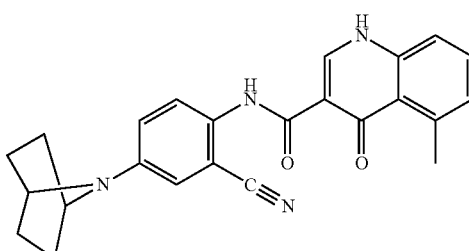

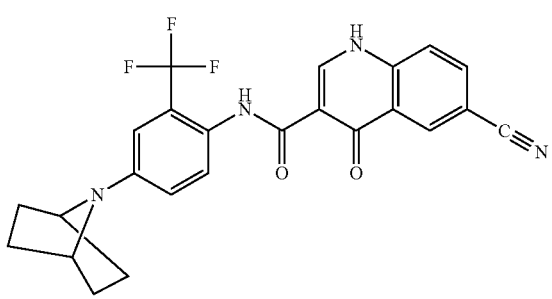 [SMILES: N#Cc1ccc2[nH]cc(C(=O)Nc3ccc(N4C5CCC4CC5)cc3C(F)(F)F)c(=O)c2c1]

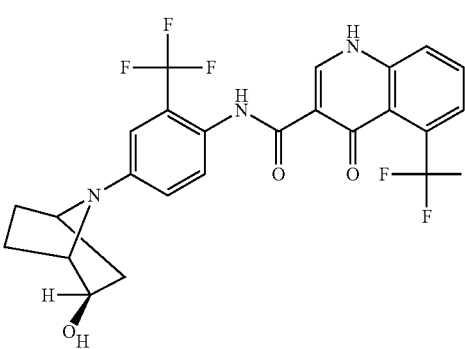

TABLE 1-continued

9
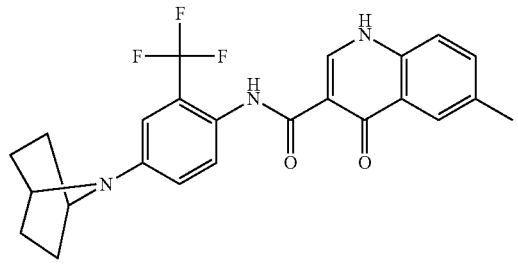 [SMILES: Cc1ccc2[nH]cc(C(=O)Nc3ccc(N4C5CCC4CC5)cc3C(F)(F)F)c(=O)c2c1]

10
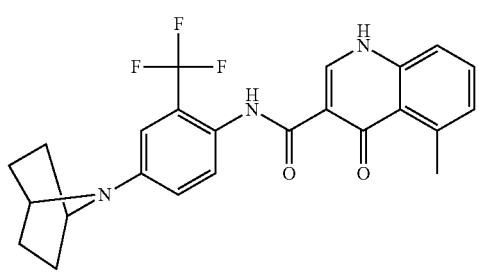 [SMILES: Cc1cccc2[nH]cc(C(=O)Nc3ccc(N4C5CCC4CC5)cc3C(F)(F)F)c(=O)c12]

11
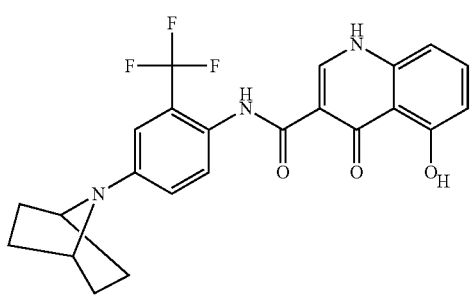

12
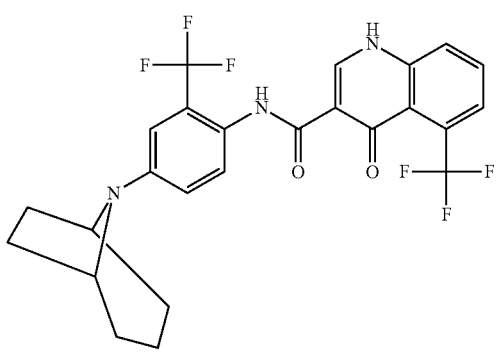 [SMILES: O=C(Nc1ccc(N2C3CCCC2CC3)cc1C(F)(F)F)c1c[nH]c2cccc(C(F)(F)F)c2c1=O]

13
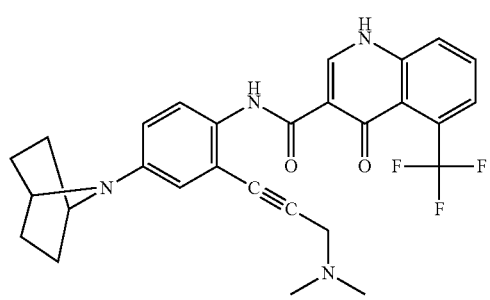 [SMILES: CN(C)CC#Cc1cc(N2C3CCC2CC3)ccc1NC(=O)c1c[nH]c2cccc(C(F)(F)F)c2c1=O]

TABLE 1-continued

14
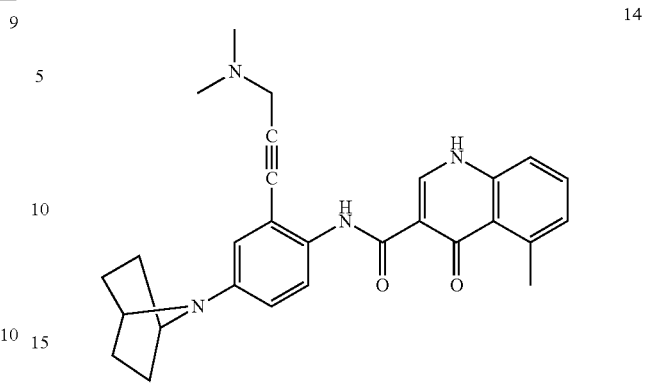

In another embodiment, the additional agent is any combination of the above agents. For example, the composition may comprise Compound 1,3-(6-(1-(2,2-difluorobenzo[d][1,3]dioxol-5-yl)cyclopropanecarboxamido)-3-methylpyridin-2-yl)benzoic acid, and N-(5-hydroxy-2,4-ditert-butyl-phenyl)-4-oxo-1H-quinoline-3-carboxamide. In another example, the composition may comprise Compound 1, N-(5-hydroxy-2,4-ditert-butyl-phenyl)-4-oxo-1H-quinoline-3-carboxamide, and any one of the compounds from Table 1, i.e. compounds 1 through 14 of Table 1, or any combination thereof.

In one embodiment, the additional therapeutic agent is an antibiotic. Exemplary antibiotics useful herein include tobramycin, including tobramycin inhaled powder (TIP), azithromycin, aztreonam, including the aerosolized form of aztreonam, amikacin, including liposomal formulations thereof, ciprofloxacin, including formulations thereof suitable for administration by inhalation, levoflaxacin, including aerosolized formulations thereof, and combinations of two antibiotics, e.g., fosfomycin and tobramycin.

In another embodiment, the additional agent is a mucolyte. Exemplary mucolytes useful herein includes Pulmozyme®.

In another embodiment, the additional agent is a bronchodialator. Exemplary bronchodilators include albuterol, metaprotenerol sulfate, pirbuterol acetate, salmeterol, or tetrabuline sulfate.

In another embodiment, the additional agent is effective in restoring lung airway surface liquid. Such agents improve the movement of salt in and out of cells, allowing mucus in the lung airway to be more hydrated and, therefore, cleared more easily. Exemplary such agents include hypertonic saline, denufosol tetrasodium ([[(3S,5R)-5-(4-amino-2-oxopyrimidin-1-yl)-3-hydroxyoxolan-2-yl]methoxy-hydroxyphosphoryl] [[[(2R,3S,4R,5R)-5-(2,4-dioxopyrimidin-1-yl)-3,4-dihydroxyoxolan-2-yl]methoxy-hydroxyphosphoryl]oxy-hydroxyphosphoryl]hydrogen phosphate), or bronchitol (inhaled formulation of mannitol).

In another embodiment, the additional agent is an anti-inflammatory agent, i.e., an agent that can reduce the inflammation in the lungs. Exemplary such agents useful herein include ibuprofen, docosahexanoic acid (DHA), sildenafil, inhaled glutathione, pioglitazone, hydroxychloroquine, or simavastatin.

In another embodiment, the additional agent is a CFTR modulator other than Compound 1 Form I, i.e., an agent that has the effect of modulating CFTR activity. Exemplary such agents include ataluren ("PTC124®"; 3-[5-(2-fluorophenyl)-1,2,4-oxadiazol-3-yl]benzoic acid), sinapultide, lancovutide, depelestat (a human recombinant neutrophil elastase inhibitor), cobiprostone (7-{(2R,4aR,5R,7aR)-2-[(3S)-1,1-difluoro-3-methylpentyl]-2-hydroxy-6-oxooctahydrocyclopenta[b]pyran-5-yl}heptanoic acid), and N-(5-hydroxy-2,4-ditert-butyl-phenyl)-4-oxo-1H-quinoline-3-carboxamide.

In another embodiment, the additional agent is a nutritional agent. Exemplary nutritional agents include pancrelipase (pancreating enzyme replacement), including Pancrease®, Pancreacarb®, Ultrase®, or Creon®, Liprotomase® (formerly Trizytek®), Aquadeks®, or glutathione inhalation. In one embodiment, the additional nutritional agent is pancrelipase.

In another embodiment, the additional agent is a compound selected from gentamicin, curcumin, cyclophosphamide, 4-phenylbutyrate, miglustat, felodipine, nimodipine, Philoxin B, geniestein, Apigenin, cAMP/cGMP modulators such as rolipram, sildenafil, milrinone, tadalafil, amrinone, isoproterenol, albuterol, and almeterol, deoxyspergualin, HSP 90 inhibitors, HSP 70 inhibitors, proteosome inhibitors such as epoxomicin, lactacystin, etc.

In another embodiment, the additional agent is a compound disclosed in WO 2004028480, WO 2004110352, WO 2005094374, WO 2005120497, or WO 2006101740.

In another embodiment, the additional agent is a benzo[c]quinolizinium derivative that exhibits CFTR modulation activity or a benzopyran derivative that exhibits CFTR modulation activity.

In another embodiment, the additional agent is a compound disclosed in U.S. Pat. No. 7,202,262, U.S. Pat. No. 6,992,096, US20060148864, US20060148863, US20060035943, US20050164973, WO2006110483, WO2006044456, WO2006044682, WO2006044505, WO2006044503, WO2006044502, or WO2004091502.

In another embodiment, the additional agent is a compound disclosed in WO2004080972, WO2004111014, WO2005035514, WO2005049018, WO2006099256, WO2006127588, or WO2007044560.

These combinations are useful for treating the diseases described herein including cystic fibrosis. These combinations are also useful in the kits described herein.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

Compound 1 Form A and amorphous form described herein or a pharmaceutically acceptable composition thereof may also be incorporated into compositions for coating an implantable medical device, such as prostheses, artificial valves, vascular grafts, stents and catheters. Accordingly, the present invention, in another aspect, includes a composition for coating an implantable device comprising Compound 1 Form A and/or amorphous form described herein or a pharmaceutically acceptable composition thereof, and in classes and subclasses herein, and a carrier suitable for coating said implantable device. In still another aspect, the present invention includes an implantable device coated with a composition comprising Compound 1 Form A and/or amorphous form described herein or a pharmaceutically acceptable composition thereof, and a carrier suitable for coating said implantable device. Suitable coatings and the general preparation of coated implantable devices are described in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccharides, polyethylene glycol, phospholipids or combinations thereof to impart controlled release characteristics in the composition.

In order that the invention described herein may be more fully understood, the following examples are set forth. It should be understood that these examples are for illustrative purposes only and are not to be construed as limiting this invention in any manner.

EXAMPLES

Methods & Materials

Modulated Differential Scanning Calorimetry (MDSC) and Differential Scanning Calorimetry (DSC)

The modulated differential scanning calorimetry (MDSC) was used for testing the glass transition temperature of the amorphous form and spray dried dispersion of a compound. Differential scanning calorimetry (DSC) was used to determine the melting point of crystalline materials and to discriminate between different polymorphs. The data were collected using a TA DSC Q2000 differential scanning calorimeter (TA Instruments, New Castle, Del.). The instrument was calibrated with indium. Samples of approximately 1-5 mg were weighed into aluminum hermetic pans that were crimped using lids with one hole. For MDSC the samples were scanned from −20° C. to 220° C. at 2° C./minute heating rate with +/−1° C. modulation every 60 seconds. For DSC the samples were scanned from 25° C. to 220° C. at a heating rate of 10° C./min. Data were collected by Thermal Advantage Q Series™ software (version: 2.7.0.380) and analyzed by Universal Analysis software (version: 4.4A, build: 4.4.0.5) (TA Instruments, New Castle, Del.).

XRPD (X-ray Powder Diffraction)

X-ray Powder Diffraction was used to characterize the physical form of the lots produced to date and to characterize different polymorphs identified. The XRPD data of a compound were collected on a PANalytical X'pert Pro Powder X-ray Diffractometer (Almelo, the Netherlands). The XRPD pattern was recorded at room temperature with copper radiation (1.54060 A). The X-ray was generated using Cu sealed tube at 45 kV, 40 mA with a Nickel Kβ suppression filter. The incident beam optic was comprised of a variable divergence slit to ensure a constant illuminated length on the sample and on the diffracted beam side; a fast linear solid state detector was used with an active length of 2.12 degrees 2 theta measured in a scanning mode. The powder sample was packed on the indented area of a zero background silicon holder and spinning was performed to achieve better statistics. A symmetrical scan was measured from 4-40 degrees 2 theta with a step size of 0.017 degrees and a scan step time of 15.5 seconds. The data collection software is X'pert Data Collector (version 2.2e). The data analysis software is either X'pert Data Viewer (version 1.2d) or X'pert Highscore (version: 2.2c).

Thermogravimetric Analysis (TGA)

TGA was used to investigate the presence of residual solvents in the lots characterized, and identify the temperature at which decomposition of the sample occurs. TGA data were collected on a TA Q500 Thermogravimetric Analyzer (TA Instruments, New Castle, Del.). A sample with weight of approximately 2-5 mg was scanned from 25° C. to 300° C. at a heating rate of 10° C./min. Data were collected by Thermal Advantage Q Series™ software (version 2.5.0.255) and analyzed by Universal Analysis software (version 4.4A, build 4.4.0.5) (TA Instruments, New Castle, Del.).

Compound 1 Form A Single Crystal Structure Determination

Diffraction data were acquired on Bruker Apex II diffractometer equipped with sealed tube Cu Kα source and an Apex II CCD detector. The structure was solved and refined using SHELX program (Sheldrick, G. M., Acta Cryst., (2008) A64, 112-122). Based on intensities statistics and systematic absences the structure was solved and refined in C2 space group. The absolute configuration was determined using anomalous diffraction. Flack parameter refined to 0.00 (18) indicating that the model represent the correct enantiomer [(R)].

Solid State NMR

Solid state NMR was conducted on a Bruker-Biospin 400 MHz wide-bore spectrometer equipped with a Bruker-Biospin 4 mm HFX probe. Samples were packed into 4 mm $ZrO_2$ rotors and spun under Magic Angle Spinning (MAS) condition with spinning speed of 12.5 kHz. The proton relaxation time was first measured using $^1H$ MAS $T_1$ saturation recovery relaxation experiment in order to set up proper recycle delay of the $^{13}C$ cross-polarization (CP) MAS experiment. The CP contact time of carbon CPMAS experiment was set to 2 ms. A CP proton pulse with linear ramp (from 50% to 100%) was employed. The Hartmann-Hahn match was optimized on external reference sample (glycine). The fluorine MAS spectrum was recorded with proton decoupling. TPPM15 decoupling sequence was used with the field strength of approximately 100 kHz for both $^{13}C$ and $^{19}F$ acquisitions.

Vitride® (sodium bis(2-methoxyethoxy)aluminum hydride [or $NaAlH_2(OCH_2CH_2OCH_3)_2$], 65 wgt % solution in toluene) was purchased from Aldrich Chemicals.

2,2-Difluoro-1,3-benzodioxole-5-carboxylic acid was purchased from Saltigo (an affiliate of the Lanxess Corporation).

Anywhere in the present application where a name of a compound may not correctly describe the structure of the compound, the structure supersedes the name and governs.

Synthesis of Compound 1

Acid Moiety

Synthesis of (2,2-difluoro-1,3-benzodioxol-5-yl)-methanol

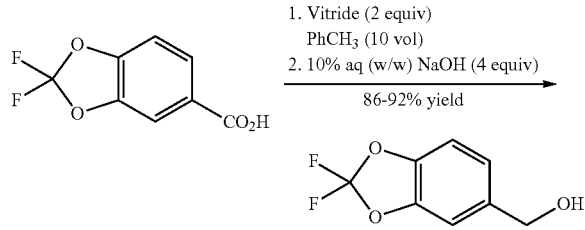

Commercially available 2,2-difluoro-1,3-benzodioxole-5-carboxylic acid (1.0 eq) is slurried in toluene (10 vol). Vitride® (2 eq) is added via addition funnel at a rate to maintain the temperature at 15-25° C. At the end of addition the temperature is increased to 40° C. for 2 h then 10% (w/w) aq. NaOH (4.0 eq) is carefully via addition funnel maintaining the temperature at 40-50° C. After stirring for an additional 30 minutes, the layers are allowed to separate at 40° C. The organic phase is cooled to 20° C. then washed with water (2×1.5 vol), dried ($Na_2SO_4$), filtered, and concentrated to afford crude (2,2-difluoro-1,3-benzodioxol-5-yl)-methanol that is used directly in the next step.

Synthesis of 5-chloromethyl-2,2-difluoro-1,3-benzodioxole

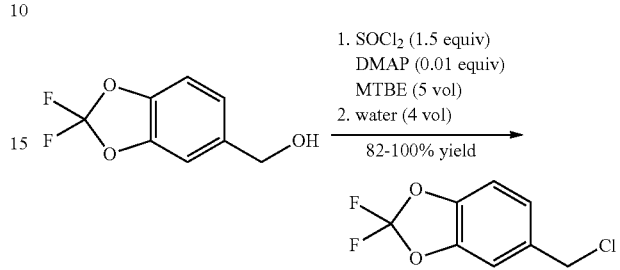

(2,2-difluoro-1,3-benzodioxol-5-yl)-methanol (1.0 eq) is dissolved in MTBE (5 vol). A catalytic amount of DMAP (1 mol %) is added and $SOCl_2$ (1.2 eq) is added via addition funnel. The $SOCl_2$ is added at a rate to maintain the temperature in the reactor at 15-25° C. The temperature is increased to 30° C. for 1 hour then cooled to 20° C. then water (4 vol) is added via addition funnel maintaining the temperature at less than 30° C. After stirring for an additional 30 minutes, the layers are allowed to separate. The organic layer is stirred and 10% (w/v) aq. NaOH (4.4 vol) is added. After stirring for 15 to 20 minutes, the layers are allowed to separate. The organic phase is then dried ($Na_2SO_4$), filtered, and concentrated to afford crude 5-chloromethyl-2,2-difluoro-1,3-benzodioxole that is used directly in the next step.

Synthesis of (2,2-difluoro-1,3-benzodioxol-5-yl)-acetonitrile

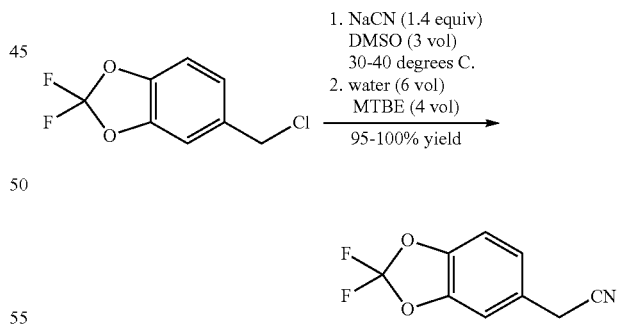

A solution of 5-chloromethyl-2,2-difluoro-1,3-benzodioxole (1 eq) in DMSO (1.25 vol) is added to a slurry of NaCN (1.4 eq) in DMSO (3 vol) maintaining the temperature between 30-40° C. The mixture is stirred for 1 hour then water (6 vol) is added followed by MTBE (4 vol). After stirring for 30 min, the layers are separated. The aqueous layer is extracted with MTBE (1.8 vol). The combined organic layers are washed with water (1.8 vol), dried ($Na_2SO_4$), filtered, and concentrated to afford crude (2,2-difluoro-1,3-benzodioxol-5-yl)-acetonitrile (95%) that is used directly in the next step.

$^1$H NMR (500 MHz, DMSO) δ 7.44 (br s, 1H), 7.43 (d, J=8.4 Hz, 1H), 7.22 (dd, J=8.2, 1.8 Hz, 1H), 4.07 (s, 2H).

Synthesis of (2,2-difluoro-1,3-benzodioxol-5-yl)-1-ethylacetate-acetonitrile

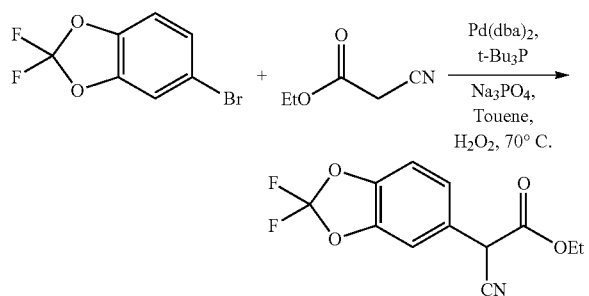

A reactor was purged with nitrogen and charged with 900 mL of toluene. The solvent was degassed via nitrogen sparge for no less than 16 h. To the reactor was then charged Na$_3$PO$_4$ (155.7 g, 949.5 mmol), followed by bis(dibenzylideneacetone) palladium (0) (7.28 g, 12.66 mmol). A 10% w/w solution of tert-butylphosphine in hexanes (51.23 g, 25.32 mmol) was charged over 10 min at 23° C. from a nitrogen purged addition funnel. The mixture was allowed to stir for 50 min, at which time 5-bromo-2,2-difluoro-1,3-benzodioxole (75 g, 316.5 mmol) was added over 1 min. After stirring for an additional 50 min, the mixture was charged with ethyl cyanoacetate (71.6 g, 633.0 mmol) over 5 min followed by water (4.5 mL) in one portion. The mixture was heated to 70° C. over 40 min and analyzed by HPLC every 1-2 h for the percent conversion of the reactant to the product. After complete conversion was observed (typically 100% conversion after 5-8 h), the mixture was cooled to 20-25° C. and filtered through a celite pad. The celite pad was rinsed with toluene (2×450 mL) and the combined organics were concentrated to 300 mL under vacuum at 60-65° C. The concentrate was charged with 225 mL DMSO and concentrated under vacuum at 70-80° C. until active distillation of the solvent ceased. The solution was cooled to 20-25° C. and diluted to 900 mL with DMSO in preparation for Step 2. $^1$H NMR (500 MHz, CDCl$_3$) δ 7.16-7.10 (m, 2H), 7.03 (d, J=8.2 Hz, 1H), 4.63 (s, 1H), 4.19 (m, 2H), 1.23 (t, J=7.1 Hz, 3H).

Synthesis of (2,2-difluoro-1,3-benzodioxol-5-yl)-acetonitrile

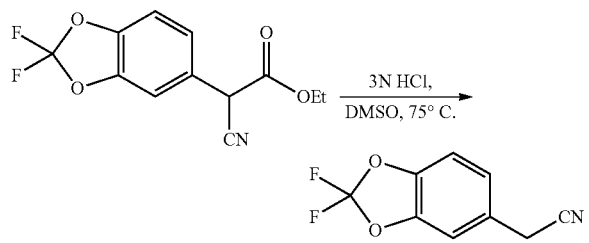

The DMSO solution of (2,2-difluoro-1,3-benzodioxol-5-yl)-1-ethylacetate-acetonitrile from above was charged with 3 N HCl (617.3 mL, 1.85 mol) over 20 min while maintaining an internal temperature <40° C. The mixture was then heated to 75° C. over 1 h and analyzed by HPLC every 1-2 h for % conversion. When a conversion of >99% was observed (typically after 5-6 h), the reaction was cooled to 20-25° C. and extracted with MTBE (2×525 mL), with sufficient time to allow for complete phase separation during the extractions. The combined organic extracts were washed with 5% NaCl (2×375 mL). The solution was then transferred to equipment appropriate for a 1.5-2.5 Torr vacuum distillation that was equipped with a cooled receiver flask. The solution was concentrated under vacuum at <60° C. to remove the solvents. (2,2-Difluoro-1,3-benzodioxol-5-yl)-acetonitrile was then distilled from the resulting oil at 125-130° C. (oven temperature) and 1.5-2.0 Torr. (2,2-Difluoro-1,3-benzodioxol-5-yl)-acetonitrile was isolated as a clear oil in 66% yield from 5-bromo-2,2-difluoro-1,3-benzodioxole (2 steps) and with an HPLC purity of 91.5% AUC (corresponds to a w/w assay of 95%). NMR (500 MHz, DMSO) δ 7.44 (br s, 1H), 7.43 (d, J=8.4 Hz, 1H), 7.22 (dd, J=8.2, 1.8 Hz, 1H), 4.07 (s, 2H).

Synthesis of (2,2-difluoro-1,3-benzodioxol-5-yl)-cyclopropanecarbonitrile

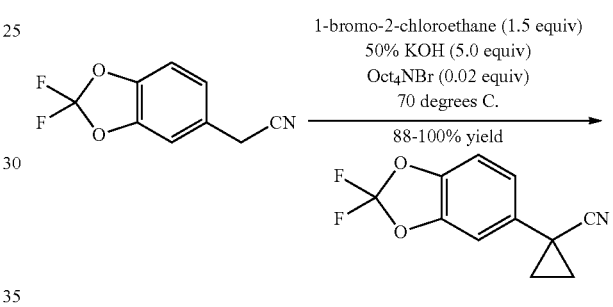

A mixture of (2,2-difluoro-1,3-benzodioxol-5-yl)-acetonitrile (1.0 eq), 50 wt % aqueous KOH (5.0 eq) 1-bromo-2-chloroethane (1.5 eq), and Oct$_4$NBr (0.02 eq) is heated at 70° C. for 1 h. The reaction mixture is cooled then worked up with MTBE and water. The organic phase is washed with water and brine then the solvent is removed to afford (2,2-difluoro-1,3-benzodioxol-5-yl)-cyclopropanecarbonitrile. $^1$H NMR (500 MHz, DMSO) δ 7.43 (d, J=8.4 Hz, 1H), 7.40 (d, J=1.9 Hz, 1H), 7.30 (dd, J=8.4, 1.9 Hz, 1H), 1.75 (m, 2H), 1.53 (m, 2H).

Synthesis of 1-(2,2-difluoro-1,3-benzodioxol-5-yl)-cyclopropanecarboxylic acid

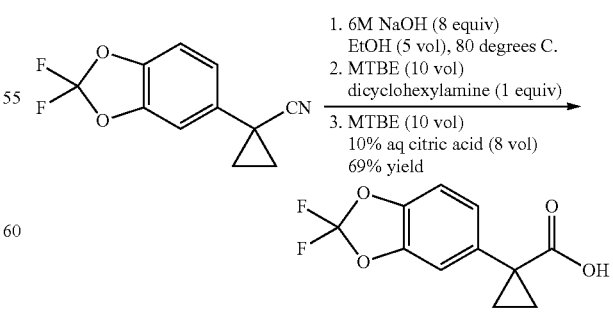

(2,2-difluoro-1,3-benzodioxol-5-yl)-cyclopropanecarbonitrile is hydrolyzed using 6 M NaOH (8 equiv) in ethanol (5 vol) at 80° C. overnight. The mixture is cooled to room temperature and ethanol is evaporated under vacuum. The residue is taken into water and MTBE, 1 M HCl was added and the layers are separated. The MTBE layer was then treated With dicyclohexylamine (0.97 equiv). The slurry is cooled to 0° C., filtered and washed with heptane to give the corresponding DCHA salt. The salt is taken into MTBE and 10% citric acid and stirred until all solids dissolve. The layers are separated and the MTBE layer was washed with water and brine. Solvent swap to heptane followed by filtration gives 1-(2,2-difluoro-1,3-benzodioxol-5-yl)-cyclopropanecarboxylic acid after drying in a vacuum oven at 50° C. overnight. ESI-MS m/z calc. 242.04. found 241.58 (M+1)$^+$; $^1$H NMR (500 MHz, DMSO) δ 12.40 (s, 1H), 7.40 (d, J=1.6 Hz, 1H), 7.30 (d, J=8.3 Hz, 1H), 7.17 (dd, J=8.3, 1.7 Hz, 1H), 1.46 (m, 2H), 1.17 (m, 2H).

Amine Moiety

Synthesis of 2-bromo-5-fluoro-4-nitroaniline

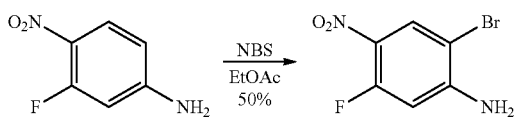 [SMILES: Nc1ccc([N+](=O)[O-])c(F)c1 ; "NBS" ; Nc1cc(F)c([N+](=O)[O-])cc1Br]

A flask was charged with 3-fluoro-4-nitroaniline (1.0 equiv) followed by ethyl acetate (10 vol) and stirred to dissolve all solids. N-Bromosuccinimide (1.0 equiv) was added as a portion-wise as to maintain internal temperature of 22° C. At the end of the reaction, the reaction mixture was concentrated in vacuo on a rotavap. The residue was slurried in distilled water (5 vol) to dissolve and remove succinimide. (The succinimide can also be removed by water workup procedure.) The water was decanted and the solid was slurried in 2-propanol (5 vol) overnight. The resulting slurry was filtered and the wetcake was washed with 2-propanol, dried in vacuum oven at 50° C. overnight with N$_2$ bleed until constant weight was achieved. A yellowish tan solid was isolated (50% yield, 97.5% AUC). Other impurities were a bromo-regioisomer (1.4% AUC) and a di-bromo adduct (1.1% AUC). NMR (500 MHz, DMSO) δ 8.19 (1H, d, J=8.1 Hz), 7.06 (br. s, 2H), 6.64 (d, 1H, J=14.3 Hz).

Synthesis of benzylglycolated-4-ammonium-2-bromo-5-fluoroaniline tosylate salt

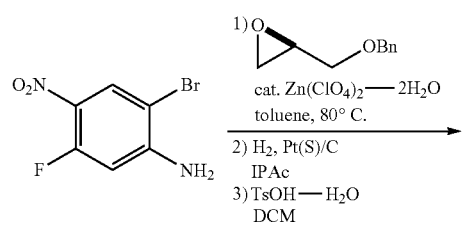

-continued

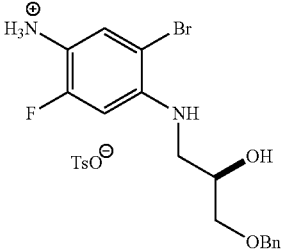

A thoroughly dried flask under N$_2$ was charged with the following: Activated powdered 4A molecular sieves (50 wt % based on 2-bromo-5-fluoro-4-nitroaniline), 2-Bromo-5-fluoro-4-nitroaniline (1.0 equiv), zinc perchlorate dihydrate (20 mol %), and toluene (8 vol). The mixture was stirred at room temperature for NMT 30 min. Lastly, (R)-benzyl glycidyl ether (2.0 equiv) in toluene (2 vol) was added in a steady stream. The reaction was heated to 80° C. (internal temperature) and stirred for approximately 7 hours or until 2-Bromo-5-fluoro-4-nitroaniline was <5% AUC.

The reaction was cooled to room temperature and Celite (50 wt %) was added, followed by ethyl acetate (10 vol). The resulting mixture was filtered to remove Celite and sieves and washed with ethyl acetate (2 vol). The filtrate was washed with ammonium chloride solution (4 vol, 20% w/v). The organic layer was washed with sodium bicarbonate solution (4 vol×2.5% w/v). The organic layer was concentrated in vacuo on a rotovap. The resulting slurry was dissolved in isopropyl acetate (10 vol) and this solution was transferred to a Buchi hydrogenator.

The hydrogenator was charged with 5 wt % Pt(S)/C (1.5 mol %) and the mixture was stirred under N$_2$ at 30° C. (internal temperature). The reaction was flushed with N$_2$ followed by hydrogen. The hydrogenator pressure was adjusted to 1 Bar of hydrogen and the mixture was stirred rapidly (>1200 rpm). At the end of the reaction, the catalyst was filtered through a pad of Celite and washed with dichloromethane (10 vol). The filtrate was concentrated in vacuo. Any remaining isopropyl acetate was chased with dichloromethane (2 vol) and concentrated on a rotavap to dryness.

The resulting residue was dissolved in dichloromethane (10 vol). p-Toluenesulfonic acid monohydrate (1.2 equiv) was added and stirred overnight. The product was filtered and washed with dichloromethane (2 vol) and suction dried. The wetcake was transferred to drying trays and into a vacuum oven and dried at 45° C. with N$_2$ bleed until constant weight was achieved. Benzylglycolated-4-ammonium-2-bromo-5-fluoroaniline tosylate salt was isolated as an off-white solid.

Chiral purity was determined to be >97% ee.

Synthesis of (3-Chloro-3-methylbut-1-ynyl)trimethylsilane

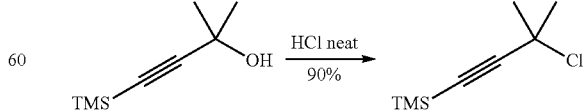

Propargyl alcohol (1.0 equiv) was charged to a vessel. Aqueous hydrochloric acid (37%, 3.75 vol) was added and stirring begun. During dissolution of the solid alcohol, a modest endotherm (5-6° C.) is observed. The resulting mixture was stirred overnight (16 h), slowly becoming dark red. A 30 L jacketed vessel is charged with water (5 vol) which is then cooled to 10° C. The reaction mixture is transferred slowly into the water by vacuum, maintaining the internal temperature of the mixture below 25° C. Hexanes (3 vol) is added and the resulting mixture is stirred for 0.5 h. The phases were settled and the aqueous phase (pH<1) was drained off and discarded. The organic phase was concentrated in vacuo using a rotary evaporator, furnishing the product as red oil.

Synthesis of (4-(Benzyloxy)-3,3-dimethylbut-1-ynyl) trimethylsilane

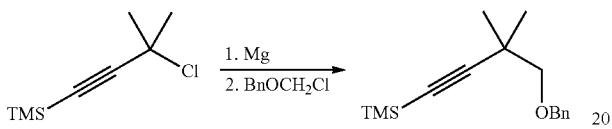

Method A

All equivalent and volume descriptors in this part are based on a 250 g reaction. Magnesium turnings (69.5 g, 2.86 mol, 2.0 equiv) were charged to a 3 L 4-neck reactor and stirred with a magnetic stirrer under nitrogen for 0.5 h. The reactor was immersed in an ice-water bath. A solution of the propargyl chloride (250 g, 1.43 mol, 1.0 equiv) in THF (1.8 L, 7.2 vol) was added slowly to the reactor, with stirring, until an initial exotherm (~10° C.) was observed. The Grignard reagent formation was confirmed by IPC using $^1$H-NMR spectroscopy. Once the exotherm subsided, the remainder of the solution was added slowly, maintaining the batch temperature <15° C. The addition required ~3.5 h. The resulting dark green mixture was decanted into a 2 L capped bottle.

All equivalent and volume descriptors in this part are based on a 500 g reaction. A 22 L reactor was charged with a solution of benzyl chloromethyl ether (95%, 375 g, 2.31 mol, 0.8 equiv) in THF (1.5 L, 3 vol). The reactor was cooled man ice-water bath. Two of the four Grignard reagent batches prepared above were combined and then added slowly to the benzyl chloromethyl ether solution via an addition funnel, maintaining the batch temperature below 25° C. The addition required 1.5 h. The reaction mixture was stirred overnight (16 h).

All equivalent and volume descriptors in this part are based on a 1 kg reaction. A solution of 15% ammonium chloride was prepared in a 30 L jacketed reactor (1.5 kg in 8.5 kg of water, 10 vol). The solution was cooled to 5° C. The two Grignard reaction mixtures above were combined and then transferred into the ammonium chloride solution via a header vessel. An exotherm was observed in this quench, which was carried out at a rate such as to keep the internal temperature below 25° C. Once the transfer was complete, the vessel jacket temperature was set to 25° C. Hexanes (8 L, 8 vol) was added and the mixture was stirred for 0.5 h. After settling the phases, the aqueous phase (pH 9) was drained off and discarded. The remaining organic phase was washed with water (2 L, 2 vol). The organic phase was concentrated in vacuo using a 22 L rotary evaporator, providing the crude product as an orange oil.

Method B

Magnesium turnings (106 g, 4.35 mol, 1.0 eq) were charged to a 22 L reactor and then suspended in THF (760 mL, 1 vol). The vessel was cooled in an ice-water bath such that the batch temperature reached 2° C. A solution of the propargyl chloride (760 g, 4.35 mol, 1.0 equiv) in THF (4.5 L, 6 vol) was added slowly to the reactor. After 100 mL was added, the addition was stopped and the mixture stirred until a 13° C. exotherm was observed, indicating the Grignard reagent initiation. Once the exotherm subsided, another 500 mL of the propargyl chloride solution was added slowly, maintaining the batch temperature <20° C. The Grignard reagent formation was confirmed by IPC using $^1$H-NMR spectroscopy. The remainder of the propargyl chloride solution was added slowly, maintaining the batch temperature <20° C. The addition required ~1.5 h. The resulting dark green solution was stirred for 0.5 h. The Grignard reagent formation was confirmed by IPC using $^1$H-NMR spectroscopy. Neat benzyl chloromethyl ether was charged to the reactor addition funnel and then added dropwise into the reactor, maintaining the batch temperature below 25° C. The addition required 1.0 h. The reaction mixture was stirred overnight. The aqueous work-up and concentration was carried out using the same procedure and relative amounts of materials as in Method A to give the product as an orange oil.

Synthesis of 4-Benzyloxy-3,3-dimethylbut-1-yne

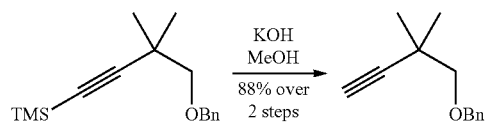 [SMILES: CC(C)(C#C[Si](C)(C)C)COCc1ccccc1 ; C#CC(C)(C)COCc1ccccc1]

A 30 L jacketed reactor was charged with methanol (6 vol) which was then cooled to 5° C. Potassium hydroxide (85%, 1.3 equiv) was added to the reactor. A 15-20° C. exotherm was observed as the potassium hydroxide dissolved. The jacket temperature was set to 25° C. A solution of 4-benzyloxy-3, 3-dimethyl-1-trimethylsilylbut-1-yne (1.0 equiv) in methanol (2 vol) was added and the resulting mixture was stirred until reaction completion, as monitored by HPLC. Typical reaction time at 25° C. is 3-4 h. The reaction mixture is diluted with water (8 vol) and then stirred for 0.5 h. Hexanes (6 vol) was added and the resulting mixture was stirred for 0.5 h. The phases were allowed to settle and then the aqueous phase (pH 10-11) was drained off and discarded. The organic phase was washed with a solution of KOH (85%, 0.4 equiv) in water (8 vol) followed by water (8 vol). The organic phase was then concentrated down using a rotary evaporator, yielding the title material as a yellow-orange oil. Typical purity of this material is in the 80% range with primarily a single impurity present. $^1$H NMR (400 MHz, C$_6$D$_6$) δ 7.28 (d, 2H, J=7.4 Hz), 7.18 (t, 2H, J=7.2 Hz), 7.10 (d, 1H, J=7.2 Hz), 4.35 (s, 2H), 3.24 (s, 2H), 1.91 (s, 1H), 1.25 (s, 6H).

Synthesis of Benzylglycolated 4-Amino-2-(4-benzyloxy-3,3-dimethylbut-1-ynyl)-5-fluoroaniline

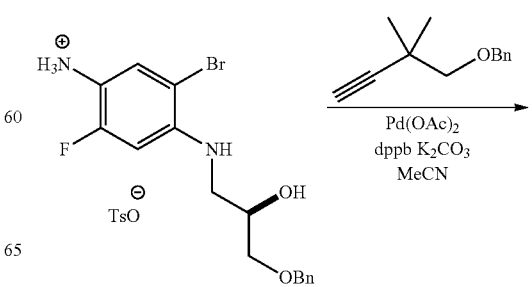

-continued

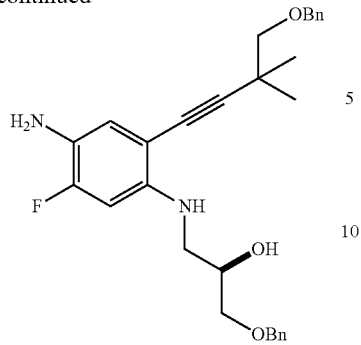

Benzylglycolated 4-ammonium-2-bromo-5-fluoroaniline tosylate salt was freebased by stirring the solid in EtOAc (5 vol) and saturated NaHCO$_3$ solution (5 vol) until clear organic layer was achieved. The resulting layers were separated and the organic layer was washed with saturated NaHCO$_3$ solution (5 vol) followed by brine and concentrated in vacuo to obtain benzylglycolated 4-ammonium-2-bromo-5-fluoroaniline tosylate salt as an oil.

Then, a flask was charged with benzylglycolated 4-ammonium-2-bromo-5-fluoroaniline tosylate salt (freebase, 1.0 equiv), Pd(OAc) (4.0 mol %), dppb (6.0 mol %) and powdered K$_2$CO$_3$ (3.0 equiv) and stirred with acetonitrile (6 vol) at room temperature. The resulting reaction mixture was degassed for approximately 30 min by bubbling in N$_2$ with vent. Then 4-benzyloxy-3,3-dimethylbut-1-yne (1.1 equiv) dissolved in acetonitrile (2 vol) was added in a fast stream and heated to 80° C. and stirred until complete consumption of 4-ammonium-2-bromo-5-fluoroaniline tosylate salt was achieved. The reaction slurry was cooled to room temperature and filtered through a pad of Celite and washed with acetonitrile (2 vol). Filtrate was concentrated in vacuo and the residue was redissolved in EtOAc (6 vol). The organic layer was washed twice with NH$_4$Cl solution (20% w/v, 4 vol) and brine (6 vol). The resulting organic layer was concentrated to yield brown oil and used as is in the next reaction.

Synthesis of N-benzylglycolated-5-amino-2-(2-benzyloxy-1,1-dimethylethyl)-6-fluoroindole

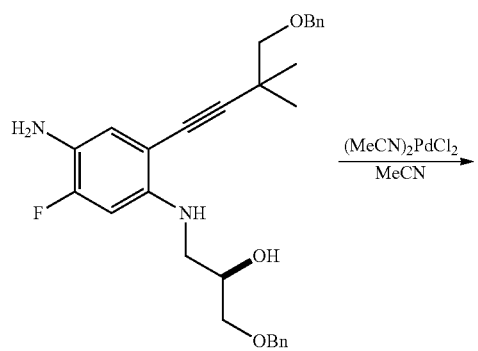

-continued

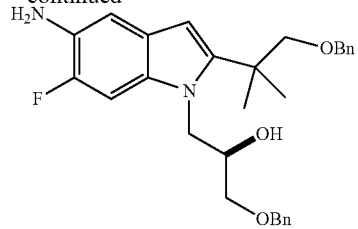

Crude oil of benzylglycolated 4-amino-2-(4-benzyloxy-3,3-dimethylbut-1-ynyl)-5-fluoroaniline was dissolved in acetonitrile (6 vol) and added (MeCN)$_2$PdCl$_2$ (15 mol %) at room temperature. The resulting mixture was degassed using N$_2$ with vent for approximately 30 min. Then the reaction mixture was stirred at 80° C. under N$_2$ blanket overnight. The reaction mixture was cooled to room temperature and filtered through a pad of Celite and washed the cake with acetonitrile (1 vol). The resulting filtrate was concentrated in vacuo and redissolved in EtOAc (5 vol). Deloxane-II THP (5 wt % based on the theoretical yield of N-benzylglycolated-5-amino-2-(2-benzyloxy-1,1-dimethylethyl)-6-fluoroindole) was added and stirred at room temperature overnight. The mixture was then filtered through a pad of silica (2.5 inch depth, 6 inch diameter filter) and washed with EtOAc (4 vol). The filtrate was concentrated down to a dark brown residue, and used as is in the next reaction.

Repurification of crude N-benzylglycolated-5-amino-2-(2-benzyloxy-1,1-dimethylethyl)-6-fluoroindole:

The crude N-benzylglycolated-5-amino-2-(2-benzyloxy-1,1-dimethylethyl)-6-fluoroindole was dissolved in dichloromethane (~1.5 vol) and filtered through a pad of silica initially using 30% EtOAc/heptane where impurities were discarded. Then the silica pad was washed with 50% EtOAc/heptane to isolate N-benzylglycolated-5-amino-2-(2-benzyloxy-1,1-dimethylethyl)-6-fluoroindole until faint color was observed in the filtrate. This filtrate was concentrated in vacuo to afford brown oil which crystallized on standing at room temperature. $^1$H NMR (400 MHz, DMSO) δ 7.38-7.34 (m, 4H), 7.32-7.23 (m, 6H), 7.21 (d, 1H, J=12.8 Hz), 6.77 (d, 1H, J=9.0 Hz), 6.06 (s, 1H), 5.13 (d, 1H, J=4.9 Hz), 4.54 (s, 2H), 4.46 (br. s, 2H), 4.45 (s, 2H), 4.33 (d, 1H, J=12.4 Hz), 4.09-4.04 (m, 2H), 3.63 (d, 1H, J=9.2 Hz), 3.56 (d, 1H, J=9.2 Hz), 3.49 (dd, 1H, J=9.8, 4.4 Hz), 3.43 (dd, 1H, J=9.8, 5.7 Hz), 1.40 (s, 6H).

Synthesis of Compound 1

Synthesis of Benzyl Protected Compound 1

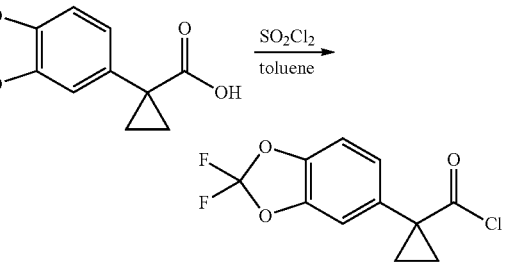

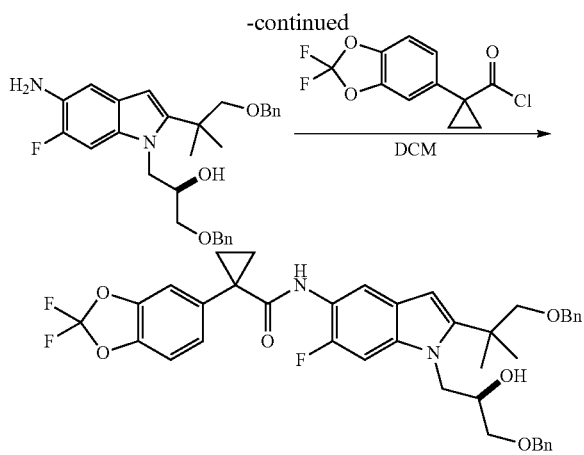

1-(2,2-difluoro-1,3-benzodioxol-5-yl)-cyclopropanecarboxylic acid (1.3 equiv) was slurried in toluene (2.5 vol, based on 1-(2,2-difluoro-1,3-benzodioxol-5-yl)-cyclopropanecarboxylic acid) and the mixture was heated to 60° C. SOCl$_2$ (1.7 equiv) was added via addition funnel. The resulting mixture was stirred for 2 hr. The toluene and the excess SOCl$_2$ were distilled off using rotavop. Additional toluene (2.5 vol, based on 1-(2,2-difluoro-1,3-benzodioxol-5-yl)-cyclopropanecarboxylic acid) was added and distilled again. The crude acid chloride was dissolved in dichloromethane (2 vol) and added via addition funnel to a mixture of N-benzylglycolated-5-amino-2-(2-benzyloxy-1,1-dimethylethyl)-6-fluoroindole (1.0 equiv), and triethylamine (2.0 equiv) in dichloromethane (7 vol) while maintaining 0-3° C. (internal temperature). The resulting mixture was stirred at 0° C. for 4 hrs and then warmed to room temperature overnight. Distilled water (5 vol) was added to the reaction mixture and stirred for NLT 30 min and the layers were separated. The organic phase was washed with 20 wt % K$_2$CO$_3$ (4 vol×2) followed by a brine wash (4 vol) and concentrated to afford crude benzyl protected Compound 1 as a thick brown oil, which was purified further using silica pad filtration.

Silica Gel Pad Filtration:

Crude benzyl protected Compound 1 was dissolved in ethyl acetate (3 vol) in the presence of activated carbon Darco-G (10 wt %, based on theoretical yield of benzyl protected Compound 1) and stirred at room temperature overnight. To this mixture was added heptane (3 vol) and filtered through a pad of silica gel (2× weight of crude benzyl protected Compound 1). The silica pad was washed with ethyl acetate/heptane (1:1, 6 vol) or until little color was detected in the filtrate. The filtrate was concentrated in vacuo to afford benzyl protected Compound 1 as viscous reddish brown oil, and used directly in the next step.

Repurification:

Benzyl protected Compound 1 was redissolved in dichloromethane (1 vol, based on theoretical yield of benzyl protected Compound 1) and loaded onto a silica gel pad (2× weight of crude benzyl protected Compound 1). The silica pad was washed with dichloromethane (2 vol, based on theoretical yield of benzyl protected Compound 1) and the filtrate was discarded. The silica pad was washed with 30% ethyl acetate/heptane (5 vol) and the filtrate was concentrated in vacuo to afford benzyl protected Compound 1 as viscous reddish orange oil, and used directly in the next step.

Synthesis of Compound 1

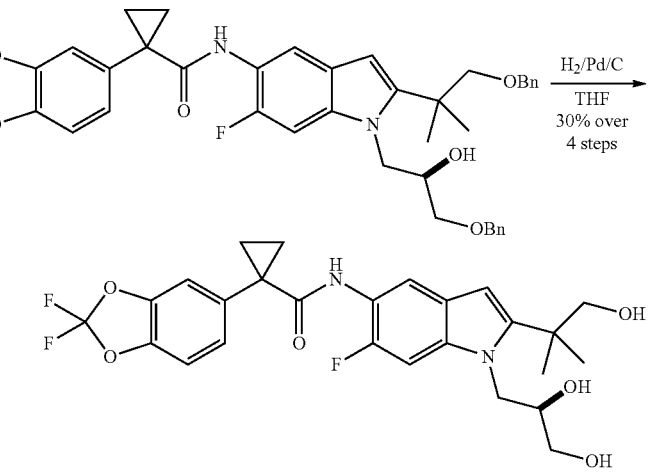

Method A

A 20 L autoclave was flushed three times with nitrogen gas and then charged with palladium on carbon (Evonik E 101 NN/W, 5% Pd, 60% wet, 200 g, 0.075 mol, 0.04 equiv). The autoclave was then flushed with nitrogen three times. A solution of crude benzyl protected Compound 1 (1.3 kg, ~1.9 mol) in THF (8 L, 6 vol) was added to the autoclave via suction. The vessel was capped and then flushed three times with nitrogen gas. With gentle stirring, the vessel was flushed three times with hydrogen gas, evacuating to atmosphere by diluting with nitrogen. The autoclave was pressurized to 3 Bar with hydrogen and the agitation rate was increased to 800 rpm. Rapid hydrogen uptake was observed (dissolution). Once uptake subsided, the vessel was heated to 50° C.

For safety purposes, the thermostat was shut off at the end of every work-day. The vessel was pressurized to 4 Bar with hydrogen and then isolated from the hydrogen tank.

After 2 full days of reaction, more Pd/C (60 g, 0.023 mol, 0.01 equiv) was added to the mixture. This was done by flushing three times with nitrogen gas and then adding the catalyst through the solids addition port. Resuming the reaction was done as before. After 4 full days, the reaction was deemed complete by HPLC by the disappearance of not only the starting material but also of the peak corresponding to a mono-benzylated intermediate.

The reaction mixture was filtered through a Celite pad. The vessel and filter cake were washed with THF (2 L, 1.5 vol). The Celite pad was then wetted with water and the cake discarded appropriately. The combined filtrate and THF wash were concentrated using a rotary evaporator yielding the crude product as a black oil, 1 kg.

The equivalents and volumes in the following purification are based on 1 kg of crude material. The crude black oil was dissolved in 1:1 ethyl acetate-heptane. The mixture was charged to a pad of silica gel (1.5 kg, 1.5 wt. equiv) in a fritted funnel that had been saturated with 1:1 ethyl acetate-heptane. The silica pad was flushed first with 1:1 ethyl acetate-heptane (6 L, 6 vol) and then with pure ethyl acetate (14 L, 14 vol). The eluent was collected in 4 fractions which were analyzed by HPLC.

The equivalents and volumes in the following purification are based on 0.6 kg of crude material. Fraction 3 was concentrated by rotary evaporation to give a brown foam (600 g) and then redissolved in MTBE (1.8 L, 3 vol). The dark brown solution was stirred overnight at ambient temperature, during which time, crystallization occurred. Heptane (55 mL, 0.1 vol) was added and the mixture was stirred overnight. The mixture was filtered using a Buchner funnel and the filter cake was washed with 3:1 MTBE-heptane (900 mL, 1.5 vol). The filter cake was air-dried for 1 h and then vacuum dried at ambient temperature for 16 h, furnishing 253 g of VXc-661 as an off-white solid.

The equivalents and volumes for the following purification are based on 1.4 kg of crude material. Fractions 2 and 3 from the above silica gel filtration as well as material from a previous reaction were combined and concentrated to give 1.4 kg of a black oil. The mixture was resubmitted to the silica gel filtration (1.5 kg of silica gel, eluted with 3.5 L, 2.3 vol of 1:1 ethyl acetate-heptane then 9 L, 6 vol of pure ethyl acetate) described above, which upon concentration gave a tan foamy solid (390 g).

The equivalents and volumes for the following purification are based on 390 g of crude material. The tan solid was insoluble in MTBE, so was dissolved in methanol (1.2 L, 3 vol). Using a 4 L Morton reactor equipped with a long-path distillation head, the mixture was distilled down to 2 vol. MTBE (1.2 L, 3 vol) was added and the mixture was distilled back down to 2 vol. A second portion of MTBE (1.6 L, 4 vol) was added and the mixture was distilled back down to 2 vol. A third portion of MTBE (1.2 L, 3 vol) was added and the mixture was distilled back down to 3 vol. Analysis of the distillate by GC revealed it to consist of ~6% methanol. The thermostat was set to 48° C. (below the boiling temp of the MTBE-methanol azeotrope, which is 52° C.). The mixture was cooled to 20° C. over 2 h, during which time a relatively fast crystallization occurred. After stirring the mixture for 2 h, heptane (20 mL, 0.05 vol) was added and the mixture was stirred overnight (16 h). The mixture was filtered using a Buchner funnel and the filter cake was washed with 3:1 MTBE-heptane (800 mL, 2 vol). The filter cake was air-dried for 1 h and then vacuum dried at ambient temperature for 16 h, furnishing 130 g of Compound 1 as an off-white solid.

Method B

Benzyl protected Compound 1 was dissolved and flushed with THF (3 vol) to remove any remaining residual solvent. Benzyl protected Compound 1 was redissolved in THF (4 vol) and added to the hydrogenator containing 5 wt % Pd/C (2.5 mol %, 60% wet, Degussa E5 E101 NN/W). The internal temperature of the reaction was adjusted to 50° C., and flushed with $N_2$ (×5) followed by hydrogen (×3). The hydrogenator pressure was adjusted to 3 Bar of hydrogen and the mixture was stirred rapidly (>1100 rpm). At the end of the reaction, the catalyst was filtered through a pad of Celite and washed with THF (1 vol). The filtrate was concentrated in vacuo to obtain a brown foamy residue. The resulting residue was dissolved in MTBE (5 vol) and 0.5N HCl solution (2 vol) and distilled water (1 vol) were added. The mixture was stirred for NLT 30 min and the resulting layers were separated. The organic phase was washed with 10 wt % $K_2CO_3$ solution (2 vol×2) followed by a brine wash. The organic layer was added to a flask containing silica gel (25 wt %), Deloxan-THP H (5 wt %, 75% wet), and $Na_2SO_4$ and stirred overnight. The resulting mixture was filtered through a pad of Celite and washed with 10% THF/MTBE (3 vol). The filtrate was concentrated in vacuo to afford crude Compound 1 as pale tan foam.

Compound 1 Recovery from the Mother Liquor: Option A.
Silica Gel Pad Filtration:

The mother liquor was concentrated in vacuo to obtain a brown foam, dissolved in dichloromethane (2 vol), and filtered through a pad of silica (3× weight of the crude Compound 1). The silica pad was washed with ethyl acetate/heptane (1:1, 13 vol) and the filtrate was discarded. The silica pad was washed with 10% THF/ethyl acetate (10 vol) and the filtrate was concentrated in vacuo to afford Compound 1 as pale tan foam. The above crystallization procedure was followed to isolate the remaining Compound 1.

Compound 1 Recovery from the Mother Liquor: Option B.
Silica Gel Column Chromatography:

After chromatography on silica gel (50% ethyl acetate/hexanes to 100% ethyl acetate), the desired compound was isolated as pale tan foam. The above crystallization procedure was followed to isolate the remaining Compound 1.

Figure 2:
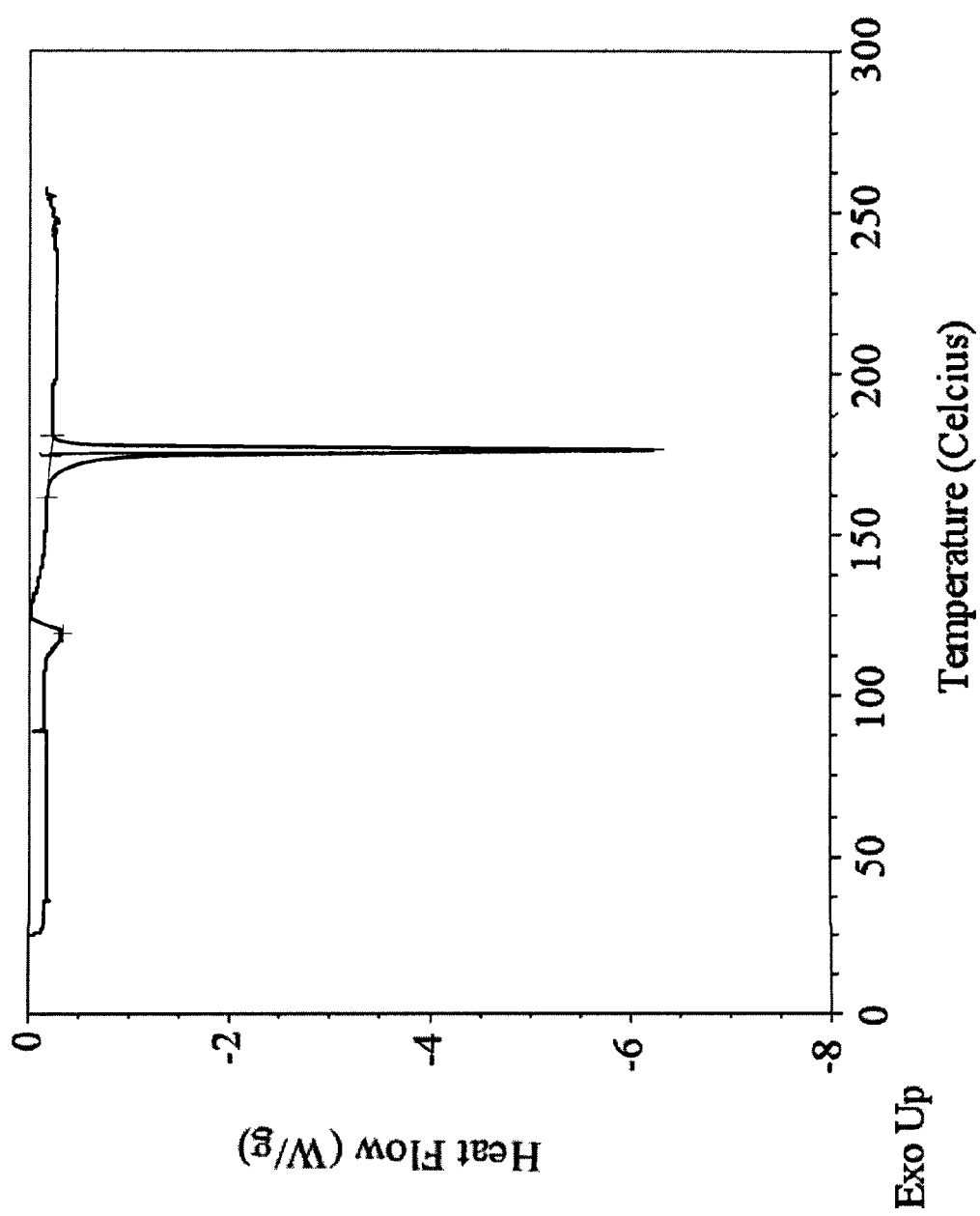
FIG. 2 is a differential scanning calorimetry (DSC) trace of Compound 1.
Figure 3:
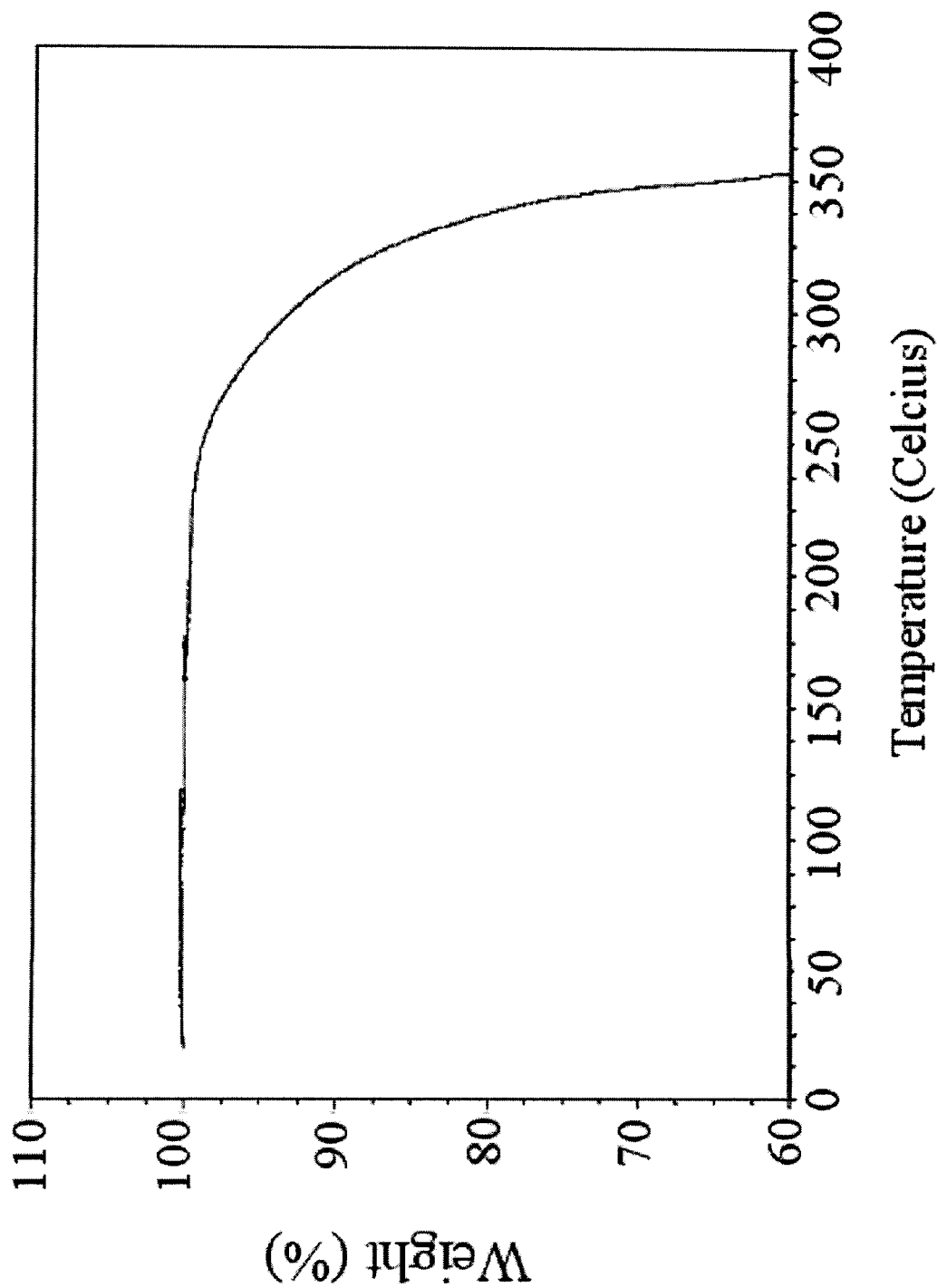
FIG. 3 is thermogravimetric analysis (TGA) plot of Compound 1.

FIG. 1 shows an X-ray powder diffraction pattern of Compound 1. A DSC trace of Compound 1 is shown in FIG. 2. The DSC trace in FIG. 2 indicates that Compound 1 is not a pure solid phase. An extra peak at 119° C. exists compared to Compound 1 Form A (see FIG. 6). A TGA trace of Compound 1 is shown in FIG. 3.

Compound 1 may also be prepared by one of several synthetic routes disclosed in US published patent application US20090131492, incorporated herein by reference.

Synthesis of Compound 1 Form A
Slurry Method

Figure 5:
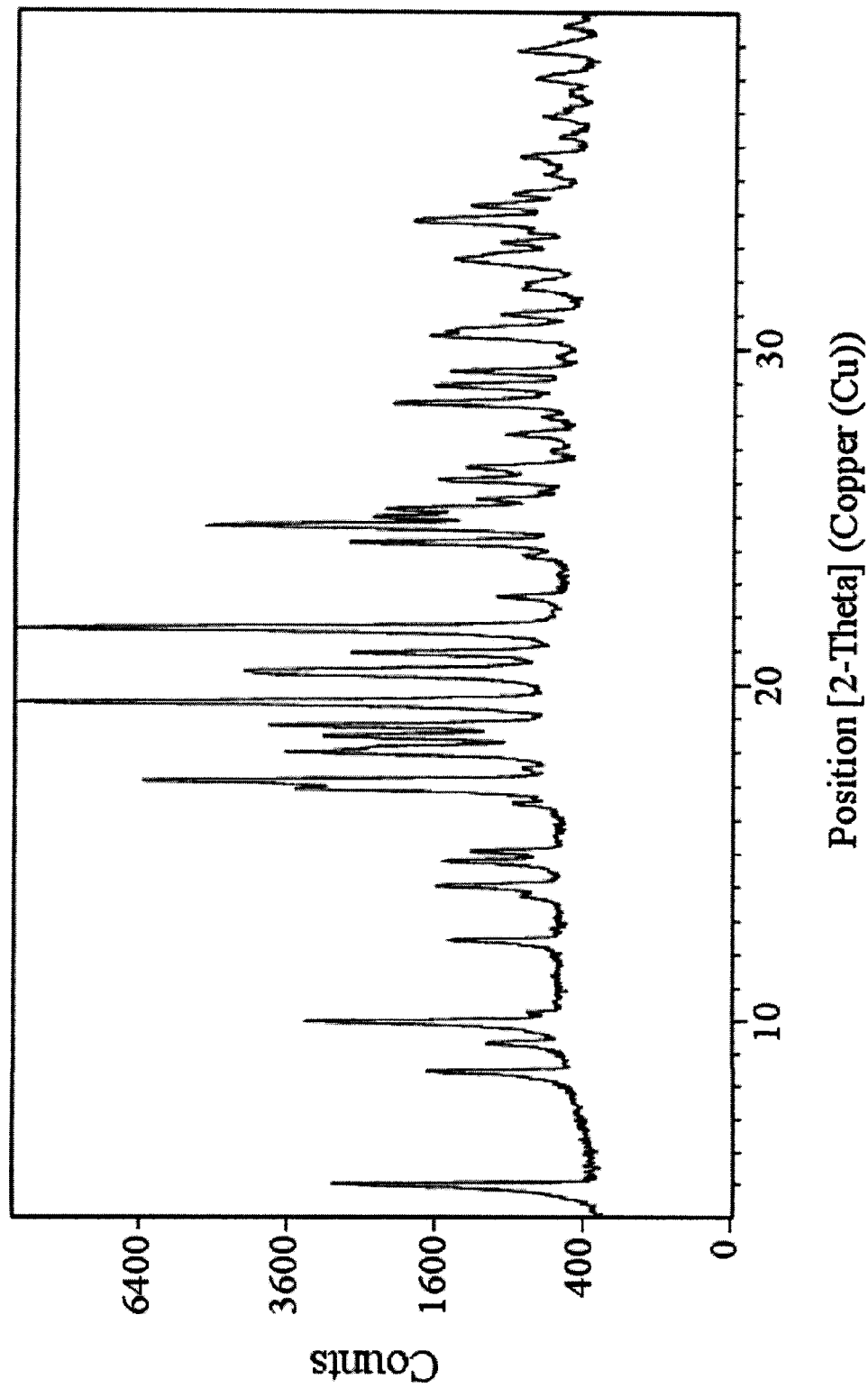
FIG. 5 is an actual X-ray powder diffraction pattern of Compound 1 Form A prepared by the slurry technique (2 weeks) with DCM as the solvent.

For EtOAc, MTBE, Isopropyl acetate, or DCM, approximately 40 mg of Compound 1 was added to a vial along with 1-2 ml of any one of the above solvents. The slurry was stirred at room temperature for 24 h to 2 weeks and Compound 1 Form A was collected by centrifuging the suspension (with filter). FIG. 5 discloses an XRPD pattern of Compound 1 Form A obtained by this method with DCM as the solvent.

For EtOH/water solutions, approximately 40 mg of Compound 1 was added to three separate vials. In the first vial, 1.35 ml of EtOH and 0.15 ml of water were added. In the second vial, 0.75 ml of EtOH and 0.75 ml of water were added. In the third vial, 0.15 ml of EtOH and 1.35 ml of water were added. All three vials were stirred at room temperature for 24 h. Each suspension was then centrifuged separately (with filter) to collect Compound 1 Form A.

For isopropyl alcohol/water solutions, approximately 40 mg of Compound 1 was added to three separate vials. In the first vial, 1.35 ml of isopropyl alcohol and 0.15 ml of water were added. In the second vial, 0.75 ml of isopropyl alcohol and 0.75 ml of water were added. In the third vial, 0.15 ml of isopropyl alcohol and 1.35 ml of water were added. All three vials were stirred at room temperature for 24 h. Each suspension was then centrifuged separately (with filter) to collect Compound 1 Form A.

For methanol/water solutions, approximately 40 mg of Compound 1 was added to a vial. 0.5 ml of methanol and 1 ml of water were added and the suspension was stirred at room temperature for 24 h. The suspension was centrifuged (with filter) to collect Compound 1 Form A.

For acetonitrile, approximately 50 mg of Compound 1 was added to a vial along with 2.0 ml of acetonitrile. The suspension was stirred at room temperature for 24 h and Compound 1 Form A was collected by centrifuge (with filter).

For acetonitrile/water solutions, approximately 50 mg of Compound 1 was dissolved in 2.5 ml of acetonitrile to give a clear solution after sonication. The solution was filtered and 1 ml withdrawn to a vial. 2.25 ml of water was added to give a cloudy suspension. The suspension was stirred at room temperature for 24 h and Compound 1 Form A was collected by centrifuge (with filter).

Slow Evaporation Method

Approximately 55 mg of Compound 1 was dissolved in 0.5 ml of acetone to give a clear solution after sonication. The solution was filtered and 0.2 ml was withdrawn to a vial. The vial was covered with parafilm with one hole poked in it and allowed to stand. Recrystallized Compound 1 Form A was collected by filtering.

Fast Evaporation Method

For isopropyl alcohol, approximately 43 mg of Compound 1 was dissolved in 2.1 ml of isopropyl alcohol to give a clear solution after sonication. The solution was filtered into a vial and allowed to stand uncovered. Recrystallized Compound 1 Form A was collected by filtering.

For methanol, approximately 58 mg of Compound 1 was dissolved in 0.5 ml of methanol to give a clear solution after sonication. The solution was filtered and 0.2 ml was withdrawn to an uncovered vial and allowed to stand. Recrystallized Compound 1 Form A was collected by filtering.

Figure 7:
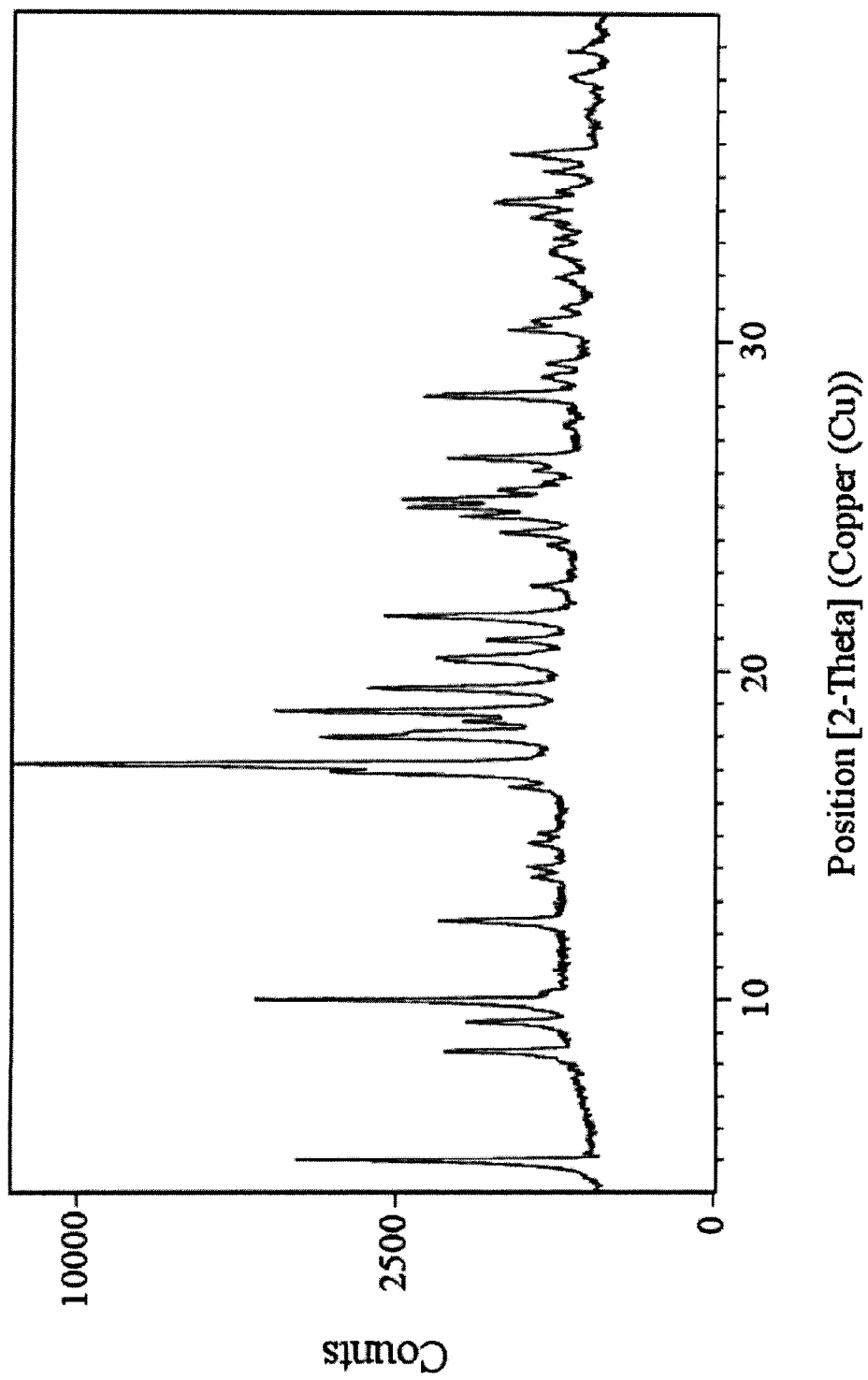
FIG. 7 is an actual X-ray powder diffraction pattern of Compound 1 Form A prepared by the fast evaporation method from acetonitrile.

For acetonitrile, approximately 51 mg of Compound 1 was dissolved in 2.5 ml of acetonitrile to give a clear solution after sonication. The solution was filtered and half the solution was withdrawn to an uncovered vial and allowed to stand. Recrystallized Compound 1 Form A was collected by filtering. FIG. 7 discloses an XRPD pattern of Compound 1 Form A prepared by this method.

Anti-Solvent Method

Figure 8:
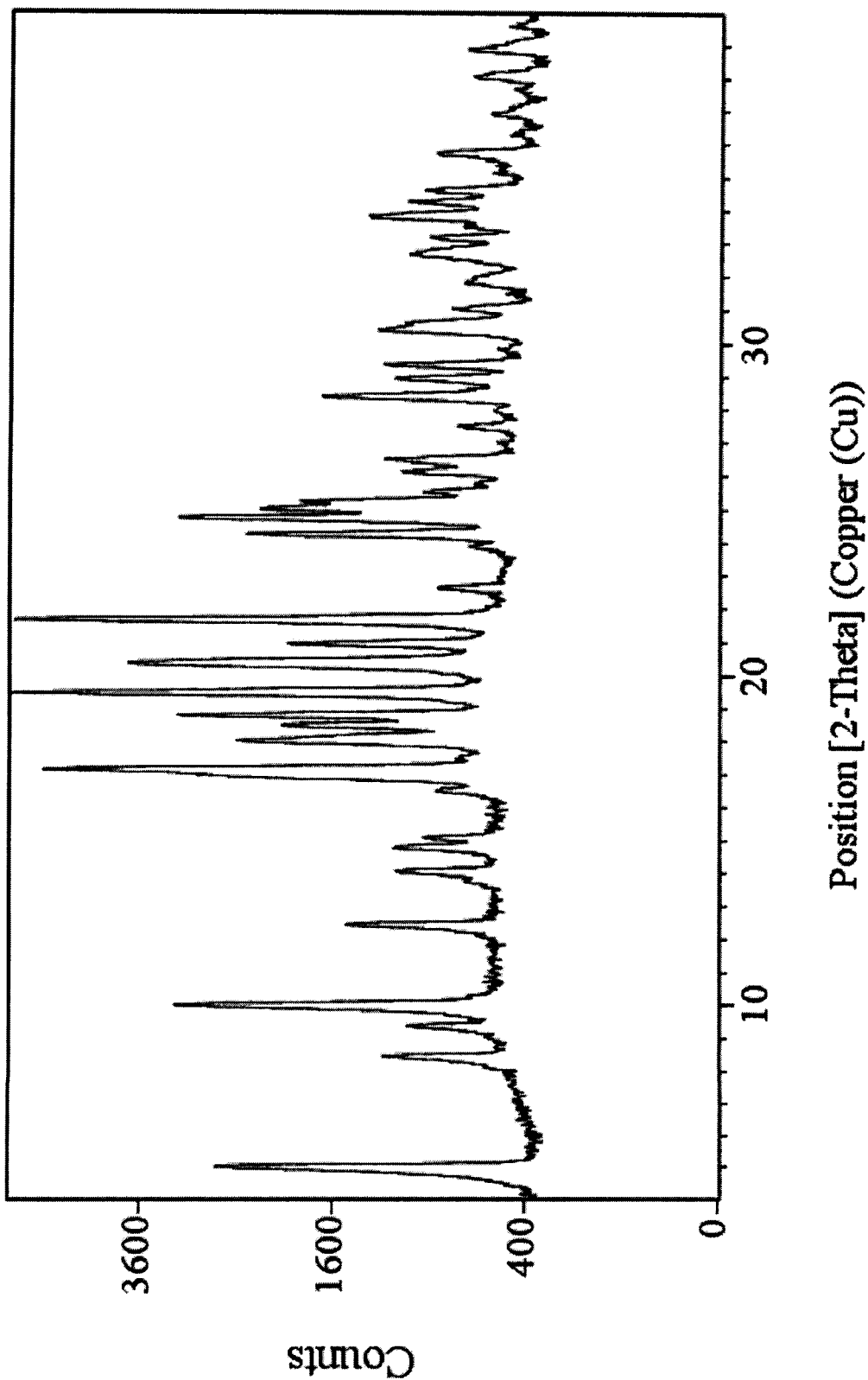
FIG. 8 is an actual X-ray powder diffraction pattern of Compound 1 Form A prepared by the anti solvent method using EtOAc and heptane.

For EtOAc/heptane, approximately 30 mg of Compound 1 was dissolved in 1.5 ml of EtOAc to give a clear solution after sonicating. The solution was filtered and 2.0 ml of heptane was added to the filtered solution while slowly stirring. The solution was stirred for an additional 10 minutes and allowed to stand. Recrystallized Compound 1 Form A was collected by filtering. FIG. 8 discloses an XRPD pattern of Compound 1 Form A prepared by this method.

For isopropyl alcohol/water, approximately 21 mg of Compound 1 was dissolved in 1.0 ml of isopropyl alcohol to give a clear solution after sonicating. The solution was filtered to give 0.8 ml of solution. 1.8 ml of water was added while slowly stirring. An additional 0.2 ml of water was added to give a cloudy suspension. Stirring was stopped for 5 minutes to give a clear solution. The solution was stirred for an additional 2 minutes and allowed to stand. Recrystallized Compound 1 Form A was collected by filtering.

For ethanol/water, approximately 40 mg of Compound 1 was dissolved in 1.0 ml of ethanol to give a clear solution after sonicating. The solution was filtered and 1.0 ml of water was added. The solution was stirred for 1 day at room temperature. Recrystallized Compound 1 Form A was collected by filtering.

For acetone/water, approximately 55 mg of Compound 1 was dissolved in 0.5 ml of acetone to give a clear solution after sonicating. The solution was filtered and 0.2 ml was withdrawn to a vial. 1.5 ml of water was added, and then an additional 0.5 ml of water to give a cloudy suspension. The suspension was stirred for 1 day at room temperature. Compound 1 Form A was collected by filtering.

Table 2 below summarizes the various techniques to form Compound 1 Form A.

TABLE 2

| Vehicle | Re-crystallization method | Results of residue solid |
| --- | --- | --- |
| ACN | Fast Evaporation | Form A |
| Methanol | Fast Evaporation | Form A |
| Ethanol | N/A | N/A |
| IPA | Fast Evaporation | Form A |
| Acetone | Slow Evaporation | Form A |
| EtOAc | Slurry | Form A |
| DCM | Slurry | Form A |
| MTBE | Slurry | Form A |
| Isopropyl acetate | Slurry | Form A |
| Water/Ethanol 1:9 | N/A | N/A |
| Water/Ethanol 1:1 | Slurry | Form A |
| Water/Ethanol 9:1 | Slurry | Form A |
| Water/ACN 9:4 | Slurry | Form A |
| Water/Methanol 2:1 | Slurry | Form A |
| Water/IPA 1:9 | N/A | N/A |
| Water/IPA 9:1 | Slurry | Form A |
| Water/IPA 7:3 | Slurry | Form A |
| Methanol/Water 4:3 | Slurry | Form A |
| EtOAc/Heptane 3:4 | Anti-solvent | Form A |
| IPA/Water 2:5 | Anti-solvent | Form A |
| Ethanol/Water 1:1 | Anti-solvent | Form A |
| Acetone/water 1:10 | Anti-solvent | Form A |
| Ethanol/Water 5:6 | Anti-solvent | N/A |
| Toluene | N/A | N/A |
| MEK | N/A | N/A |
| Water | N/A | N/A |

An X-ray diffraction pattern calculated from a single crystal structure of Compound 1 Form A is shown in FIG. 4. Table 3 lists the calculated peaks for FIG. 1.

TABLE 3

| Peak Rank | 2θ Angle [degrees] | Relative Intensity [%] |
| --- | --- | --- |
| 1 | 19.4 | 100.0 |
| 2 | 21.6 | 81.9 |
| 3 | 17.1 | 71.4 |
| 4 | 5.0 | 56.1 |
| 5 | 20.3 | 49.6 |
| 6 | 18.8 | 43.4 |
| 7 | 24.7 | 36.6 |
| 8 | 18.4 | 33.9 |
| 9 | 10.0 | 31.2 |
| 10 | 24.2 | 24.0 |
| 11 | 14.0 | 20.7 |
| 12 | 20.9 | 19.9 |
| 13 | 8.4 | 18.4 |
| 14 | 14.7 | 18.2 |
| 15 | 18.0 | 16.0 |
| 16 | 12.4 | 14.9 |

An actual X-ray powder diffraction pattern of Compound 1 Form A is shown in FIG. 5. Table 4 lists the actual peaks for FIG. 5.

TABLE 4

| Peak Rank | 2θ Angle [degrees] | Relative Intensity [%] |
|---|---|---|
| 1 | 19.5 | 100.0 |
| 2 | 21.7 | 88.2 |
| 3 | 17.1 | 85.1 |
| 4 | 20.4 | 80.9 |
| 5 | 18.8 | 51.0 |
| 6 | 24.7 | 40.8 |
| 7 | 10.0 | 40.7 |
| 8 | 5.0 | 39.0 |
| 9 | 24.2 | 35.4 |
| 10 | 18.5 | 35.0 |
| 11 | 18.0 | 29.0 |
| 12 | 20.9 | 27.0 |
| 13 | 14.8 | 19.9 |
| 14 | 14.1 | 19.2 |
| 15 | 12.4 | 18.2 |
| 16 | 8.4 | 14.1 |

Figure 6:
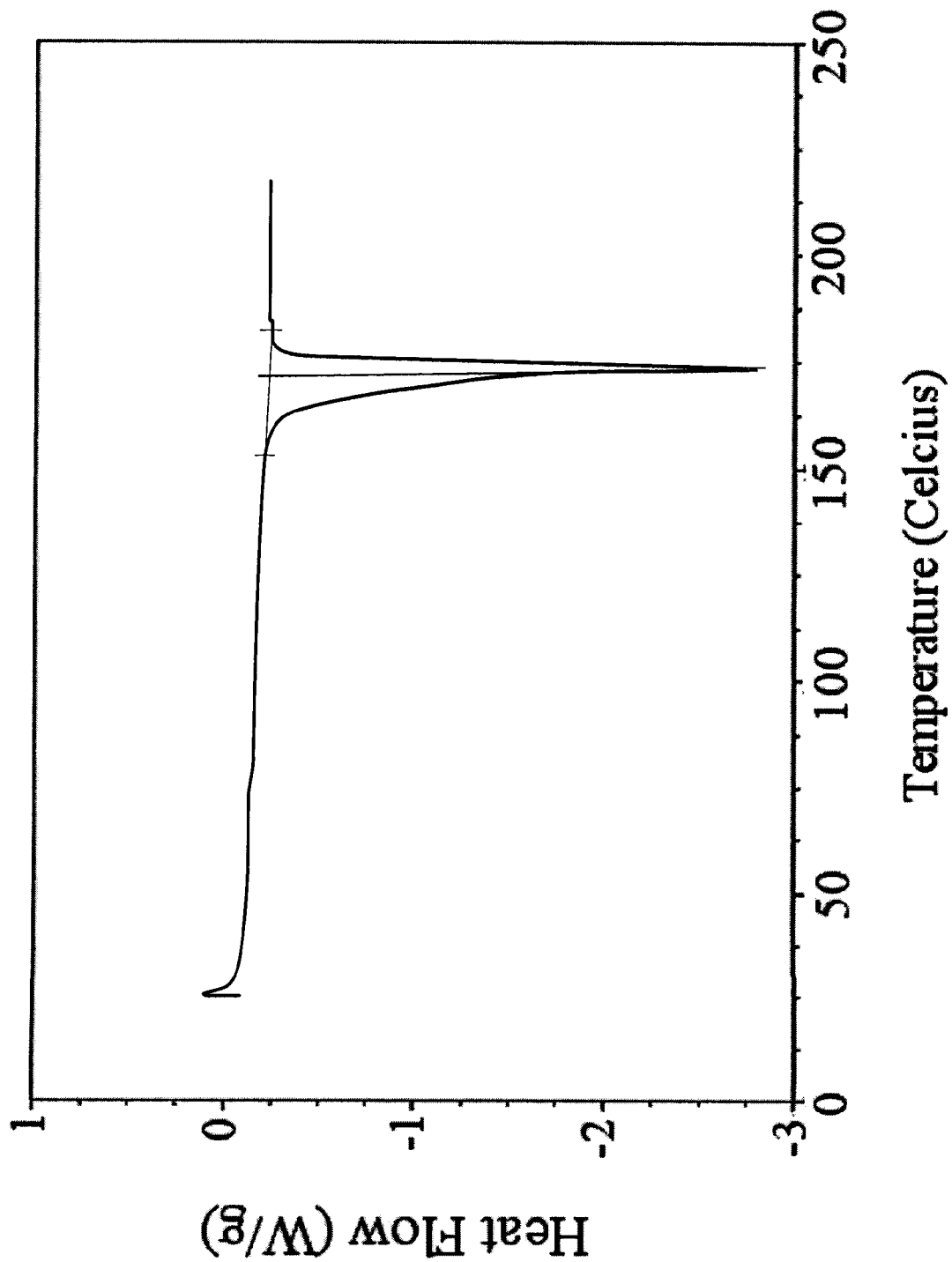
FIG. 6 is a differential scanning calorimetry (DSC) trace of Compound 1 Form A.

The DSC trace of Compound 1 Form A is shown in FIG. 6. Melting point for Compound 1 Form A occurs at about 172-178° C.

Single crystal data were obtained for Compound 1 Form A, providing additional detail about the crystal structure, including lattice size and packing.

Crystal Preparation

Crystals of Compound 1 Form A were obtained by slow evaporation from a concentrated solution of methanol (10 mg/ml). A colorless crystal of Compound 1 Form A with dimensions of 0.20×0.05×0.05 mm was selected, cleaned using mineral oil, mounted on a MicroMount and centered on a Bruker APEXII diffractometer. Three batches of 40 frames separated in reciprocal space were obtained to provide an orientation matrix and initial cell parameters. Final cell parameters were obtained and refined based on the full data set.

Experimental

A diffraction data set of reciprocal space was obtained to a resolution of 0.83 Å using 0.5° steps with 30 s exposure for each frame. Data were collected at room temperature [295 (2) K]. Integration of intensities and refinement of cell parameters were accomplished using APEXII software. Observation of the crystal after data collection showed no signs of decomposition.

TABLE 5

Crystal data for Compound 1 Form A

| | |
|---|---|
| $C_{26}H_{27}F_3N_2O_6$ | $F(000) = 1088$ |
| $M_r = 520.50$ | $D_x = 1.397$ Mg m$^{-3}$ |
| Monoclinic, C2 | Cu Kα radiation, λ = 1.54178 Å |
| Hall symbol: C 2y | Cell parameters from 3945 reflections |
| a = 21.0952 (16) Å | θ = 2.5° |
| b = 6.6287 (5) Å | μ = 0.97 mm$^{-1}$ |
| c = 17.7917 (15) Å | T = 295K |
| β = 95.867 (6)° | Prism |
| V = 2474.8 (3) Å$^3$ | 0.20 × 0.05 × 0.05 mm |
| Z = 4 | |

Geometry:

All esds (except the esd in the dihedral angle between two l.s. planes) are estimated using the full covariance matrix. The cell esds are taken into account individually in the estimation of esds in distances, angles and torsion angles; correlations between esds in cell parameters are only used when they are defined by crystal symmetry. An approximate (isotropic) treatment of cell esds is used for estimating esds involving l.s. planes.

TABLE 6

Data collection parameters for Compound 1 Form A crystal.

| | |
|---|---|
| APEX II diffractometer | $R_{int} = 0.027$ |
| Radiation source: fine-focus sealed tube | $θ_{max} = 67.8°, θ_{min} = 2.5°$ |
| graphite | h = −25→24 |
| 8766 measured reflections | k = −7→7 |
| 3945 independent reflections | l = −19→16 |
| 3510 reflections with I > 2σ(I) | |

Data Collection:

Apex II; cell refinement: Apex II; data reduction: Apex II; program(s) used to solve structure: SHELXS97 (Sheldrick, 1990); program(s) used to refine structure: SHELXL97 (Sheldrick, 1997); molecular graphics: Mercury; software used to prepare material for publication: publCIF.

TABLE 7

Refinement parameters for Compound 1 Form A crystal.

| | |
|---|---|
| Refinement on $F^2$ | Hydrogen site location: inferred from neighbouring sites |
| Least-squares matrix: full | H atoms treated by a mixture of independent and constrained refinement |
| $R[F^2 > 2σ(F^2)] = 0.043$ | $w = 1/[σ^2(F_o^2) + (0.0821P)^2 + 0.2233P]$ where $P = (F_o^2 + 2F_c^2)/3$ |
| $wR(F^2) = 0.119$ | $(Δ/σ)_{max} < 0.001$ |
| S = 1.05 | $Δ⟩_{max} = 0.14$ e Å$^{-3}$ |
| 3945 reflections | $Δ⟩_{max} = -0.13$ e Å$^{-3}$ |
| 443 parameters | Extinction correction: SHELXL, $Fc^* = kFc[1 + 0.001 × Fc^2λ^3/\sin(2θ)]^{-1/4}$ |
| 1 restraint | Extinction coefficient: 0.00016 (15) |
| 0 constraints | Absolute structure: Flack H D (1983), Acta Cryst. A39, 876-881 |
| Primary atom site location: structure-invariant direct methods | Flack parameter: 0.00 (18) |
| Secondary atom site location: difference Fourier map | |

Refinement:

Refinement of $F^2$ against ALL reflections. The weighted R-factor wR and goodness of fit S are based on $F^2$, conventional R-factors R are based on F, with F set to zero for negative $F^2$. The threshold expression of $F^2>2\text{sigma}(F^2)$ is used only for calculating R-factors(gt) etc. and is not relevant to the choice of reflections for refinement. R-factors based on $F^2$ are statistically about twice as large as those based on F, and R-factors based on ALL data will be even larger.

Figure 9:
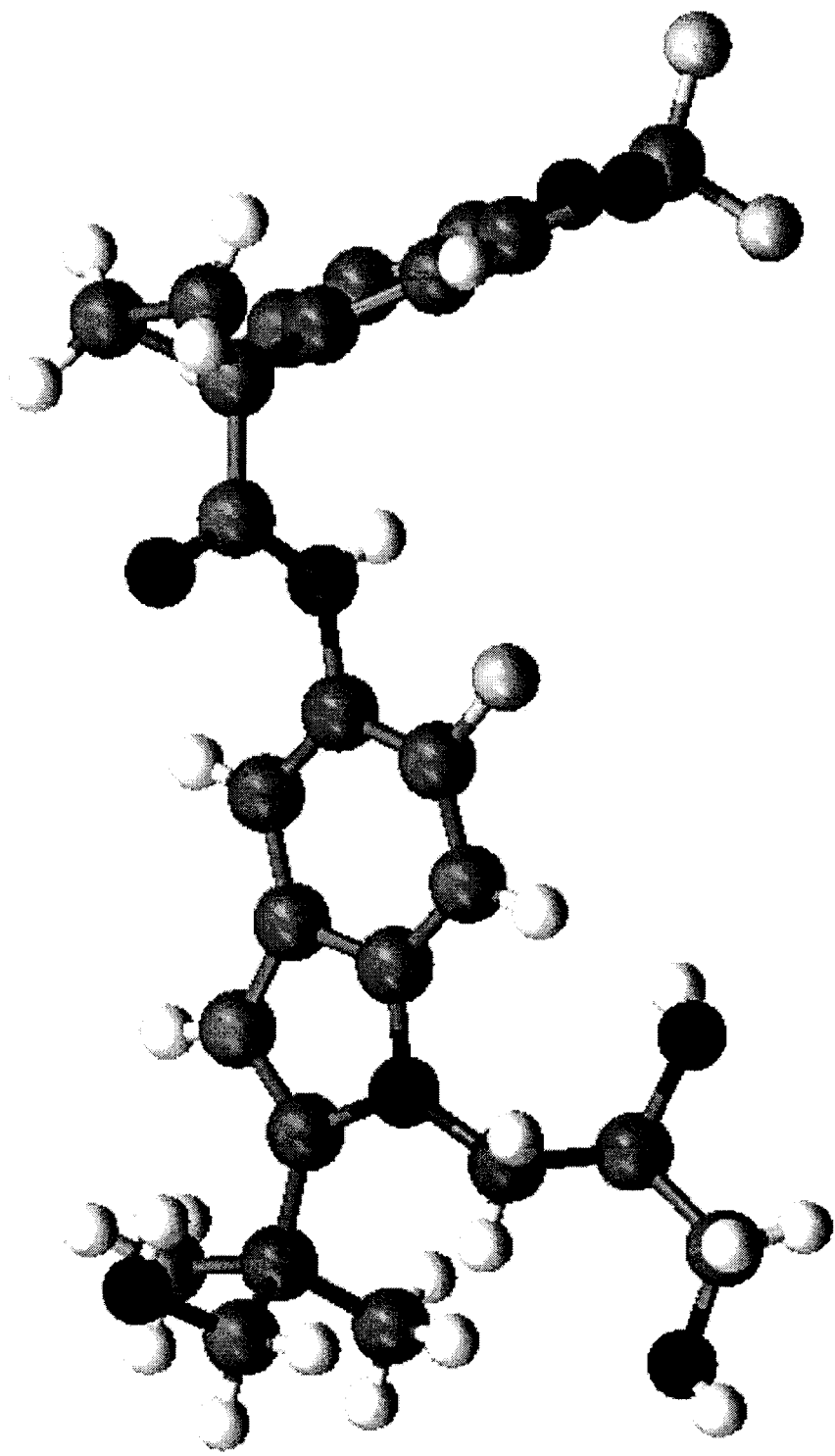
FIG. 9 is a conformational picture of Compound 1 Form A based on single crystal X-ray analysis.
Figure 10:
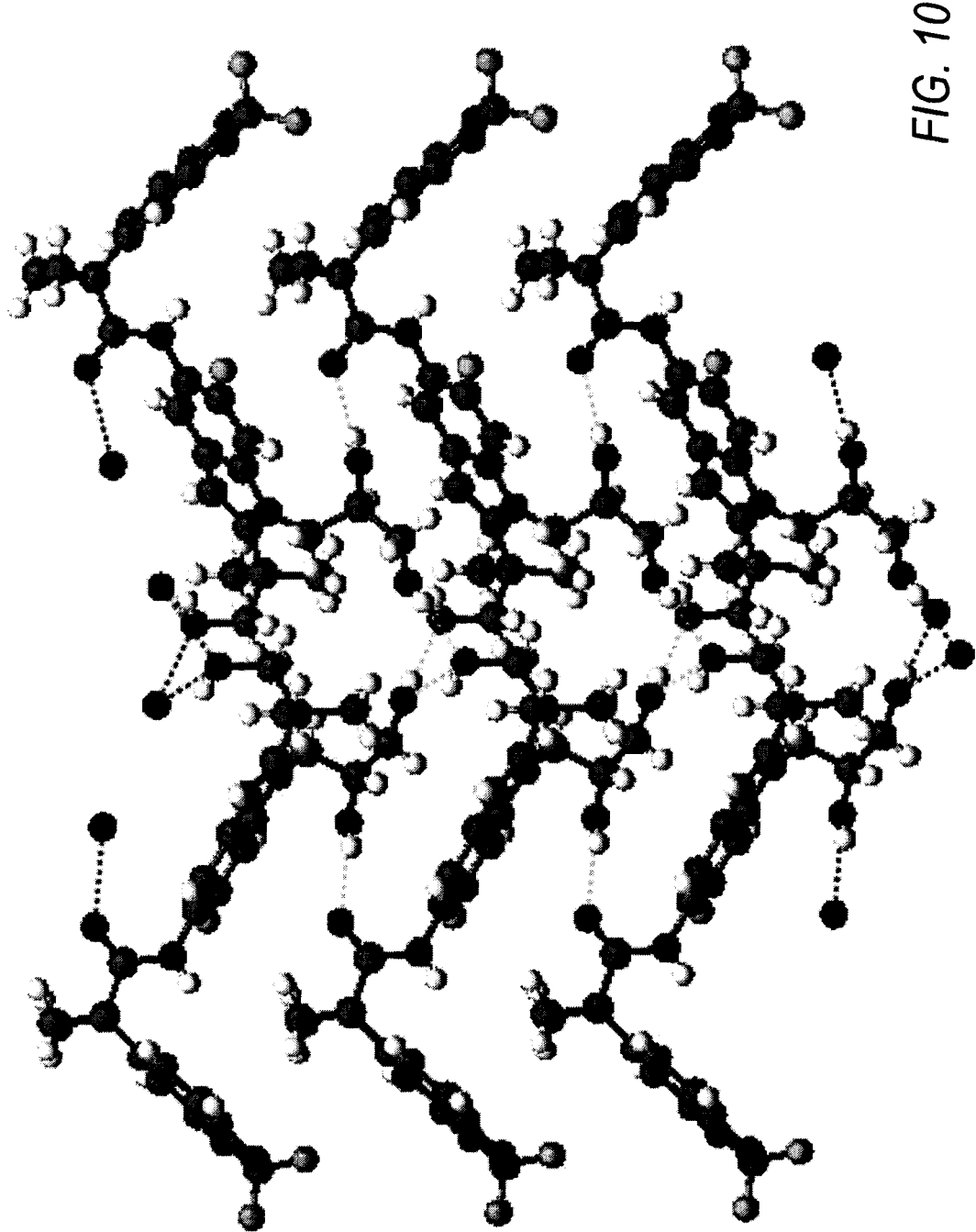
FIG. 10 is a conformational picture showing the stacking order of Compound 1 Form A.

Conformational pictures of Compound 1 Form A based on single crystal X-ray analysis are shown in FIGS. 9 and 10. The terminal —OH groups are connected via hydrogen bond networks to form a tetrameric cluster with four adjacent molecules (FIG. 10). The other hydroxyl group acts as a hydrogen bond donor to form a hydrogen bond with a carbonyl group from an adjacent molecule. The crystal structure reveals a dense packing of the molecules. Compound 1 Form A is monoclinic, C2 space group, with the following unit cell dimensions: a=21.0952(16) Å, b=6.6287(5) Å, c=17.7917 (15) Å, β=95.867(6)°, γ=90°.

Figure 11:
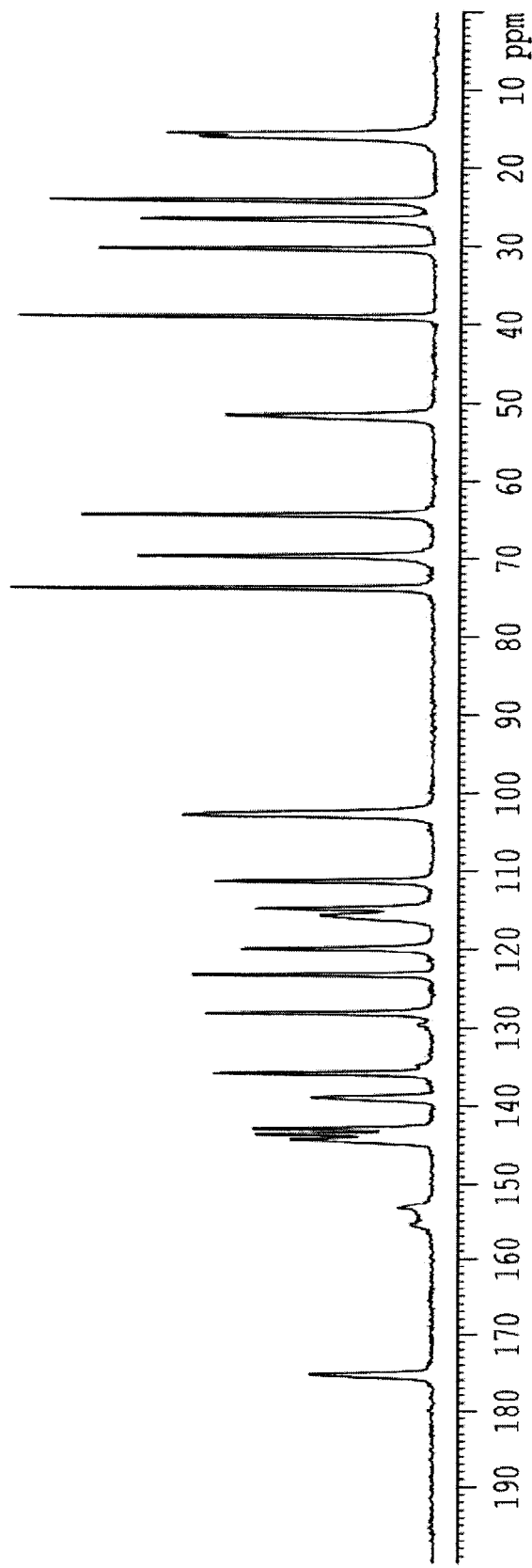
FIG. 11 is a solid state $^{13}$C NMR spectrum (15.0 kHz spinning) of Compound Form A.

A solid state $^{13}$C NMR spectrum of Compound 1 Form A is shown in FIG. 11. Table 8 provides chemical shifts of the relevant peaks.

TABLE 8

Compound 1 Form A
$^{13}$C Chem. Shifts

| Peak # | F1 [ppm] | Intensity |
|---|---|---|
| 1 | 175.3 | 2.9 |
| 2 | 155.4 | 0.54 |
| 3 | 153.3 | 0.81 |
| 4 | 144.3 | 3.35 |
| 5 | 143.7 | 4.16 |
| 6 | 143.0 | 4.24 |
| 7 | 139.0 | 2.86 |
| 8 | 135.8 | 5.19 |
| 9 | 128.2 | 5.39 |
| 10 | 123.3 | 5.68 |
| 11 | 120.0 | 4.55 |
| 12 | 115.8 | 2.66 |
| 13 | 114.9 | 4.2 |
| 14 | 111.3 | 5.17 |
| 15 | 102.8 | 5.93 |
| 16 | 73.8 | 10 |
| 17 | 69.8 | 7.06 |
| 18 | 64.5 | 8.29 |
| 19 | 51.6 | 4.96 |
| 20 | 39.1 | 9.83 |
| 21 | 30.5 | 7.97 |
| 22 | 26.8 | 6.94 |
| 23 | 24.4 | 9.19 |
| 24 | 16.3 | 5.58 |
| 25 | 15.8 | 6.33 |

Figure 12:
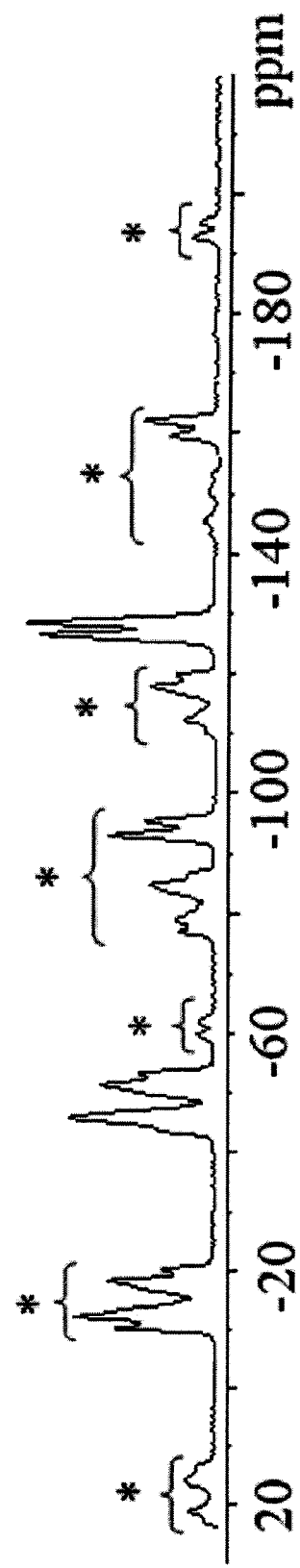
FIG. 12 is a solid state $^{19}$F NMR spectrum (12.5 kHz spinning) of Compound 1 Form A.

A solid state $^{19}$F NMR spectrum of Compound 1 Form A is shown in FIG. 12. Peaks with an asterisk denote spinning side bands. Table 9 provides chemical shifts of the relevant peaks.

TABLE 9

Compound 1 Form A
$^{19}$F Chem. Shifts

| Peak # | F1 [ppm] | Intensity |
|---|---|---|
| 1 | −45.9 | 9.48 |
| 2 | −51.4 | 7.48 |
| 3 | −53.3 | 4.92 |
| 4 | −126.5 | 11.44 |
| 5 | −128.4 | 12.5 |

Synthesis of Compound 1 Amorphous Form
Rotary Evaporation Method

Figure 13:
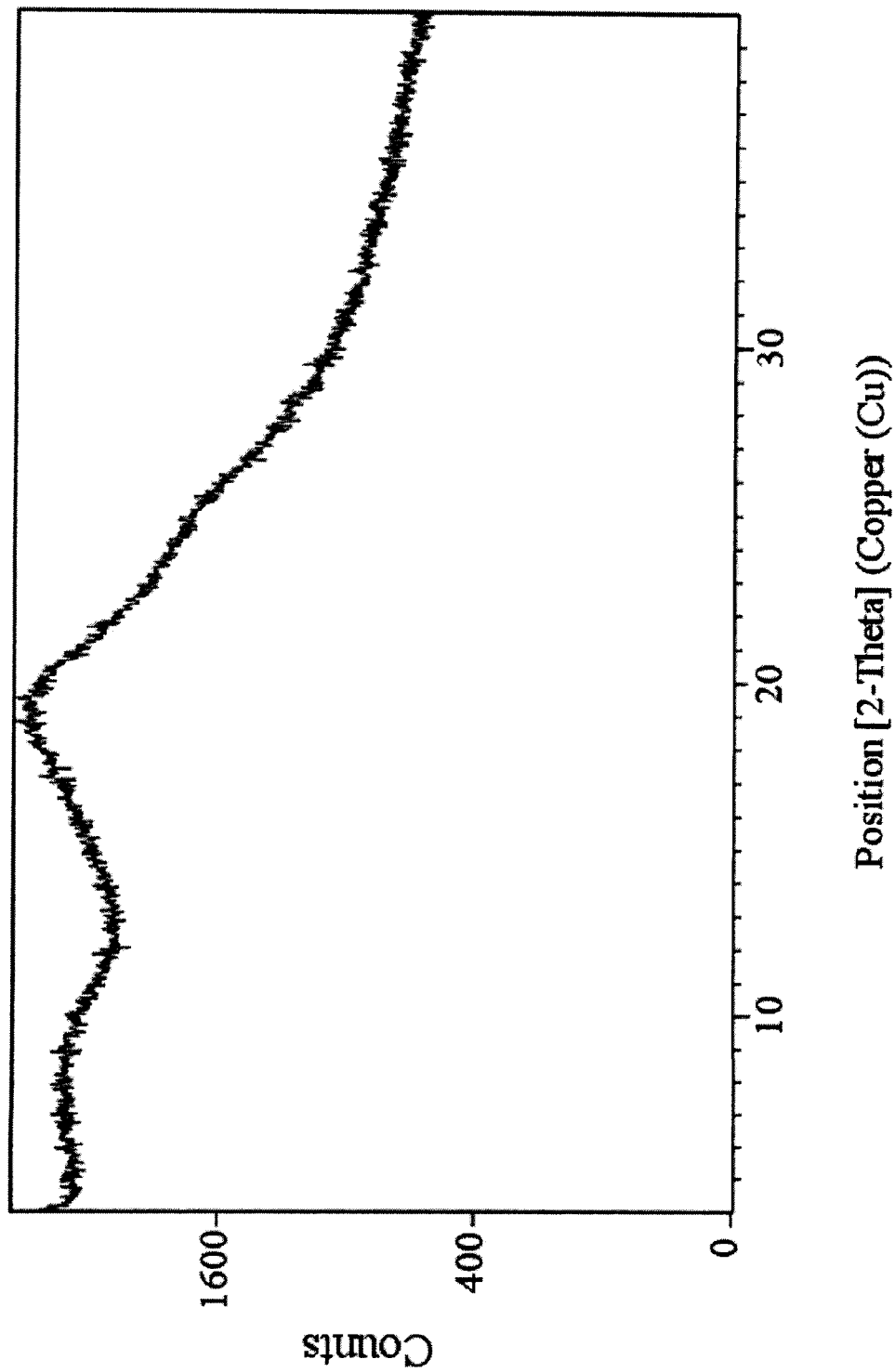
FIG. 13 is an X-ray powder diffraction pattern of Compound 1 amorphous form from the fast evaporation rotary evaporation method.
Figure 14:
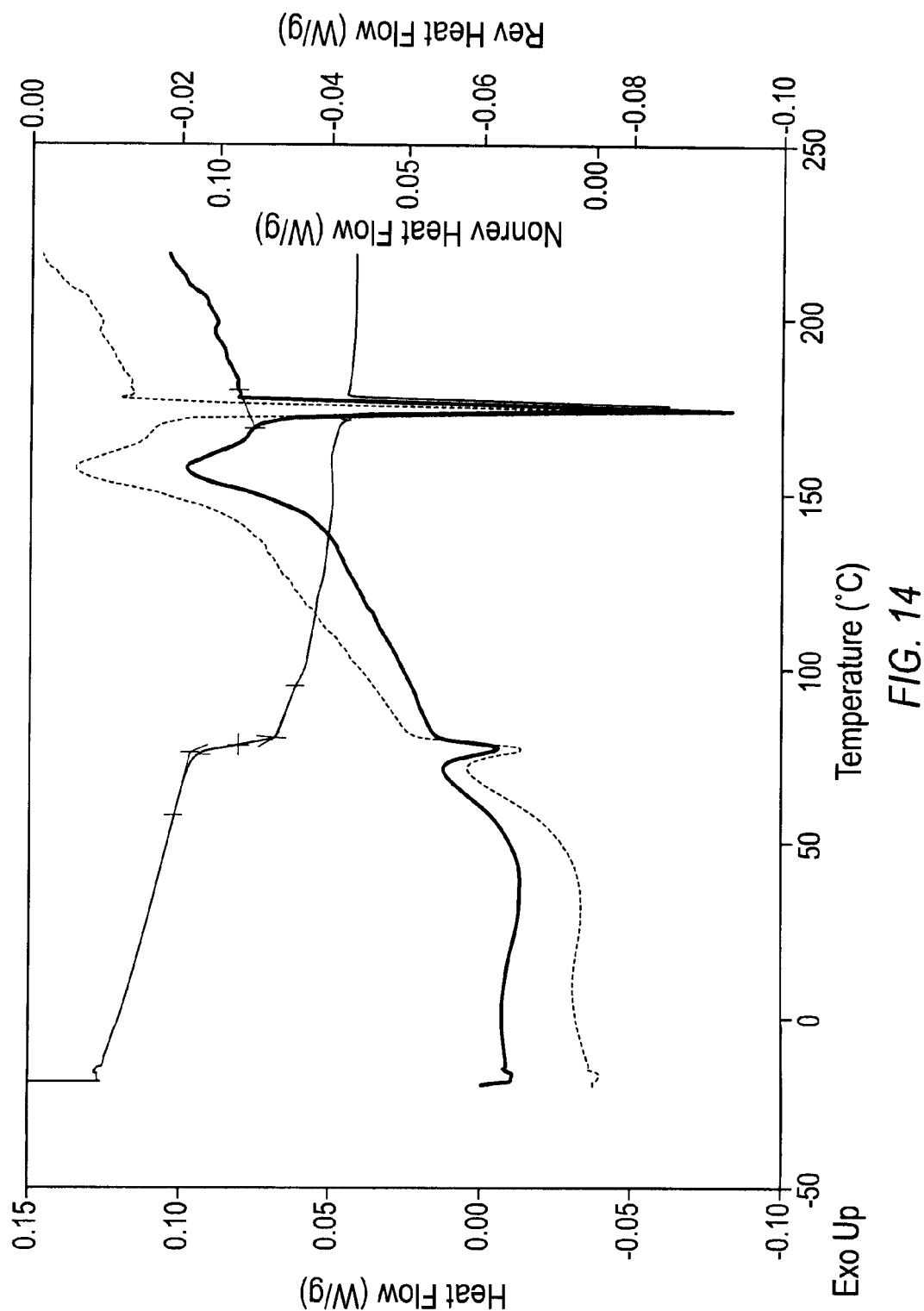
FIG. 14 is a modulated differential scanning calorimetry (MDSC) trace of Compound 1 amorphous form prepared by the fast evaporation rotary evaporation method.
Figure 15:
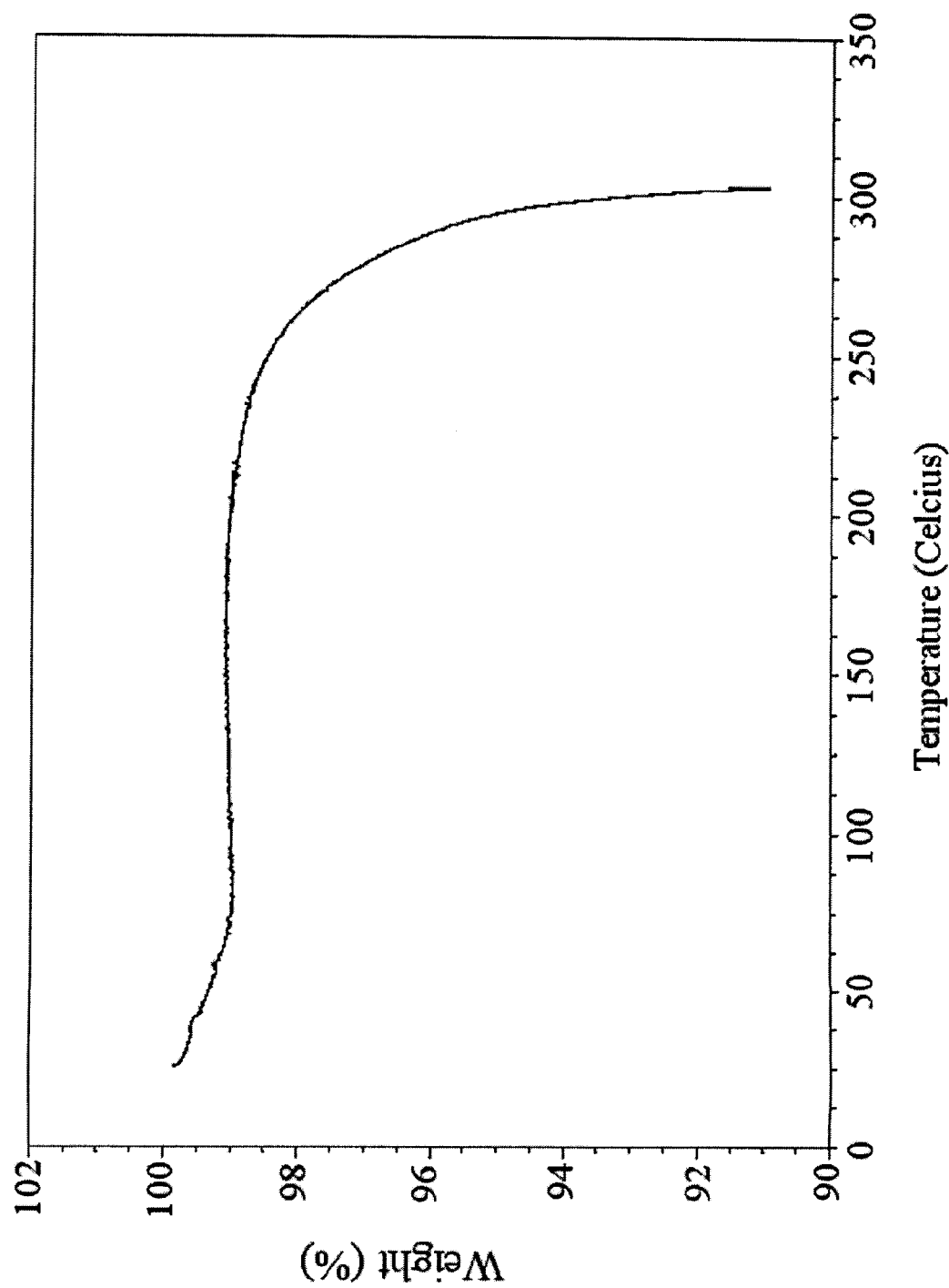
FIG. 15 is a thermogravimetric analysis (TGA) plot of Compound 1 amorphous form prepared by the fast evaporation rotary evaporation method.

Compound 1 amorphous form was also achieved via rotary evaporation. Compound 1 (approximately 10 g) was dissolved in 180 ml of MeOH and rotary evaporated in a 50° C. bath to a foam. DSC (FIG. 14) and XRPD (FIG. 13) confirmed amorphous form of Compound 1. FIG. 15 discloses a TGA trace of Compound 1 amorphous form prepared by this method.

Spray-Dried Method 9.95 g of Hydroxypropylmethylcellulose acetate succinate HG grade (HPMCAS-HG) was weighed into a 500 ml beaker, along with 50 mg of sodium lauryl sulfate (SLS). MeOH (200 ml) was mixed with the solid. The material was allowed to stir for 4 h. To insure maximum dissolution, after 2 h of stirring the solution was sonicated for 5 mins, then allowed to continue stirring for the remaining 2 h. A very fin suspension of HPMCAS remained in solution. However, visual observation determined that no gummy portions remained on the walls of the vessel or stuck to the bottom after tilting the vessel.

Compound 1 Form A (10 g) was poured into the 500 ml beaker, and the system was allowed to continue stirring. The solution was spray dried using the following parameters: Formulation Description: Compound 1 Form A/HPMCAS/SLS (50/49.5/0.5)

| Buchi Mini Spray Dryer | |
|---|---|
| T inlet (setpoint) | 145° C. |
| T outlet (start) | 75° C. |
| T outlet (end) | 55° C. |
| Nitrogen Pressure | 75 psi |
| Aspirator | 100% |
| Pump | 35% |
| Rotometer | 40 mm |
| Filter Pressure | 65 mbar |
| Condenser Temp | −3° C. |
| Run Time | 1 h |

Figure 16:
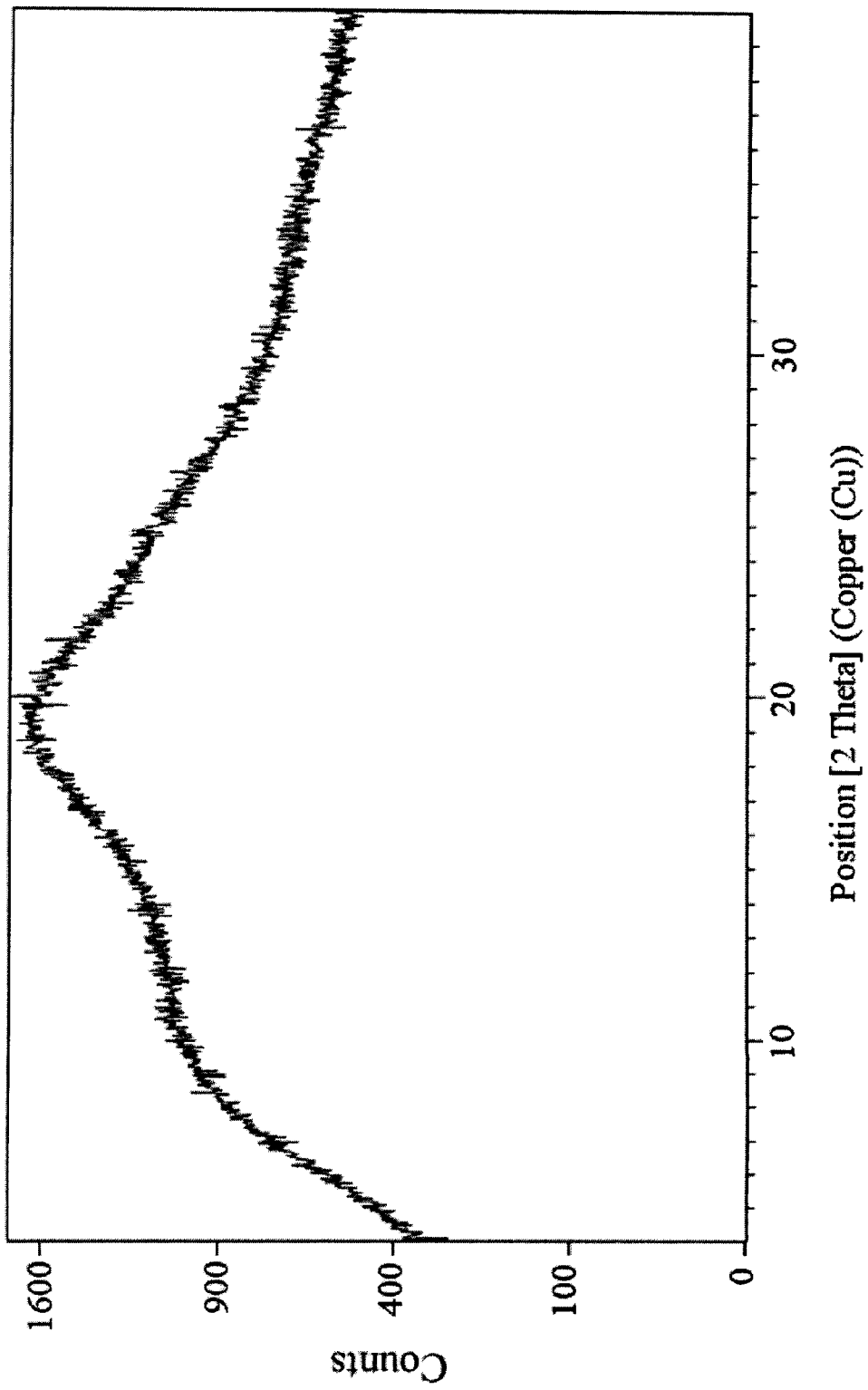
FIG. 16 is an X-ray powder diffraction pattern of Compound 1 amorphous form prepared by spray dried methods.
Figure 17:
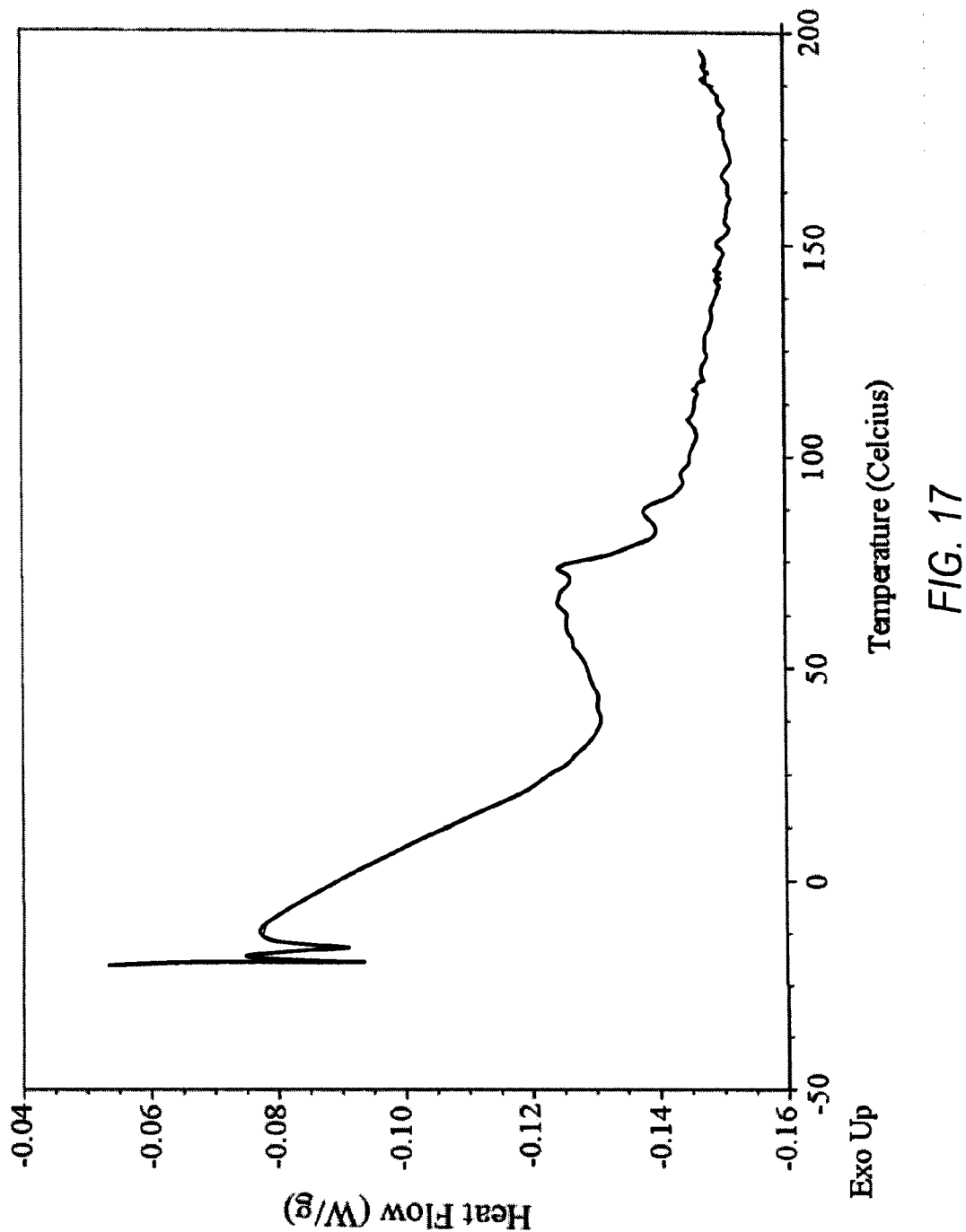
FIG. 17 is a modulated differential scanning calorimetry (MDSC) trace of Compound 1 amorphous form prepared by spray dried methods.

Approximately 16 g of Compound 1 amorphous form (80% yield) was recovered. Compound 1 amorphous form was confirmed by XRPD (FIG. 16) and DSC (FIG. 17).

Figure 18:
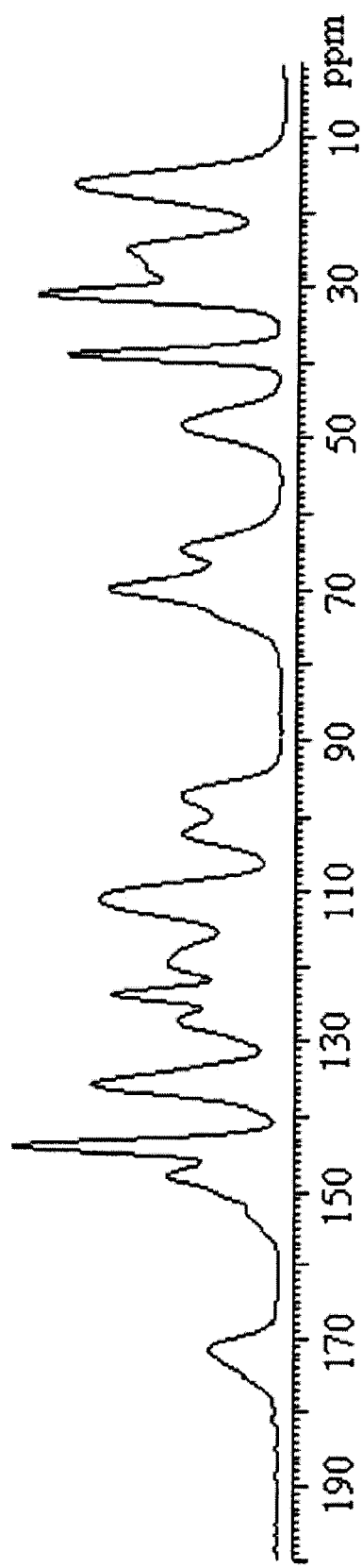
FIG. 18 is a solid state $^{13}$C NMR spectrum (15.0 kHz spinning) of Compound 1 amorphous form.

A solid state $^{13}$C NMR spectrum of Compound 1 amorphous form is shown in FIG. 18. Table 10 provides chemical shifts of the relevant peaks.

TABLE 10

Compound 1 amorphous form
$^{13}$C Chem. Shifts

| Peak # | F1 [ppm] | Intensity |
|---|---|---|
| 1 | 171.6 | 26.33 |
| 2 | 147.9 | 41.9 |
| 3 | 144.0 | 100 |
| 4 | 135.8 | 70.41 |
| 5 | 127.3 | 38.04 |
| 6 | 123.8 | 62.66 |
| 7 | 119.8 | 42.09 |
| 8 | 111.2 | 68.11 |
| 9 | 102.4 | 37.01 |
| 10 | 97.5 | 37.47 |
| 11 | 70.0 | 65.02 |
| 12 | 64.7 | 37.94 |
| 13 | 48.3 | 38.16 |
| 14 | 39.1 | 80.54 |
| 15 | 31.1 | 92.01 |
| 16 | 25.1 | 58.68 |
| 17 | 16.5 | 78.97 |

Figure 19:
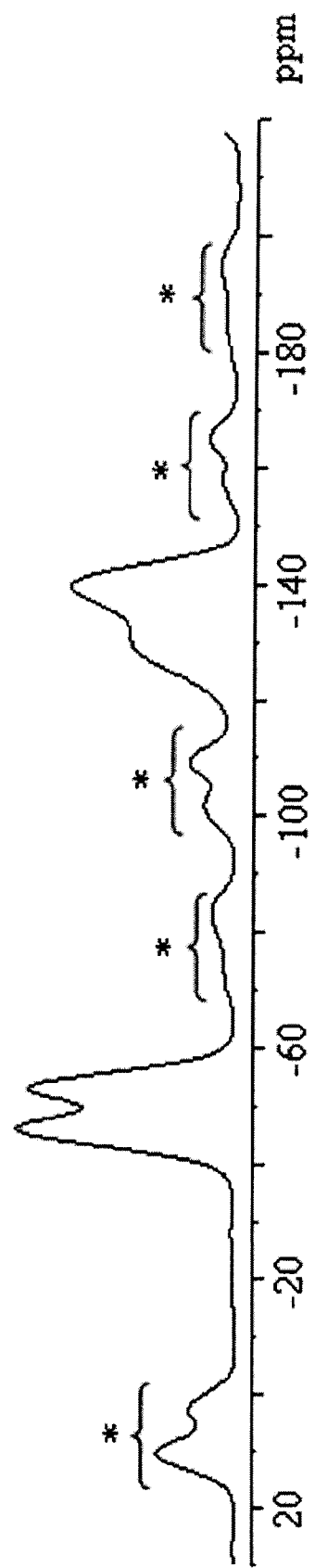
FIG. 19 is a solid state $^{19}$F NMR spectrum (12.5 kHz spinning) of Compound 1 amorphous form.

A solid state $^{19}$F NMR spectrum of Compound 1 amorphous form is shown in FIG. 19. Peaks with an asterisk denote spinning side bands. Table 11 provides chemical shifts of the relevant peaks.

TABLE 11

Compound 1 amorphous form
$^{19}$F Chem. Shifts

| Peak # | F1 [ppm] | Intensity |
|---|---|---|
| 1 | −46.1 | 100 |
| 2 | −53.1 | 94.9 |
| 3 | −139.4 | 76.05 |

Table 12 below recites additional analytical data for Compound 1.

TABLE 12

| Cmpd. No. | LC/MS M + 1 | LC/RT Min | NMR |
|---|---|---|---|
| 1 | 521.5 | 1.69 | 1H NMR (400.0 MHz, CD$_3$CN) d 7.69 (d, J = 7.7 Hz, 1H), 7.44 (d, J = 1.6 Hz, 1H), 7.39 (dd, J = 1.7, 8.3 Hz, 1H), 7.31 |

TABLE 12-continued

| Cmpd. No. | LC/MS M + 1 | LC/RT Min | NMR |
|---|---|---|---|
| | | | (s, 1H), 7.27 (d, J = 8.3 Hz, 1H), 7.20 (d, J = 12.0 Hz, 1H), 6.34 (s, 1H), 4.32 (d, J = 6.8 Hz, 2H), 4.15-4.09 (m, 1H), 3.89 (dd, J = 6.0, 11.5 Hz, 1H), 3.63-3.52 (m, 3H), 3.42 (d, J = 4.6 Hz, 1H), 3.21 (dd, J = 6.2, 7.2 Hz, 1H), 3.04 (t, J = 5.8 Hz, 1H), 1.59 (dd, J = 3.8, 6.8 Hz, 2H), 1.44 (s, 3H), 1.33 (s, 3H) and 1.18 (dd, J = 3.7, 6.8 Hz, 2H) ppm. |

Assays

Assays for Detecting and Measuring ΔF508-CFTR Correction Properties of Compounds Membrane Potential Optical Methods for Assaying ΔF508-CFTR Modulation Properties of Compounds The optical membrane potential assay utilized voltage-sensitive FRET sensors described by Gonzalez and Tsien (See, Gonzalez, J. E. and R. Y. Tsien (1995) "Voltage sensing by fluorescence resonance energy transfer in single cells" *Biophys J* 69(4): 1272-80, and Gonzalez, J. E. and R. Y. Tsien (1997) "Improved indicators of cell membrane potential that use fluorescence resonance energy transfer" *Chem Biol* 4(4): 269-77) in combination with instrumentation for measuring fluorescence changes such as the Voltage/Ion Probe Reader (VIPR) (See, Gonzalez, J. E., K. Oades, et al. (1999) "Cell-based assays and instrumentation for screening ion-channel targets" *Drug Discov Today* 4(9): 431-439).

These voltage sensitive assays are based on the change in fluorescence resonant energy transfer (FRET) between the membrane-soluble, voltage-sensitive dye, DiSBAC$_2$(3), and a fluorescent phospholipid, CC2-DMPE, which is attached to the outer leaflet of the plasma membrane and acts as a FRET donor. Changes in membrane potential ($V_m$) cause the negatively charged DiSBAC$_2$(3) to redistribute across the plasma membrane and the amount of energy transfer from CC2-DMPE changes accordingly. The changes in fluorescence emission were monitored using VIPR™ II, which is an integrated liquid handler and fluorescent detector designed to conduct cell-based screens in 96- or 384-well microtiter plates.

1. Identification of Correction Compounds

To identify small molecules that correct the trafficking defect associated with ΔF508-CFTR; a single-addition HTS assay format was developed. The cells were incubated in serum-free medium for 16 hrs at 37° C. in the presence or absence (negative control) of test compound. As a positive control, cells plated in 384-well plates were incubated for 16 hrs at 27° C. to "temperature-correct" ΔF508-CFTR. The cells were subsequently rinsed 3× with Krebs Ringers solution and loaded with the voltage-sensitive dyes. To activate ΔF508-CFTR, 10 μM forskolin and the CFTR potentiator, genistein (20 μM), were added along with Cl⁻-free medium to each well. The addition of Cl⁻-free medium promoted Cl⁻ efflux in response to ΔF508-CFTR activation and the resulting membrane depolarization was optically monitored using the FRET-based voltage-sensor dyes.

2. Identification of Potentiator Compounds

To identify potentiators of ΔF508-CFTR, a double-addition HTS assay format was developed. During the first addition, a Cl⁻-free medium with or without test compound was added to each well. After 22 sec, a second addition of CF-free medium containing 2-10 μM forskolin was added to activate ΔF508-CFTR. The extracellular Cl⁻ concentration following both additions was 28 mM, which promoted Cl⁻ efflux in response to ΔF508-CFTR activation and the resulting membrane depolarization was optically monitored using the FRET-based voltage-sensor dyes.

3. Solutions

Bath Solution #1: (in mM) NaCl 160, KCl 4.5, CaCl$_2$ 2, MgCl$_2$ 1, HEPES 10, pH 7.4 with NaOH.

Chloride-free bath solution: Chloride salts in Bath Solution #1 are substituted with gluconate salts.

CC2-DMPE: Prepared as a 10 mM stock solution in DMSO and stored at −20° C.

DiSBAC$_2$(3): Prepared as a 10 mM stock in DMSO and stored at −20° C.

4. Cell Culture

NIH3T3 mouse fibroblasts stably expressing ΔF508-CFTR are used for optical measurements of membrane potential. The cells are maintained at 37° C. in 5% CO$_2$ and 90% humidity in Dulbecco's modified Eagle's medium supplemented with 2 mM glutamine, 10% fetal bovine serum, 1×NEAA, β-ME, 1× pen/strep, and 25 mM HEPES in 175 cm² culture flasks. For all optical assays, the cells were seeded at 30,000/well in 384-well matrigel-coated plates and cultured for 2 hrs at 37° C. before culturing at 27° C. for 24 hrs for the potentiator assay. For the correction assays, the cells are cultured at 27° C. or 37° C. with and without compounds for 16-24 hours.

Electrophysiological Assays for Assaying ΔF508-CFTR Modulation Properties of Compounds 1. Using Chamber Assay Using chamber experiments were performed on polarized epithelial cells expressing ΔF508-CFTR to further characterize the ΔF508-CFTR modulators identified in the optical assays. FRT$^{\Delta F508-CFTR}$ epithelial cells grown on Costar Snapwell cell culture inserts were mounted in an Ussing chamber (Physiologic Instruments, Inc., San Diego, Calif.), and the monolayers were continuously short-circuited using a Voltage-clamp System (Department of Bioengineering, University of Iowa, IA, and, Physiologic Instruments, Inc., San Diego, Calif.). Transepithelial resistance was measured by applying a 2-mV pulse. Under these conditions, the FRT epithelia demonstrated resistances of 4 KΩ/cm² or more. The solutions were maintained at 27° C. and bubbled with air. The electrode offset potential and fluid resistance were corrected using a cell-free insert. Under these conditions, the current reflects the flow of Cl⁻ through ΔF508-CFTR expressed in the apical membrane. The I$_{SC}$ was digitally acquired using an MP100A-CE interface and AcqKnowledge software (v3.2.6; BIOPAC Systems, Santa Barbara, Calif.).

2. Identification of Correction Compounds

Typical protocol utilized a basolateral to apical membrane Cl⁻ concentration gradient. To set up this gradient, normal ringer was used on the basolateral membrane; whereas apical NaCl was replaced by equimolar sodium gluconate (titrated to pH 7.4 with NaOH) to give a large Cl⁻ concentration gradient across the epithelium. All experiments were performed with intact monolayers. To fully activate ΔF508-CFTR, forskolin (10 μM) and the PDE inhibitor, IBMX (100 μM), were applied followed by the addition of the CFTR potentiator, genistein (50 μM).

As observed in other cell types, incubation at low temperatures of FRT cells stably expressing ΔF508-CFTR increases the functional density of CFTR in the plasma membrane. To determine the activity of correction compounds, the cells were incubated with 10 μM of the test compound for 24 hours at 37° C. and were subsequently washed 3× prior to recording. The cAMP- and genistein-mediated I$_{SC}$ in compound-treated cells was normalized to the 27° C. and 37° C. controls and expressed as percentage activity. Preincubation of the cells with the correction compound significantly increased the cAMP- and genistein-mediated $I_{sc}$ compared to the 37° C. controls.

3. Identification of Potentiator Compounds

Typical protocol utilized a basolateral to apical membrane Cl⁻ concentration gradient. To set up this gradient, normal ringers was used on the basolateral membrane and was permeabilized with nystatin (360 µg/ml), whereas apical NaCl was replaced by equimolar sodium gluconate (titrated to pH 7.4 with NaOH) to give a large Cl⁻ concentration gradient across the epithelium. All experiments were performed 30 min after nystatin permeabilization. Forskolin (10 µM) and all test compounds were added to both sides of the cell culture inserts. The efficacy of the putative ΔF508-CFTR potentiators was compared to that of the known potentiator, genistein.

4. Solutions

Basolateral solution (in mM): NaCl (135), $CaCl_2$ (1.2), $MgCl_2$ (1.2), $K_2HPO_4$ (2.4), $KHPO_4$ (0.6), N-2-hydroxyethylpiperazine-N'-2-ethanesulfonic acid (HEPES) (10), and dextrose (10). The solution was titrated to pH 7.4 with NaOH.

Apical solution (in mM): Same as basolateral solution with NaCl replaced with Na Gluconate (135).

5. Cell Culture

Fisher rat epithelial (FRT) cells expressing ΔF508-CFTR ($FRT^{\Delta F508-CFTR}$) were used for Ussing chamber experiments for the putative ΔF508-CFTR modulators identified from our optical assays. The cells were cultured on Costar Snapwell cell culture inserts and cultured for five days at 37° C. and 5% $CO_2$ in Coon's modified Ham's F-12 medium supplemented with 5% fetal calf serum, 100 U/ml penicillin, and 100 µg/ml streptomycin. Prior to use for characterizing the potentiator activity of compounds, the cells were incubated at 27° C. for 16-48 hrs to correct for the ΔF508-CFTR. To determine the activity of corrections compounds, the cells were incubated at 27° C. or 37° C. with and without the compounds for 24 hours.

6. Whole-Cell Recordings

The macroscopic ΔF508-CFTR current ($I_{\Delta F508}$) in temperature- and test compound-corrected NIH3T3 cells stably expressing ΔF508-CFTR were monitored using the perforated-patch, whole-cell recording. Briefly, voltage-clamp recordings of $I_{\Delta F508}$ were performed at room temperature using an Axopatch 200B patch-clamp amplifier (Axon Instruments Inc., Foster City, Calif.). All recordings were acquired at a sampling frequency of 10 kHz and low-pass filtered at 1 kHz. Pipettes had a resistance of 5-6 MΩ when filled with the intracellular solution. Under these recording conditions, the calculated reversal potential for Cl⁻ ($E_{Cl}$) at room temperature was −28 mV. All recordings had a seal resistance >20 GΩ and a series resistance <15 MΩ. Pulse generation, data acquisition, and analysis were performed using a PC equipped with a Digidata 1320 A/D interface in conjunction with Clampex 8 (Axon Instruments Inc.). The bath contained <250 µl of saline and was continuously perifused at a rate of 2 ml/min using a gravity-driven perfusion system.

7. Identification of Correction Compounds

To determine the activity of correction compounds for increasing the density of functional ΔF508-CFTR in the plasma membrane, we used the above-described perforated-patch-recording techniques to measure the current density following 24-hr treatment with the correction compounds. To fully activate ΔF508-CFTR, 10 µM forskolin and 20 µM genistein were added to the cells. Under our recording conditions, the current density following 24-hr incubation at 27° C. was higher than that observed following 24-hr incubation at 37° C. These results are consistent with the known effects of low-temperature incubation on the density of ΔF508-CFTR in the plasma membrane. To determine the effects of correction compounds on CFTR current density, the cells were incubated with 10 µM of the test compound for 24 hours at 37° C. and the current density was compared to the 27° C. and 37° C. controls (% activity). Prior to recording, the cells were washed 3× with extracellular recording medium to remove any remaining test compound. Preincubation with 10 µM of correction compounds significantly increased the cAMP- and genistein-dependent current compared to the 37° C. controls.

8. Identification of Potentiator Compounds

The ability of ΔF508-CFTR potentiators to increase the macroscopic ΔF508-CFTR Cl⁻ current ($I_{\Delta F508}$) in NIH3T3 cells stably expressing ΔF508-CFTR was also investigated using perforated-patch-recording techniques. The potentiators identified from the optical assays evoked a dose-dependent increase in $I_{\Delta F508}$ with similar potency and efficacy observed in the optical assays. In all cells examined, the reversal potential before and during potentiator application was around −30 mV, which is the calculated $E_{Cl}$ (−28 mV).

9. Solutions

Intracellular solution (in mM): Cs-aspartate (90), CsCl (50), $MgCl_2$ (1), HEPES (10), and 240 µg/ml amphotericin-B (pH adjusted to 7.35 with CsOH).

Extracellular solution (in mM): N-methyl-D-glucamine (NMDG)-Cl (150), $MgCl_2$ (2), $CaCl_2$ (2), HEPES (10) (pH adjusted to 7.35 with HCl).

10. Cell Culture

NIH3T3 mouse fibroblasts stably expressing ΔF508-CFTR are used for whole-cell recordings. The cells are maintained at 37° C. in 5% $CO_2$ and 90% humidity in Dulbecco's modified Eagle's medium supplemented with 2 mM glutamine, 10% fetal bovine serum, 1×NEAA, β-ME, 1× pen/strep, and 25 mM HEPES in 175 cm² culture flasks. For whole-cell recordings, 2,500-5,000 cells were seeded on poly-L-lysine-coated glass coverslips and cultured for 24-48 hrs at 27° C. before use to test the activity of potentiators; and incubated with or without the correction compound at 37° C. for measuring the activity of correctors.

11. Single-Channel Recordings

The single-channel activities of temperature-corrected ΔF508-CFTR stably expressed in NIH3T3 cells and activities of potentiator compounds were observed using excised inside-out membrane patch. Briefly, voltage-clamp recordings of single-channel activity were performed at room temperature with an Axopatch 200B patch-clamp amplifier (Axon Instruments Inc.). All recordings were acquired at a sampling frequency of 10 kHz and low-pass filtered at 400 Hz. Patch pipettes were fabricated from Corning Kovar Sealing #7052 glass (World Precision Instruments, Inc., Sarasota, Fla.) and had a resistance of 5-8 MΩ when filled with the extracellular solution. The ΔF508-CFTR was activated after excision, by adding 1 mM Mg-ATP, and 75 nM of the cAMP-dependent protein kinase, catalytic subunit (PKA; Promega Corp. Madison, Wis.). After channel activity stabilized, the patch was perifused using a gravity-driven microperfusion system. The inflow was placed adjacent to the patch, resulting in complete solution exchange within 1-2 sec. To maintain ΔF508-CFTR activity during the rapid perifusion, the non-specific phosphatase inhibitor F⁻ (10 mM NaF) was added to the bath solution. Under these recording conditions, channel activity remained constant throughout the duration of the patch recording (up to 60 min). Currents produced by positive charge moving from the intra- to extracellular solutions (anions moving in the opposite direction) are shown as positive currents. The pipette potential ($V_p$) was maintained at 80 mV.

Channel activity was analyzed from membrane patches containing ≤2 active channels. The maximum number of simultaneous openings determined the number of active channels during the course of an experiment. To determine the single-channel current amplitude, the data recorded from 120 sec of ΔF508-CFTR activity was filtered "off-line" at 100 Hz and then used to construct all-point amplitude histograms that were fitted with multigaussian functions using Bio-Patch Analysis software (Bio-Logic Comp. France). The total microscopic current and open probability ($P_o$) were determined from 120 sec of channel activity. The $P_o$ was determined using the Bio-Patch software or from the relationship $P_o=I/i(N)$, where I=mean current, i=single-channel current amplitude, and N=number of active channels in patch.

12. Solutions

Extracellular solution (in mM): NMDG (150), aspartic acid (150), $CaCl_2$ (5), $MgCl_2$ (2), and HEPES (10) (pH adjusted to 7.35 with Tris base).

Intracellular solution (in mM): NMDG-Cl (150), $MgCl_2$ (2), EGTA (5), TES (10), and Tris base (14) (pH adjusted to 7.35 with HCl).

13. Cell Culture

NIH3T3 mouse fibroblasts stably expressing ΔF508-CFTR are used for excised-membrane patch-clamp recordings. The cells are maintained at 37° C. in 5% $CO_2$ and 90% humidity in Dulbecco's modified Eagle's medium supplemented with 2 mM glutamine, 10% fetal bovine serum, 1×NEAA, β-ME, 1× pen/strep, and 25 mM HEPES in 175 $cm^2$ culture flasks. For single channel recordings, 2,500-5,000 cells were seeded on poly-L-lysine-coated glass coverslips and cultured for 24-48 hrs at 27° C. before use.

Using the procedures described above, the activity, i.e., EC50s, of Compound 1 has been measured and is shown in Table 13.

TABLE 13

IC50/EC50 Bins: +++ <= 2.0 < ++ <= 5.0 < +
PercentActivity Bins: + <= 25.0 < ++ <= 100.0 < +++

| Cmpd. No. | BinnedEC50 | BinnedMaxEfficacy |
|---|---|---|
| 1 | +++ | +++ |

We claim:

1. (R)-1-(2,2-Difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide crystalline Form A characterized by one or more peaks at 19.3 to 19.7 degrees, 21.5 to 21.9 degrees, 16.9 to 17.3, and 20.2 to 20.6 degrees in an X-ray powder diffraction obtained using Cu K alpha radiation.

2. (R)-1-(2,2-Difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide crystalline Form A of claim 1 characterized by one or more peaks at about 19.5, 21.7, and 17.1 degrees.

3. (R)-1-(2,2-Difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide crystalline Form A of claim 1 characterized by a peak at about 20.4 degrees.

4. (R)-1-(2,2-Difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide crystalline Form A of claim 1 further characterized by a peak at 18.6 to 19.0 degrees.

5. (R)-1-(2,2-Difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide crystalline Form A of claim 4 characterized by a peak at about 18.8 degrees.

6. (R)-1-(2,2-Difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide crystalline Form A of claim 1 further characterized by a peak at 24.5 to 24.9 degrees.

7. (R)-1-(2,2-Difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide crystalline Form A of claim 6 characterized by a peak at about 24.7 degrees.

8. (R)-1-(2,2-Difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide crystalline Form A of claim 1 further characterized by a peak at 9.8 to 10.2 degrees.

9. (R)-1-(2,2-Difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide crystalline Form A of claim 8 characterized by a peak at about 10.0 degrees.

10. (R)-1-(2,2-Difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide crystalline Form A of claim 1 further characterized by a peak at 4.8 to 5.2 degrees.

11. (R)-1-(2,2-Difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide crystalline Form A of claim 9 characterized by a peak at about 5.0 degrees.

12. (R)-1-(2,2-Difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide crystalline Form A of claim 1 further characterized by a peak at 24.0 to 24.4 degrees.

13. (R)-1-(2,2-Difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide crystalline Form A of claim 12 characterized by a peak at about 24.2 degrees.

14. (R)-1-(2,2-Difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide crystalline Form A of claim 1 further characterized by a peak at 18.3 to 18.7 degrees.

15. (R)-1-(2,2-Difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide crystalline Form A of claim 14 characterized by a peak at about 18.5 degrees.

16. (R)-1-(2,2-Difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide crystalline Form A of claim 1 characterized by a diffraction pattern substantially similar to that of FIG. 4.

17. (R)-1-(2,2-Difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide crystalline Form A of claim 1 characterized by a diffraction pattern substantially similar to that of FIG. 5.

18. (R)-1-(2,2-Difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide crystalline Form A having a monoclinic crystal system, a C2 space group, and the following unit cell dimensions:

| | |
|---|---|
| a = 21.0952(16) Å | α = 90° |
| b = 6.6287(5) Å | β = 95.867(6)° |
| c = 17.7917(15) Å | γ = 90°. |

19. A pharmaceutical composition comprising (R)-1-(2,2-difluorobenzo[d][1,3]-dioxol-5-yl)-N-(1-(2,3-dihydroxypropyl)-6-fluoro-2-(1-hydroxy-2-methylpropan-2-yl)-1H-indol-5-yl)cyclopropanecarboxamide crystalline Form A of claim 1, and a pharmaceutically acceptable carrier.

20. The pharmaceutical composition of claim 19, further comprising an additional therapeutic agent.

21. The pharmaceutical composition of claim 20, wherein the additional therapeutic agent is selected from a mucolytic agent, bronchodialator, an anti-biotic, an anti-infective agent, an anti-inflammatory agent, a CFTR potentiator, or a nutritional agent.

22. A process of preparing the Form A of claim 1 comprising slurrying (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide in a solvent for an effective amount of time.

23. The process of claim 22, wherein the solvent is ethyl acetate, dichloromethane, MTBE, isopropyl acetate, water/ethanol, water/acetonitrile, water/methanol, or water/isopropyl alcohol.

24. The process of claim 22, wherein the effective amount of time is 24 hours to 2 weeks.

25. A process of preparing the Form A of claim 1 comprising dissolving (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide in a solvent and evaporating the solvent.

26. The process of claim 25, wherein the solvent is acetone, acetonitrile, methanol, or isopropyl alcohol.

27. A process of preparing the Form A of claim 1 comprising dissolving (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide in a first solvent and adding a second solvent that (R)-1-(2,2-difluorobenzo[d][1,3]dioxol-5-yl)- N-(1-(2,3-dihydroxypropyl)-6-fluoro-2-(1-hydroxy-2-methylpropan-2-yl)-1H-indol-5-yl)cyclopropanecarboxamide is not soluble in.

28. The process of claim 27, wherein the first solvent is ethyl acetate, ethanol, isopropyl alcohol, or acetone.

29. The process of claim 27, wherein the second solvent is heptane or water.

30. The process of claim 27, wherein the addition of the second solvent is done while stirring the solution of the first solvent and (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide.

31. A method of treating a CFTR mediated disease in a subject comprising administering to the subject an effective amount of Form A of claim 1, wherein the CFTR mediated disease is selected from cystic fibrosis, hereditary emphysema, chronic obstructive pulmonary disease (COPD), and dry-eye disease.

32. The method of claim 31, wherein the CFTR mediated disease is cystic fibrosis.

33. The method of claim 31, wherein the subject has cystic fibrosis transmembrane receptor (CFTR) with a ΔF508 mutation.

34. The method of claim 31, wherein the subject has cystic fibrosis transmembrane receptor (CFTR) with a R117H mutation.

35. The method of claim 31, wherein the subject has cystic fibrosis transmembrane receptor (CFTR) with a G551D mutation.

36. The method of claim 31, wherein the method comprises administering an additional therapeutic agent.

37. The method of claim 36, wherein the therapeutic agent is selected from a mucolytic agent, bronchodialator, an anti-biotic, an anti-infective agent, an anti-inflammatory agent, a CFTR potentiator, or a nutritional agent.

38. A kit comprising (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide crystalline Form A of claim 1, and instructions for use thereof.

39. The pharmaceutical composition of claim 21, wherein the additional therapeutic agent is N-(5-hydroxy-2,4-ditert-butyl-phenyl)-4-oxo-1H-quinoline-3-carboxamide.

40. The method of claim 36, wherein the additional therapeutic agent is N-(5-hydroxy-2,4-ditert-butyl-phenyl)-4-oxo-1H-quinoline-3-carboxamide.

* * * * *